(12) United States Patent
Kondo et al.

(10) Patent No.: US 6,197,217 B1
(45) Date of Patent: Mar. 6, 2001

(54) 3,3'-DIFLUOROBIPHENYL DERIVATIVES, LIQUID CRYSTAL COMPOSITIONS, AND LIQUID CRYSTAL DISPLAY ELEMENTS

(75) Inventors: Tomoyuki Kondo; Shuichi Matsui; Kazutoshi Miyazawa; Hiroyuki Takeuchi; Fusayuki Takeshita; Etsuo Nakagawa, all of Chiba (JP)

(73) Assignee: Chisso Corporation, Osaka (JP)

(*) Notice: Subject to any disclaimer, the term of this patent is extended or adjusted under 35 U.S.C. 154(b) by 0 days.

(21) Appl. No.: 09/308,775

(22) PCT Filed: Nov. 21, 1997

(86) PCT No.: PCT/JP97/04265

§ 371 Date: May 25, 1999

§ 102(e) Date: May 25, 1999

(87) PCT Pub. No.: WO98/23562

PCT Pub. Date: Jun. 4, 1998

(30) Foreign Application Priority Data

Nov. 25, 1996 (JP) .................................................. 8-329158

(51) Int. Cl.[7] .......................... C09K 19/12; C09K 19/34; C09K 19/30

(52) U.S. Cl. ................... 252/299.66; 252/299.63; 252/299.61

(58) Field of Search .................... 252/299.66, 299.61, 252/299.63

(56) References Cited

U.S. PATENT DOCUMENTS

| | | | |
|---|---|---|---|
| 5,494,605 | * 2/1996 | Kurihara et al. | 252/299.66 |
| 5,578,244 | * 11/1996 | Shimizu et al. | 252/299.61 |
| 5,800,737 | * 9/1998 | Chan | 252/299.66 |
| 5,965,060 | * 10/1999 | Tarumi et al. | 252/299.63 |

FOREIGN PATENT DOCUMENTS

| | | |
|---|---|---|
| 2240778 | 8/1991 | (GB) . |
| 2258232 | 2/1993 | (GB) . |
| 64-29342 | 1/1989 | (JP) . |
| 2-67232 | 3/1990 | (JP) . |
| 2-501071 | 4/1990 | (JP) . |
| 3-141237 | 6/1991 | (JP) . |

OTHER PUBLICATIONS

Chemical Abstracts, vol. 122, No. 22, May 29, 1995 Columbus, Ohio, US; abstract No. 278263, Yamazaki, Yasuhiro et al: "Liquid–crystal composition" XP002140537 & JP 06 228037 A (Kanto Kagaku, Japan) Aug. 16, 1994.

* cited by examiner

Primary Examiner—C. H. Kelly
(74) Attorney, Agent, or Firm—Wenderoth, Lind & Ponack, L.L.P.

(57) ABSTRACT

Liquid crystalline compounds which exhibit a negative dielectric anisotropy value, have an extremely high voltage holding ratio and a low threshold voltage, are small in their dependency on temperature, hardly exhibit smectic phase, and are excellent in miscibility with other liquid crystal materials at the same time; liquid crystal compositions comprising the compound; and liquid crystal display devices fabricated by using the liquid crystal composition are provided; the liquid crystalline compounds being specific 3,3'-difluorobiphenyl derivatives expressed by the following general formula (1):

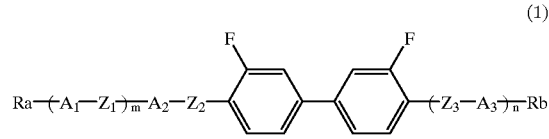

16 Claims, No Drawings

3,3'-DIFLUOROBIPHENYL DERIVATIVES, LIQUID CRYSTAL COMPOSITIONS, AND LIQUID CRYSTAL DISPLAY ELEMENTS

This application is a 371 National Stage application of International Application No. PCT/JP97/04265 filed Nov. 21, 1997.

TECHNICAL FIELD

The present invention relates to novel liquid crystalline compounds and liquid crystal compositions. More specifically, the invention relates to liquid crystalline compounds having 3,3'-difluorobiphenyl-4,4'-diyl group, liquid crystal compositions comprising the compound, and liquid crystal display devices fabricated by using the liquid crystal composition.

BACKGROUND ART

Display devices produced by using liquid crystalline compounds (the term "liquid crystalline compounds" is used in this specification as a general term for the compounds which exhibit a liquid crystal phase and for the compounds which do not exhibit a liquid crystal phase but are useful as component of liquid crystal compositions) have widely been utilized for the display of watches, tabletop calculators, word processors, or the likes. In recent years, researches on in-plane switching (IPS) mode and vertical alignment (VA) mode by which viewing angle can be improved at a moderate cost have extensively been conducted.

Among the liquid crystal compositions for IPS mode or VA mode, those having a negative dielectric anisotropy value are preferable, and further the compositions are sought having such physical properties as voltage holding ratio is high, threshold voltage is low, their dependency on temperature is small, temperature range of liquid crystal phase is wide, miscibility with other liquid crystal materials is excellent, and viscosity is low.

As the component for such liquid crystal compositions, many liquid crystalline compounds in which fluorine atom substituted at a lateral position were investigated, and the patents disclosing, for example, the following compounds are published:

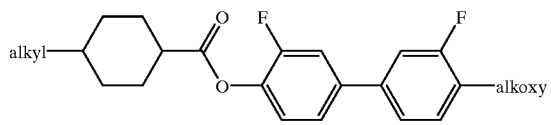

1) Japanese Patent Application laid-open No. Sho 64-29342

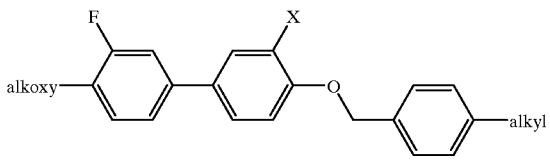

2) Japanese Patent Application laid-open No. Hei 3-141237

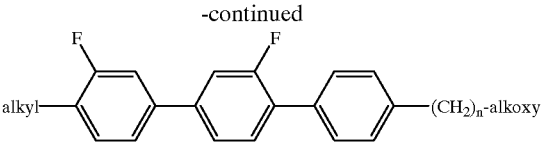

3) GB 2258232A

However, compounds of the formula 1) are high in viscosity and low in voltage holding ratio since they have ester bond. Compounds of the formula 2) or 3) have problems such that the compounds readily exhibit smectic phase, and hardly form stable nematic phase when used as component of liquid crystal compositions, particularly at low temperatures.

DISCLOSURE OF THE INVENTION

In view of the required characteristics described above, an object of the present invention is to provide liquid crystalline compounds which exhibit a negative dielectric anisotropy value, have an extremely high voltage holding ratio and a low threshold, voltage, are small in their dependency on temperature, hardly exhibit smectic phase, and are excellent in miscibility with other liquid crystal materials at the same time; to provide liquid crystal compositions comprising the compound; and to provide liquid crystal display devices fabricated by using the liquid crystal composition.

As a result of diligent studies by the present inventors to solve the problems described above, it has been found out that

[1] 3,3'-difluorobiphenyl derivatives expressed by the general formula (1)

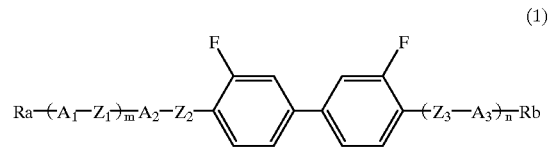

wherein Ra and Rb each independently represent a straight chain or branched alkyl group having 1 to 20 carbon atoms in which alkyl group not-adjacent any methylene group (—$CH_2$—) may be replaced by oxygen atom, and any hydrogen atom in the alkyl group may be replaced by a halogen atom; $A_1$, $A_2$ and $A_3$ each independently represent trans-1,4-cyclohexylene, dioxane-2,5-diyl, tetrahydropyran-2,5-diyl, 1-silacyclohexane-1,4-diyl, or 4-silacyclohexane-1,4-diyl, or 1,4-phenylene in which one or more hydrogen atoms may be replaced by fluorine atom; $Z_1$, $Z_2$ and $Z_3$ each independently represent —$(CH_2)_2$—, —$(CH_2)_4$—, —$CH_2O$—, —$(CH_2)_3O$— or single bond; m and n are independently 0 or 1 provided that when both m and n are 0, and $A_2$ represents 1,4-phenylene, then at least one hydrogen atom on ring $A_2$ is replaced by fluorine atom; and any atom which constitutes the compound may be replaced by its isotope, have expected properties, leading to the accomplishment of the present invention.

Also, the present invention has the following aspects:
[2] The 3,3'-difluorobiphenyl derivative recited in aspect [1] above wherein both m and n are 0.
[3] The 3,3'-difluorobiphenyl derivative recited in aspect [1] above wherein either m or n is 1.
[4] The 3,3'-difluorobiphenyl derivative recited in aspect [2] above wherein $A_2$ is trans-1,4-cyclohexylene.
[5] The 3,3'-difluorobiphenyl derivative recited in aspect [2] above wherein $A_2$ is dioxane-2,5-diyl, tetrahydropyran-2,5-diyl, 1-silacyclohexane-1,4-diyl, or 4-silacyclohexane-1,4-diyl.

[6] The 3,3'-difluorobiphenyl derivative recited in aspect [2] above wherein $A_2$ is 1,4-phenylene in which at least one hydrogen atom is replaced by fluorine atom.

[7] A liquid crystal composition comprising at least one derivative recited in any one of aspects [1] to [6] above.

[8] A liquid crystal composition comprising, as a first component, at least one derivative recited in any one of aspects [1] to [6] above, and comprising, as a second component, at least one compound selected from the group consisting of the compounds expressed by any one of the general formulas (2), (3) and (4)

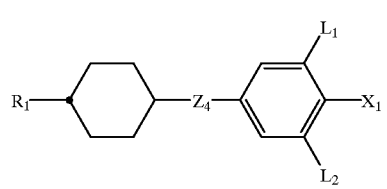
(2)

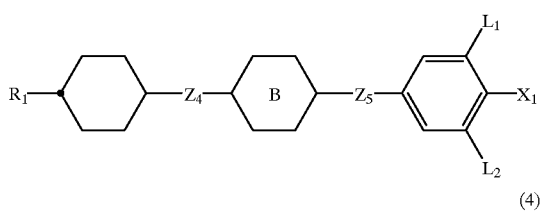
(3)

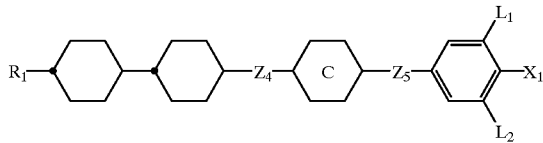
(4)

wherein $R_1$ represents an alkyl group having 1 to 10 carbon atoms in which alkyl group not-adjacent any methylene group may be replaced by oxygen atom or —CH=CH—, and any hydrogen atom in the alkyl group may be replaced by fluorine atom; $x_1$ represents fluorine atom, chlorine atom, —OCF$_3$, —OCF$_2$H, —CF$_3$, —CF$_2$H, —CFH$_2$, —OCF$_2$CF$_2$H or —OCF$_2$CFHCF$_3$; $L_1$ and $L_2$ each independently represent hydrogen atom or fluorine atom; $Z_4$ and $Z_5$ each independently represent —(CH$_2$)$_2$—, —(CH$_2$)$_4$—, —COO—, —CF$_2$O—, —OCF$_2$—, —CH=CH— or single bond; ring B represents trans-1,4-cyclohexylene or 1,3-dioxane-2,5-diyl, or 1,4-phenylene in which hydrogen atom may be replaced by fluorine atom; ring C represents trans-1,4-cyclohexylene, or 1,4-phenylene in which hydrogen atom may be replaced by fluorine atom; and an atom which constitutes these compounds may be replaced by its isotope.

[9] A liquid crystal composition comprising, as a first component, at least one derivative recited in any one of aspects [1] to [6] above, and comprising, as a second component, at least one compound selected from the group consisting of the compounds expressed by the general formula (5) or (6)

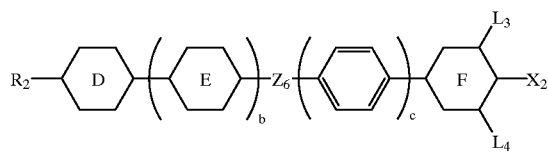
(5)

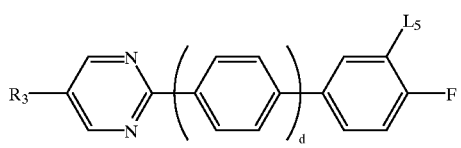
(6)

wherein $R_2$ and $R_3$ each independently represent an alkyl group having 1 to 10 carbon atoms in which alkyl group not-adjacent any methylene group may be replaced by oxygen atom or —CH=CH—, and any hydrogen atom in the alkyl group may be replaced by fluorine atom; $X_2$ represents —CN or —C≡C—CN; ring D represents trans-1,4-cyclohexylene, 1,4-phenylene, 1,3-dioxane-2,5-diyl or pyrimidine-2,5-diyl; ring E represents trans-1,4-cyclohexylene or pyrimidine-2,5-diyl, or 1,4-phenylene in which hydrogen atom may be replaced by fluorine atom; ring F represents trans-1,4-cyclohexylene or phenylene; $Z_6$ represents —(CH$_2$)$_2$—, —COO— or single bond; $L_3$, $L_4$, and $L_5$ each independently represent hydrogen atom or fluorine atom; b, c and d are independently 0 or 1; and an atom which constitutes these compounds may be replaced by its isotope.

[10] A liquid crystal composition comprising, as a first component, at least one derivative recited in any one of aspects [1] to [6] above, comprising, as a second component, at least one compound selected from the group consisting of the compounds expressed by any one of the general formulas (2), (3) and (4) described above, and comprising, as a third component, at least one compound selected from the group consisting of the compounds expressed by any one of the general formulas (7), (8) and (9)

(7)

(8)

(9)

wherein $R_4$ and $R_5$ each independently represent an alkyl group having 1 to 10 carbon atoms in which alkyl group not-adjacent any methylene group may be replaced by oxygen atom or —CH=CH—, and any hydrogen atom in the alkyl group may be replaced by fluorine atom; ring G, ring I and ring J each independently represent trans-1,4-cyclohexylene or pyrimidine-2,5-diyl, or 1,4-phenylene in which hydrogen atom may be replaced by fluorine atom; $Z_7$ and $Z_8$ each independently represent —C≡C—, —COO—, —(CH$_2$)$_2$—, —CH=CH— or single bond; and an atom which constitutes these compounds may be replaced by its isotope.

[11] A liquid crystal composition comprising, as a first component, at least one derivative recited in any one of aspects [1] to [6] above, comprising, as a second component, at least one compound selected from the group consisting of the compounds expressed by the general formula (5) or (6) described above, and comprising, as a third compound, at least one compound selected from the group consisting of the compounds expressed by any one of the general formulas (7), (8) and (9) described above.

[12] A liquid crystal composition comprising, as a first component, at least one derivative recited in any one of aspects [1] to [6] above, and comprising, as a second component, at least one compound selected from the group consisting of the compounds expressed by any one of the general formulas (10), (11) and (12)

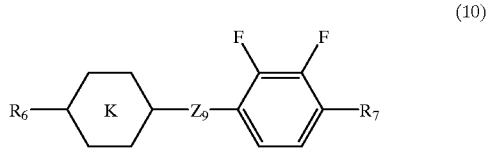

(10)

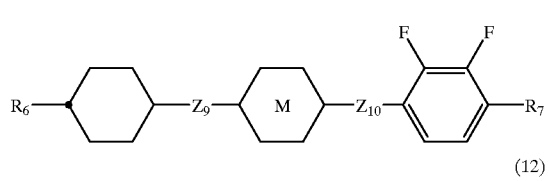

(11)

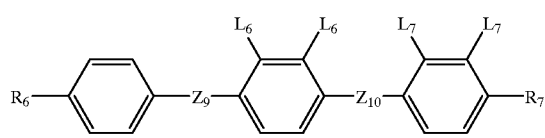

(12)

wherein $R_6$ and $R_7$ each independently represent an alkyl group having 1 to 10 carbon atoms in which alkyl group not-adjacent any methylene group may be replaced by oxygen atom or —CH=CH—, and any hydrogen atom in the alkyl group may be replaced by fluorine atom; ring K and ring M each independently represent trans-1,4-cyclohexylene or 1,4-phenylene; $L_6$ and $L_7$ each independently represent hydrogen atom or fluorine atom but in no case represent $L_6$ and $L_7$ simultaneously hydrogen atom; $Z_9$ and $Z_{10}$ each independently represent —(CH$_2$)$_2$—, —COO— or single bond; and an atom which constitutes these compounds may be replaced by its isotope.

[13] A liquid crystal composition comprising, as a first component, at least one derivative recited in any one of aspects [1] to [6] above, comprising, as a second component, at least one compound selected from the group consisting of the compounds expressed by any one of the general formulas (7), (8) and (9) described above, and comprising, as a third component, at least one compound selected from the group consisting of the compounds expressed by any one of the general formulas (10), (11) and (12) described above.

[14] A liquid crystal composition comprising, as a first component, at least one derivative recited in any one of aspects [1] to [6] above, comprising, as a second component, at least one compound selected from the group consisting of the compounds expressed by any one of the general formulas (2), (3) and (4) described above, comprising, as a third component, at least one expressed by the general formula (5) or (6) described above, and comprising, as a fourth component, at least one compound selected from the group consisting of the compounds expressed by any one of the general formulas (7), (8) and (9) described above.

[15] A liquid crystal composition further comprising at least one optically active compound in addition to the liquid crystal composition recited in any one of aspects [7] to [14] above.

[16] A liquid crystal display device fabricated by using a liquid crystal composition recited in any one of aspects [7] to [15] above.

Whereas a part of the compounds expressed by the general formula (1) are formally included in the claims or descriptions; of the prior publication 3) mentioned above, data on physical property values are not described at all in the publication with respect to the compounds of the present invention, specific references to the characteristics of the compounds are not included therein, and thus the publication has not suggested the utility of the compounds of the present invention.

Compounds expressed by the general formula (1) are classified into those of the following formulas (a-1) to (a-153).

In the following formulas, Ra and Rb have the same meaning as described above; B represents 1,4-phenylene group in which one or more hydrogen atoms on the ring may be replaced by fluorine atom; C represents trans-1,4-cyclohexylene; D represents dioxane-2,5-diyl the direction of which is not limited; TP represents tetrahydropyran-2,5-diyl the direction of which is not limited; Si represents 1-silacyclohexane-1,4-diyl or 4-silacyclohexane-1,4-diyl; and BP represent 3,3'-difluorobiphenyl-4,4'-diyl.

| | |
|---|---|
| Ra—B—BP—Rb | (a-1) |
| Ra—C—BP—Rb | (a-2) |
| Ra—D—BP—Rb | (a-3) |
| Ra—TP—BP—Rb | (a-4) |
| Ra—Si—BP—Rb | (a-5) |
| Ra—B—(CH$_2$)$_2$—BP—Rb | (a-6) |
| Ra—C—(CH$_2$)$_2$—BP—Rb | (a-7) |
| Ra—D—(CH$_2$)$_2$—BP—Rb | (a-8) |
| Ra—TP—(CH$_2$)$_2$—BP—Rb | (a-9) |
| Ra—Si—(CH$_2$)$_2$—BP—Rb | (a-10) |
| Ra—B—(CH$_2$)$_4$—BP—Rb | (a-11) |
| Ra—C—(CH$_2$)$_4$—BP—Rb | (a-12) |
| Ra—D—(CH$_2$)$_4$—BP—Rb | (a-13) |
| Ra—TP—(CH$_2$)$_4$—BP—Rb | (a-14) |
| Ra—Si—(CH$_2$)$_4$—BP—Rb | (a-15) |
| Ra—B—CH$_2$O—BP—Rb | (a-16) |
| Ra—C—CH$_2$O—BP—Rb | (a-17) |
| Ra—D—CH$_2$O—BP—Rb | (a-18) |
| Ra—TP—CH$_2$O—BP—Rb | (a-19) |
| Ra—Si—CH$_2$O—BP—Rb | (a-20) |
| Ra—B—OCH$_2$—BP—Rb | (a-21) |
| Ra—C—OCH$_2$—BP—Rb | (a-22) |
| Ra—D—OCH$_2$—BP—Rb | (a-23) |
| Ra—TP—OCH$_2$—BP—Rb | (a-24) |
| Ra—Si—OCH$_2$—BP—Rb | (a-25) |
| Ra—B—(CH$_2$)$_3$O—BP—Rb | (a-26) |
| Ra—C—(CH$_2$)$_3$O—BP—Rb | (a-27) |
| Ra—D—(CH$_2$)$_3$O—BP—Rb | (a-28) |
| Ra—TP—(CH$_2$)$_3$O—BP—Rb | (a-29) |
| Ra—B—O(CH$_2$)$_3$—BP—Rb | (a-30) |
| Ra—C—O(CH$_2$)$_3$—BP—Rb | (a-31) |
| Ra—D—O(CH$_2$)$_3$—BP—Rb | (a-32) |
| Ra—TP—O(CH$_2$)$_3$—BP—Rb | (a-33) |
| Ra—B—B—BP—Rb | (a-34) |
| Ra—B—C—BP—Rb | (a-35) |
| Ra—B—D—BP—Rb | (a-36) |
| Ra—B—TP—BP—Rb | (a-37) |

| | |
|---|---|
| Ra—B—Si—BP—Rb | (a-38) |
| Ra—B—C—BP—Rb | (a-39) |
| Ra—B—D—BP—Rb | (a-40) |
| Ra—B—TP—BP—Rb | (a-41) |
| Ra—C—C—BP—Rb | (a-42) |
| Ra—C—D—BP—Rb | (a-43) |
| Ra—C—TP—BP—Rb | (a-44) |
| Ra—D—C—BP—Rb | (a-45) |
| Ra—TP—C—BP—Rb | (a-46) |
| Ra—C—Si—BP—Rb | (a-47) |
| Ra—Si—C—BP—Rb | (a-48) |
| Ra—B—BP—B—Rb | (a-49) |
| Ra—C—BP—B—Rb | (a-50) |
| Ra—D—BP—B—Rb | (a-51) |
| Ra—TP—BP—B—Rb | (a-52) |
| Ra—C—BP—C—Rb | (a-53) |
| Ra—D—BP—C—Rb | (a-54) |
| Ra—TP—BP—C—Rb | (a-55) |
| Ra—Si—BP—C—Rb | (a-56) |
| Ra—B—B—(CH$_2$)$_2$—BP—Rb | (a-57) |
| Ra—C—B—(CH$_2$)$_2$—BP—Rb | (a-58) |
| Ra—D—B—(CH$_2$)$_2$—BP—Rb | (a-59) |
| Ra—TP—B—(CH$_2$)$_2$—BP—Rb | (a-60) |
| Ra—Si—B—(CH$_2$)$_2$—BP—Rb | (a-61) |
| Ra—B—C—(CH$_2$)$_2$—BP—Rb | (a-62) |
| Ra—B—D—(CH$_2$)$_2$—BP—Rb | (a-63) |
| Ra—B—tp—(CH$_2$)$_2$—BP—Rb | (a-64) |
| Ra—C—C—(CH$_2$)$_2$—BP—Rb | (a-65) |
| Ra—C—D—(CH$_2$)$_2$—BP—Rb | (a-66) |
| Ra—C—TP—(CH$_2$)$_2$—BP—Rb | (a-67) |
| Ra—D—C—(CH$_2$)$_2$—BP—Rb | (a-68) |
| Ra—TP—C—(CH$_2$)$_2$—BP—Rb | (a-69) |
| Ra—C—Si—(CH$_2$)$_2$—BP—Rb | (a-70) |
| Ra—Si—C—(CH$_2$)$_2$—BP—Rb | (a-71) |
| Ra—B—B—(CH$_2$)$_4$—BP—Rb | (a-72) |
| Ra—C—B—(CH$_2$)$_4$—BP—Rb | (a-73) |
| Ra—B—C—(CH$_2$)$_4$—BP—Rb | (a-74) |
| Ra—C—C—(CH$_2$)$_4$—BP—Rb | (a-75) |
| Ra—B—B—CH$_2$O—BP—Rb | (a-76) |
| Ra—C—B—CH$_2$O—BP—Rb | (a-77) |
| Ra—D—B—CH$_2$O—BP—Rb | (a-78) |
| Ra—TP—B—CH$_2$O—BP—Rb | (a-79) |
| Ra—Si—B—CH$_2$O—BP—Rb | (a-80) |
| Ra—B—C—CH$_2$O—BP—Rb | (a-81) |
| Ra—B—D—CH$_2$O—BP—Rb | (a-82) |
| Ra—B—TP—CH$_2$O—BP—Rb | (a-83) |
| Ra—C—C—CH$_2$O—BP—Rb | (a-84) |
| Ra—C—D—CH$_2$O—BP—Rb | (a-85) |
| Ra—C—TP—CH$_2$O—BP—Rb | (a-86) |
| Ra—D—C—CH$_2$O—BP—Rb | (a-87) |
| Ra—TP—C—CH$_2$O—BP—Rb | (a-88) |
| Ra—C—Si—CH$_2$O—BP—Rb | (a-89) |
| Ra—Si—C—CH$_2$O—BP—Rb | (a-90) |
| Ra—B—B—OCH$_2$—BP—Rb | (a-91) |
| Ra—C—B—OCH$_2$—BP—Rb | (a-92) |
| Ra—D—B—OCH$_2$—BP—Rb | (a-93) |
| Ra—TP—B—OCH$_2$—BP—Rb | (a-94) |
| Ra—B—C—OCH$_2$—BP—Rb | (a-95) |
| Ra—B—D—OCH$_2$—BP—Rb | (a-96) |
| Ra—B—TP—OCH$_2$—BP—Rb | (a-97) |
| Ra—C—C—OCH$_2$—BP—Rb | (a-98) |
| Ra—C—D—OCH$_2$—BP—Rb | (a-99) |
| Ra—C—TP—OCH$_2$—BP—Rb | (a-100) |
| Ra—D—C—OCH$_2$—BP—Rb | (a-101) |
| Ra—TP—C—OCH$_2$—BP—Rb | (a-102) |
| Ra—B—(CH$_2$)$_2$—B—BP—Rb | (a-103) |
| Ra—C—(CH$_2$)$_2$—B—BP—Rb | (a-104) |
| Ra—D—(CH$_2$)$_2$—B—BP—Rb | (a-105) |
| Ra—TP—(CH$_2$)$_2$—B—BP—Rb | (a-106) |
| Ra—Si—(CH$_2$)$_2$—B—BP—Rb | (a-107) |
| Ra—B—(CH$_2$)$_2$—C—BP—Rb | (a-108) |
| Ra—B—(CH$_2$)$_2$—D—BP—Rb | (a-109) |
| Ra—B—(CH$_2$)$_2$—TP—BP—Rb | (a-110) |
| Ra—C—(CH$_2$)$_2$—C—BP—Rb | (a-111) |
| Ra—C—(CH$_2$)$_2$—D—BP—Rb | (a-112) |
| Ra—C—(CH$_2$)$_2$—TP—BP—Rb | (a-113) |
| Ra—D—(CH$_2$)$_2$—C—BP—Rb | (a-114) |
| Ra—TP—(CH$_2$)$_2$—C—BP—Rb | (a-115) |
| Ra—C—(CH$_2$)$_2$—Si—BP—Rb | (a-116) |
| Ra—Si—(CH$_2$)$_2$—C—BP—Rb | (a-117) |
| Ra—B—(CH$_2$)$_4$—B—BP—Rb | (a-118) |
| Ra—C—(CH$_2$)$_4$—B—BP—Rb | (a-119) |
| Ra—B—(CH$_2$)$_4$—C—BP—Rb | (a-120) |
| Ra—C—(CH$_2$)$_4$—C—BP—Rb | (a-121) |
| Ra—B—CH$_2$O—B—BP—Rb | (a-122) |
| Ra—C—CH$_2$O—B—BP—Rb | (a-123) |
| Ra—D—CH$_2$O—B—BP—Rb | (a-124) |
| Ra—TP—CH$_2$O—B—BP—Rb | (a-125) |
| Ra—Si—CH$_2$O—B—BP—Rb | (a-126) |
| Ra—B—CH$_2$O—C—BP—Rb | (a-127) |
| Ra—C—CH$_2$O—C—BP—Rb | (a-128) |
| Ra—C—CH$_2$O—D—BP—Rb | (a-129) |
| Ra—C—CH$_2$O—TP—BP—Rb | (a-130) |
| Ra—D—CH$_2$O—C—BP—Rb | (a-131) |
| Ra—TP—CH$_2$O—C—BP—Rb | (a-132) |
| Ra—Si—CH$_2$O—C—BP—Rb | (a-133) |
| Ra—B—OCH$_2$—B—BP—Rb | (a-134) |
| Ra—C—OCH$_2$—B—BP—Rb | (a-135) |
| Ra—D—OCH$_2$—B—BP—Rb | (a-136) |
| Ra—TP—OCH$_2$—B—BP—Rb | (a-137) |
| Ra—B—OCH$_2$—C—BP—Rb | (a-138) |
| Ra—B—OCH$_2$—D—BP—Rb | (a-139) |
| Ra—B—OCH$_2$—TP—BP—Rb | (a-140) |
| Ra—C—OCH$_2$—C—BP—Rb | (a-141) |
| Ra—C—OCH$_2$—D—BP—Rb | (a-142) |
| Ra—C—OCH$_2$—TP—BP—Rb | (a-143) |
| Ra—D—OCH$_2$—C—BP—Rb | (a-144) |
| Ra—TP—OCH$_2$—C—BP—Rb | (a-145) |
| Ra—B—(CH$_2$)$_3$O—B—BP—Rb | (a-146) |
| Ra—C—(CH$_2$)$_3$O—B—BP—Rb | (a-147) |
| Ra—B—(CH$_2$)$_3$O—C—BP—Rb | (a-148) |
| Ra—C—(CH$_2$)$_3$O—C—BP—Rb | (a-149) |
| Ra—B—O(CH$_2$)$_3$—B—BP—Rb | (a-150) |
| Ra—C—O(CH$_2$)$_3$—B—BP—Rb | (a-151) |
| Ra—B—O(CH$_2$)$_3$—C—BP—Rb | (a-152) |
| Ra—C—O(CH$_2$)$_3$—C—BP—Rb | (a-153) |

Any compounds expressed by one of the formulas (a-1) to (a-153) exhibit preferable characteristics. Among the group of the compounds of the formula (a-1) to (a-153), however, compounds of the formulas (a-1) to (a-10), (a-16) to (a-22), (a-26) to (a-29), (a-34) to (a-38), (a-42) to (a-53), (a-56) to (a-61), (a-65) to (a-71), (a-76) to (a-80), (a-84) to (a-91), (a-103) to (a-107), (a-111) to (a-117), (a-122) to (a-126), (a-128), (a-133), (a-134), and (a-138) to (a-140) can be mentioned as ones exhibiting especially preferable characteristics.

While Ra and Rb in the formulas represent a straight chain or branched alkyl groups having 1 to 20 carbon atoms, as the straight chain alkyl group, methyl, ethyl, propyl, butyl, pentyl, hexyl, heptyl, decyl, pentadecyl and icosyl, and as the branched alkyl group, isopropyl, sec-butyl, tert-butyl, 2-methylbutyl, isopentyl, isohexyl, 3-ethyloctyl, 3,8-dimethyltetradecyl and 5-ethyl-5-methylnonadecyl can specifically be mentioned as examples, respectively.

The branched alkyl group may be those of exhibiting optical activity, and such compounds are useful as chiral dopant.

Not-adjacent any methylene group in these alkyl groups may be replaced by oxygen atom, and specifically, alkoxy groups such as methoxy, ethoxy, propoxy, butoxy, pentyloxy, and nonyloxy, and alkoxyalkyl groups such as methoxymethyl, methoxyethyl, methoxypropyl, methoxybutyl, methoxypentyl, methoxyoctyl, ethoxymethyl, ethoxyethyl, ethoxypropyl, ethoxyhexyl, propoxymethyl, propoxyethyl, propoxypropyl, propoxypentyl, butoxymethyl, butoxyethyl, butoxybutyl, pentyloxymethyl, pentyloxybutyl, hexyloxymethyl, hexyloxyethyl, hexyloxypropyl, heptyloxymethyl and octyloxymethyl can be mentioned as examples, respectively.

Hydrogen atom in these groups may be replaced by a halogen atom, and specifically, halogen substituted alkyl groups such as fluoromethyl, difluoromethyl, trifluoromethyl, 2-fluoroethyl, 1,2-difluoroethyl, 1,1,2,2-tetrafluoroethyl, 2-bromo-1,2-difluoroethyl, 3-fluoropropyl, 1,2,3,3-tetrafluoropropyl, 1,1,3,3,3-pentafluoropropyl, 1,1,2,3,3,3-hexafluoropropyl, 3-fluorobutyl, 4-fluorobutyl, 1,1,2,4-tetrafluorobutyl, 3-fluoropentyl, 5-fluoropentyl, 2,3,3,4,5-pentafluoropentyl, 6-fluorohexyl, 2,3,4,6-tetrafluorohexyl, 7-fluoroheptyl and 8,8-difluorooctyl, and halogen substituted alkoxy groups such as difluoromethoxy, trifluoromethoxy, 1,1-difluoroethoxy, 2,2-difluoroethoxy, 2,2,2-trifluoroethoxy, 1,1,2,2-tetrafluoroethoxy, perfluoroethoxy, 1,1,2,3,3,3-hexafluoropropoxy, and perfluoropropoxy can be mentioned as examples. However, straight chain alkyl groups, branched alkyl groups, straight chain alkoxy groups, branched alkoxy groups, straight chain halogen substituted alkyl groups, and straight chain halogen substituted alkoxy groups are preferable, and straight chain alkyl groups, branched alkyl groups, straight chain alkoxy groups, and branched alkoxy groups are more desirable.

$A_1$, $A_2$ and $A_3$ represent trans-1,4-cyclohexylene, 1,3-dioxane-2,5-diyl, 1,4-dioxane-2,5-diyl, tetrahydropyran-2,5-diyl, 1-silacyclohexane-1,4-diyl, or 4-silacyclohexane-1,4-diyl, or 1,4-phenyl in which one or more hydrogen atoms may be replaced by fluorine atom. However, trans-1,4-cyclohexylene, 1-silacyclohexane-1,4-diyl or 4-silacyclohexane-1,4-diyl, or 1,4-phenylene in which one or more hydrogen atoms may be replaced by fluorine atom are preferable from the viewpoint of viscosity and others, and the 1-silacyclohexane-1,4-diyl and 4-silacyclohexane-1,4-diyl are more desirably trans form.

While $Z_1$, $Z_2$ and $Z_3$ are selected from the group consisting of —$(CH_2)_2$—, —$(CH_2)_4$—, —$CH_2O$—, —$(CH_2)_3O$— and single bond, —$(CH_2)_2$—, —$CH_2O$— and single bond are preferable from the viewpoint of viscosity and others.

While 3,3-difluorobiphenyl derivatives of the present invention expressed by the general formula (1) can be produced by known general methods of organic synthesis, they can conveniently be produced, for instance, by the following methods:

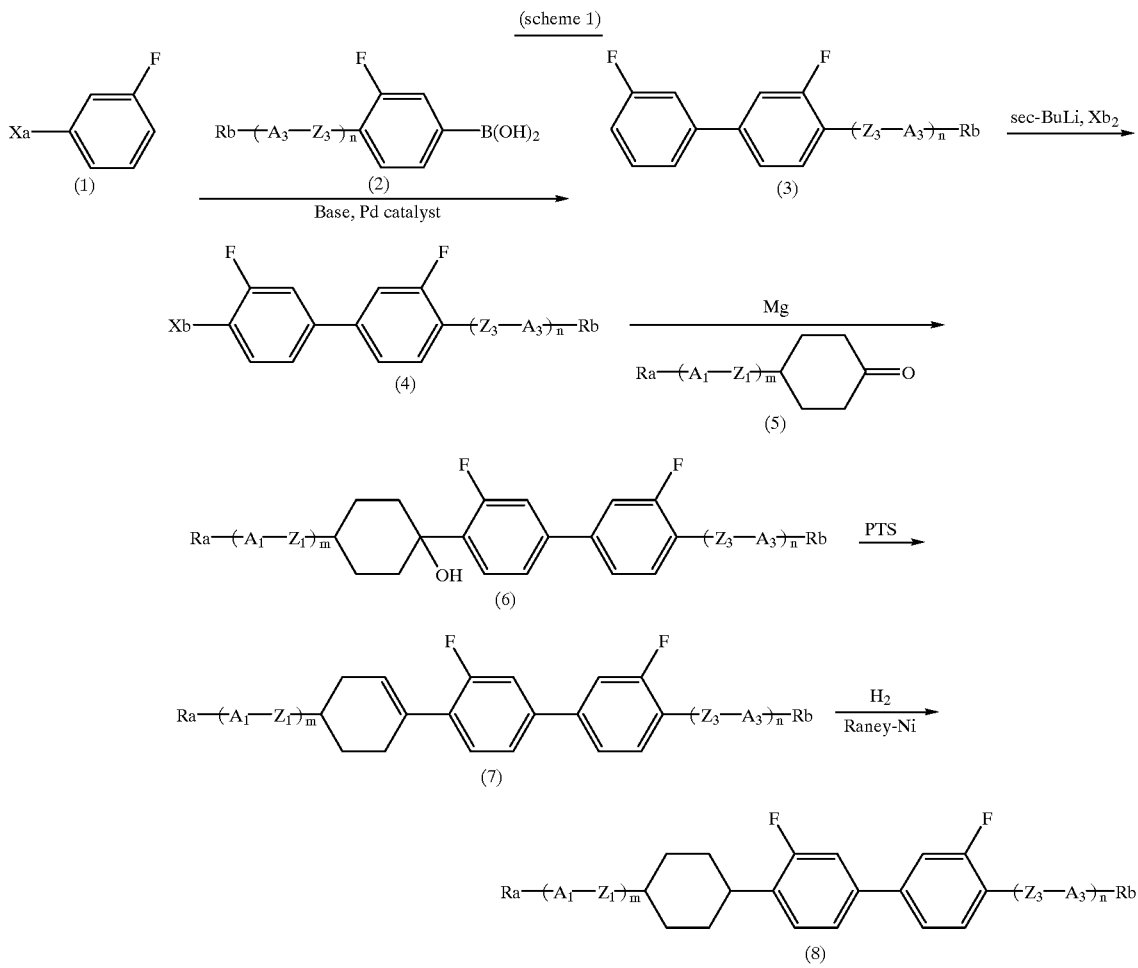

(scheme 1)

(scheme 2)

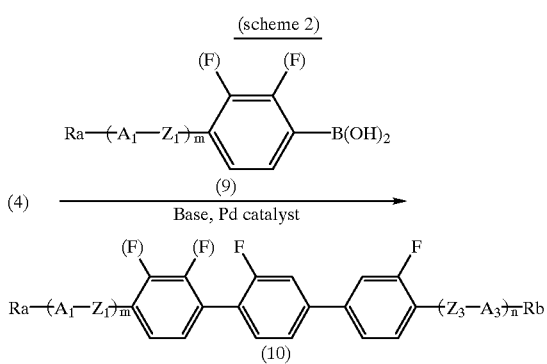

(scheme 3)

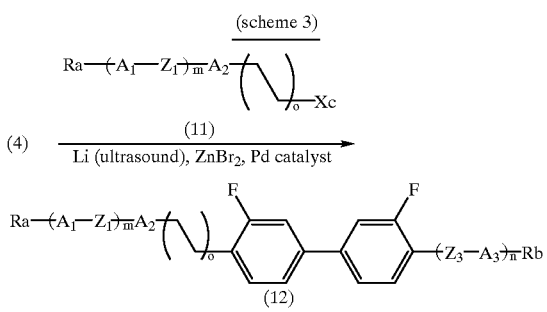

pound (4). A Grignard reagent is prepared from Compound (4) and magnesium (or a lithium compound is prepared from compound (4) and n-butyl lithium), and the Grignard reagent is reacted with compound (5) to obtain compound (6). Subsequently, the compound (6) is subjected to a dehydration reaction in the presence of an acid catalyst such as p-toluenesulfonic acid (PTS) and then hydrogenated in the presence of a catalyst such as Raney-Ni and Pd—C to produce the compound (8) of the present invention.

As shown in scheme 2, compound (10) which is another example of the compounds of the present invention can be produced by the same method as in scheme 1 with the exception that compound (4) and compound (9) are used in place of compound (1) and compound (2), respectively.

As shown in scheme 3, compound (12) of the present invention can be produced by lithiating compound (11), reacting with a zinc compound such as $ZnBr_2$, and then reacting with compound (4) (Hayashi et al., Journal of the American Chemical Society, 106, 158 (1984)).

As shown in scheme 4, compound (15) is obtained by forming compound (14) by the same method as in scheme 1 with the exception that compound (13) is used in place of compound (1), and then deprotecting compound (14). Subsequently, compound (15) and compound (16) are reacted in a solvent such as dimethyl sulfoxide, dimethyl formamide, 1,2-dimethoxyethane, tetrahydrofuran, hexamethylphosphoric triamide and toluene in the presence of a base such as sodium amide (J. B. Wright et al., Journal of the American Chemical Society, 70, 3098 (1948)), potassium carbonate (W. T. Olson et al., Journal of the American Chemical Society, 69, 2451 (1947)), triethylamine (R. L.

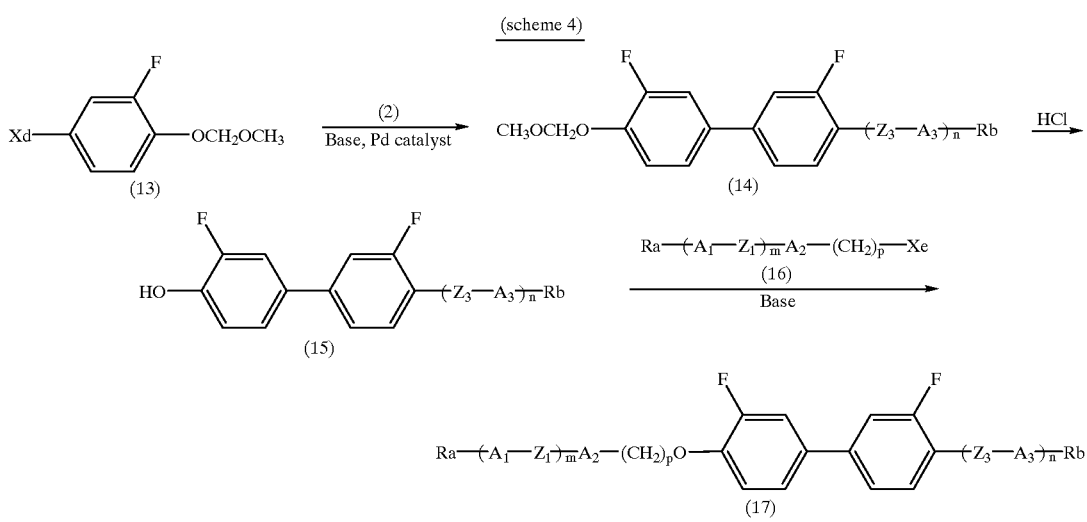

wherein Ra, Rb, $A_1$ to $A_3$, $Z_1$, $Z_3$, m and n have the same meaning as described above, Xa to Xe represent a halogen atom, o is 1 or 2, p is 1 or 3, and the hydrogen atom on benzene ring may be replaced by the atom shown in the parenthesis.

That is, as shown in scheme 1, after compound (1) and compound (2) are reacted (M. Hird et al., Liquid Crystals, 18 (1), 1 (1995)) in a mixed solvent of toluene, xylene or the like, an alcohol such as ethanol and water in the presence of a base such as $K_2CO_3$ and $Na_2CO_3$, and a catalyst such as palladium carried on carbon (Pd—C), $Pd(PPh_3)_4$, $PdCl_2(PPh_3)_2$ to form compound (3), it is reacted with a lithium compound such as sec-butyl lithium and then with a halogen molecule (particularly bromine or iodine) to obtain com- Merker et al., The Journal of Organic Chemistry, 26, 5180 (1961)), sodium hydroxide (C. Wilkins, Synthesis, (1973), 156), potassium hydroxide (J. Rebek et al., The Journal of Organic Chemistry, 44, 1485 (1979)), barium hydroxide (Kawabe et al., The Journal of Organic Chemistry, 37, 4210 (1972)), and sodium hydride (C. J. Stark, Tetrahedron Letters, 22, 2089 (1981) and K. Takai et al., Tetrahedron Letters, 21, 1657 (1980)) to produce compound (17) of the present invention.

Compounds expressed by the general formula (1) wherein —O— is included in Ra and Rb can be produced by the same method.

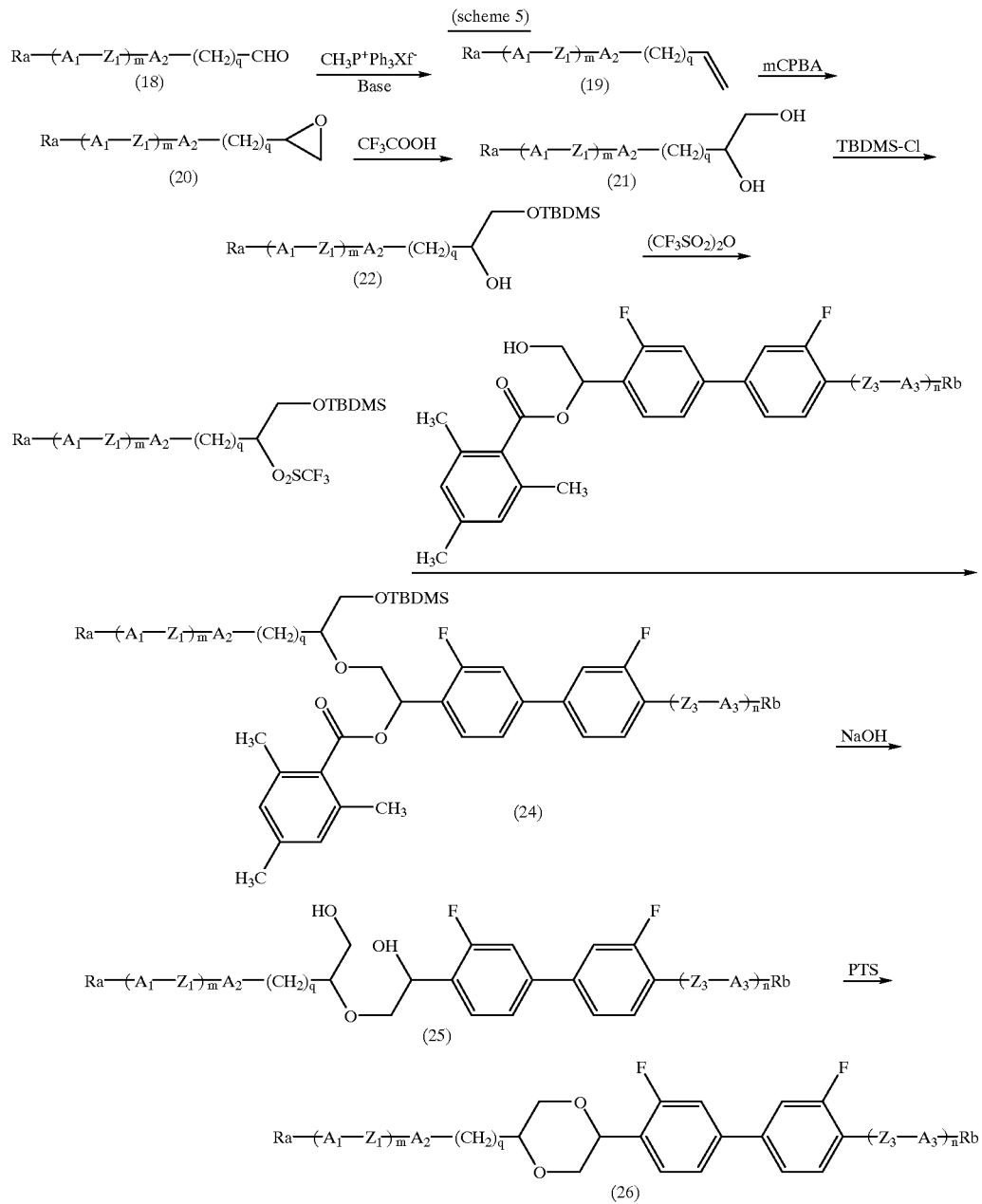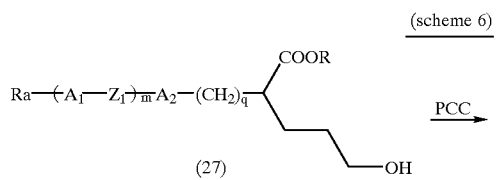

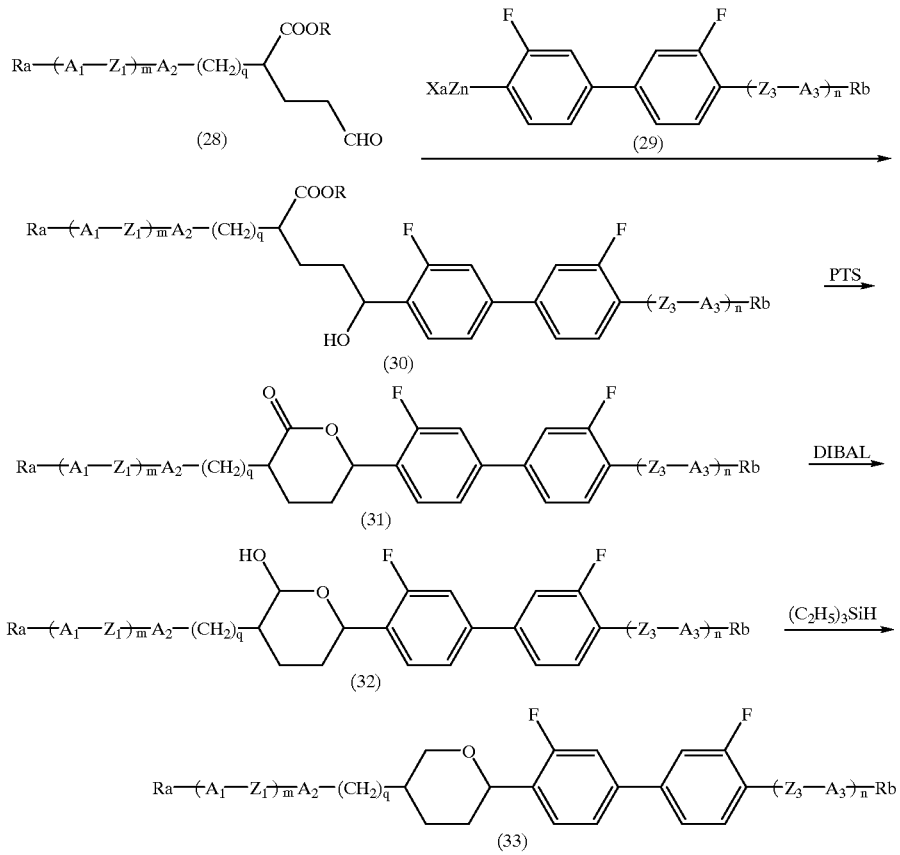

wherein Ra, Rb, $A_1$ to $A_3$, $Z_1$, $Z_3$, m and n have the same meaning as described above, Xa and Xf- represent a halogen atom, q is 2 or 4, and R represents an alkyl group.

As shown in scheme 5, compound (18) and methyltriphenyl-phosphonium halide are subjected to the Wittig reaction (Organic Reactions, Vol. 14, Chapter 3) to form compound (19), and it is converted into compound (20) with a peroxide such as peracetic acid (D. Swern et al., Journal of the American Chemical Society, 68, 1504 (1946)), perbenzoic acid (J. Grigor et al., Journal of the Chemical Society, 2333, (1954)), trifluoroperacetic acid (E. J. Corey et al., Journal of the American Chemical Society, 101, 5841 (1979)), m-chloroperbenzoic acid (mCPBA) (A. G. Hortmann et al., The Journal of Organic Chemistry, 35, 4920 (1970) and M. Sworin et al., Journal of the American Chemical Society, 111, 1815 (1989)).

Subsequently, it is hydrolysed with trifluoroacetic acid (A. C. Cope et al, Journal of the American Chemical Society, 85, 3752 (1963)), trichloroacetic acid (G. Berti et al, Tetrahedron Letters, 3421, (1965)), trinitrobenzenesulfonic acid (M. A. Khuddus et al., Journal of the American Chemical Society, 95, 8393 (1973)) or the like to form compound (21), and then protected with tert-butyldimethylsilyl chloride (TBDMS-Cl) (K. K. Oglivie et al., Tetrahedron Letters, 317 (1973), S. K. Chaudhary et al., Tetrahedron Letters, 99, (1979)) or the like, derived to trifluoromethanesulfonic ester (T. Gramstad et al., Journal of Chemical Society, 4069 (1957)), a sulfonic ester (Ogura et al., Bulletin of the Chemical Society of Japan, 56, 1257 (1983)) or an oxalic ester (E. E. Smissman et al., The Journal of Organic Chemistry, 37, 3944 (1972), and then reacted with compound (23) to form compound (24). Subsequently, it is deprotected (I. J. Bolton et al., Journal of the Chemical society, 2944 (1971)), and subjected to a dehydration reaction in the presence of an acid catalyst such as PTS to produce compound (26) of the present invention.

As shown in scheme 6, compound (27) is oxidized with an oxidizing agent such as pyridinium chlorochromate (PCC) (G. Melvin et al., Journal of the Chemical Society Perkin Transaction, 1, 599 (1981)) and pyridinium dichromate, and then reacted with compound (29) to obtain compound (30). It is dehydrated in the presence of a mineral acid such as hydrochloric acid and sulfuric acid, or an acid catalyst such as PTS (W. J. Johnson et al., Journal of the American Chemical Society, 83, 606 (1961)) to obtain compound (31). Subsequently, it is reduced with a reducing agent such as diisobutyl aluminum hydride (DIBAL) (E. J. Corey et al., Journal of the American Chemical Society, 91, 5675 (1969)) and sodium bis(2-methoxy-ethoxy)aluminum hydride (Tokoroyama et al., Tetrahedron Letters, 36, 3377 (1980)) to obtain compound (32). Besides, the compound (32) can be reduced with a hydrosilane such as triethylsilane (G. A. Kraus et al., Journal of the Chemical Society Chemical Communications, 1568 (1986)) to produce compound (33) of the present invention.

Further, compounds expressed by the general formula (1) having silacyclohexane ring therein can readily be produced by the methods disclosed in Japanese Patent Application laid-open No. Hei 7-70148, Japanese Patent Application laid-open No. Hei 7-112990, Japanese Patent Application laid-open No. Hei 7-173176 or Japanese Patent Application laid-open No. Hei 7-252273.

While dihydroxyborane derivatives (2) and (9) which are starting raw materials can also be produced by known general methods of organic synthesis, they can conveniently be produced by the following method:

(scheme 7)

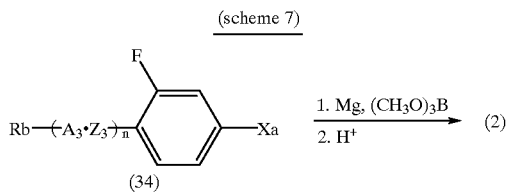

wherein Rb, $A_3$, $Z_3$, n and Xa have the same meaning as described above.

That is, as shown in scheme 7, compound (34), a Grignard reagent prepared from magnesium, and a trialkoxy borane such as trimethoxy borane and triisopropyloxy borane can be reacted and then hydrolysed with hydrochloric acid or the like to produce compound (2).

While the reactions described above are all known in public, it is needless to say that other known reaction can be used when necessary.

Liquid crystalline compounds of the present invention obtained by such methods have an extremely high voltage holding ratio and a low threshold voltage, are considerably small in their dependency on temperature, hardly exhibit smectic phase, and can readily be mixed with various liquid crystal materials and thus are excellent in mutual solubility.

Liquid crystalline compounds of the present invention are sufficiently stable physically and chemically under conditions wherein liquid crystal display devices are ordinarily used, arLd thus are remarkably excellent as component of nematic liquid crystal compositions.

Further, the compounds of the present invention can preferably be used as component even in liquid crystal compositions for TN, STN or TFT.

Among the compounds expressed by the general formula (1), compounds having three six-membered rings exhibit a high phase transition temperature to isotropic phase and a comparatively low viscosity, and compounds having four six-membered rings exhibit an especially high phase transition temperature to isotropic phase and a rather high viscosity. Compounds having cyclohexane ring, dioxane ring, tetrahydropyran ring or silacylcohexane ring in the molecule exhibit a small optical anisotropy value, compounds having cyclohexane ring, silacyclohexane ring or benzene ring exhibit a low viscosity, and compounds having benzene ring exhibit a comparatively large optical anisotropy value.

Further, compounds having the following partial structure exhibit a negative and large dielectric anisotropy value:

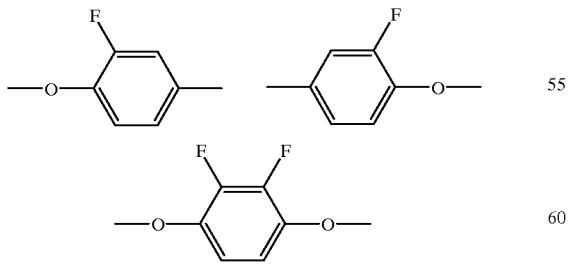

By replacing the hydrogen atom in the ring structure by fluorine atom, it is possible to impart a larger dielectric anisotropy value, and mutual solubility can also be improved at the same time.

Compounds of the present invention in which an atom is replaced by its isotope can also be said to be preferable since they exhibit similar properties.

From these facts, it can be understood that novel liquid crystalline compounds having desired physical properties can be obtained by selecting proper ring, side chain, substituent group, or bonding group.

Liquid crystal compositions of the present invention will be described below. Liquid crystal compositions of the present invention comprise at least one compound expressed by the general formula (1) preferably in the ratio of 0.1 to 99.9% by weight to develop excellent characteristics, and the ratio is more desirably 1 to 50% by weight.

More specifically, liquid crystal compositions provided by the present invention are completed by mixing the compound selected from a group of the compounds expressed by one of the general formulas (2) to (12) depending on the purposes of the liquid crystal compositions, in addition to a first component comprising at least one compound expressed by the general formula (1).

As preferable examples of the compound used in the liquid crystal compositions of the present invention and expressed by one of the general formulas (2) to (4), the following compounds can be mentioned:

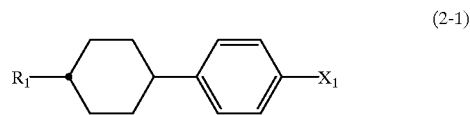

(2-1)

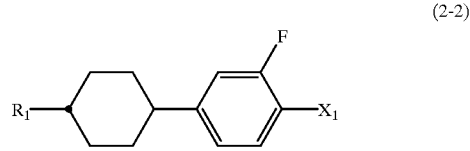

(2-2)

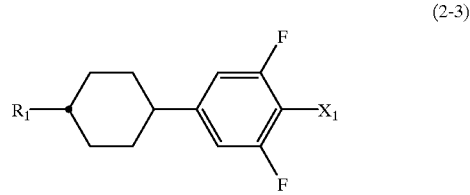

(2-3)

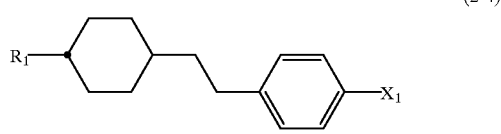

(2-4)

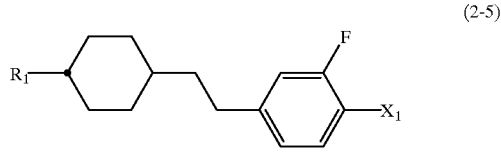

(2-5)

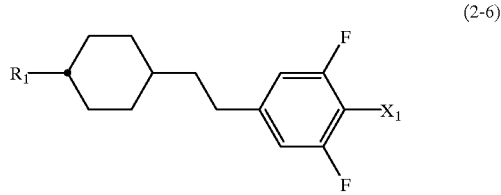

(2-6)

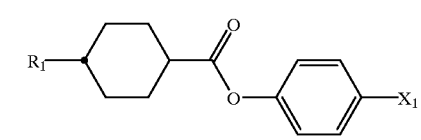
(2-7)
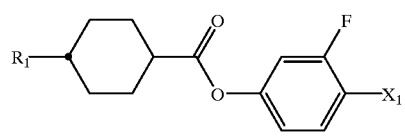
(2-8)
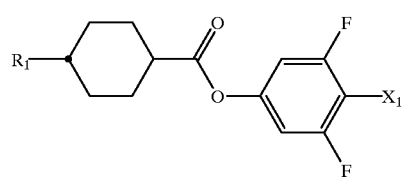
(2-9)
(3-1)
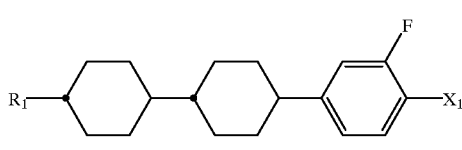
(3-2)
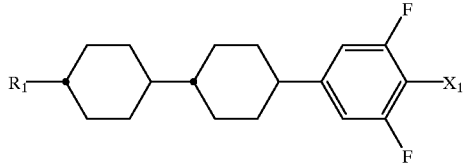
(3-3)
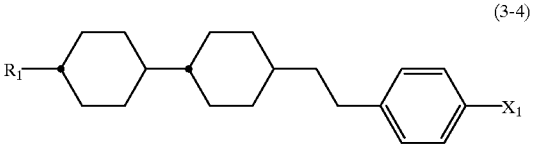
(3-4)
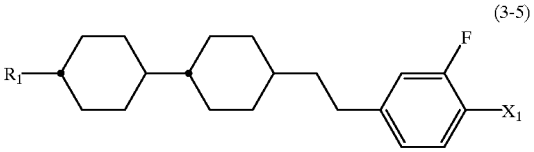
(3-5)
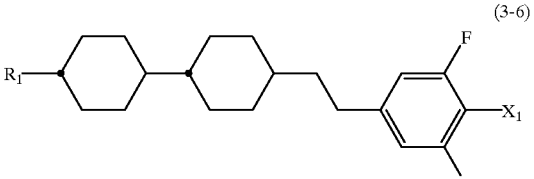
(3-6)
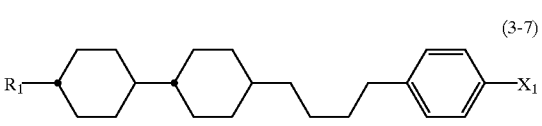
(3-7)
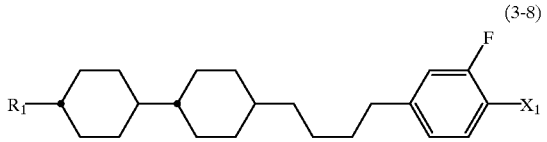
(3-8)
(3-9)
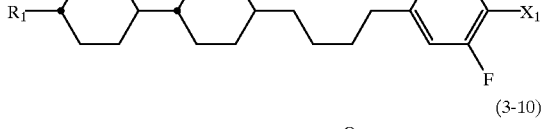
(3-10)
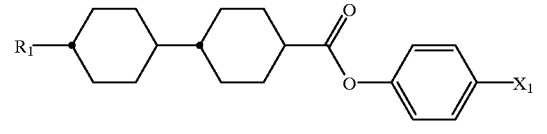
(3-11)
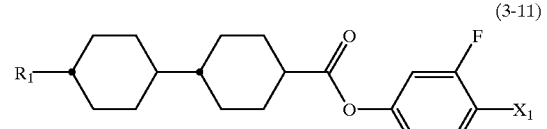
(3-12)
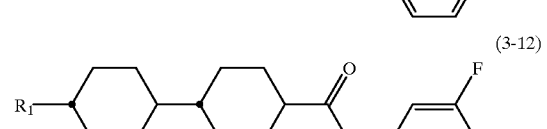
(3-13)
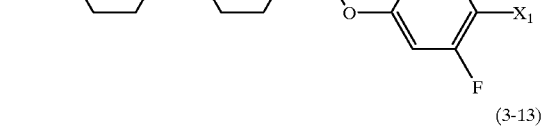
(3-14)
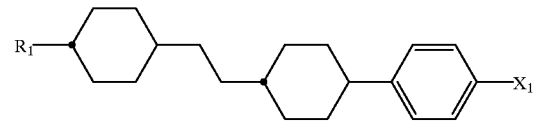
(3-15)
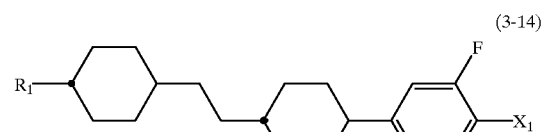
(3-16)
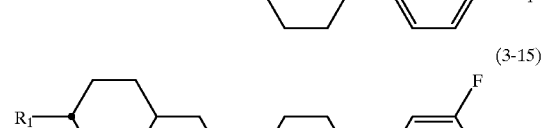
(3-17)

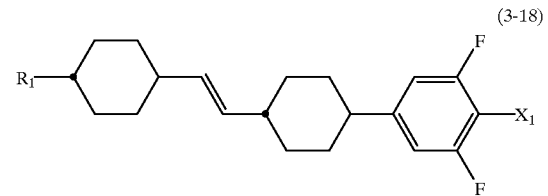
(3-18)
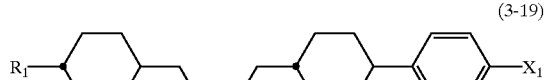
(3-19)
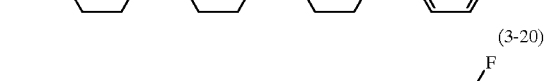
(3-20)
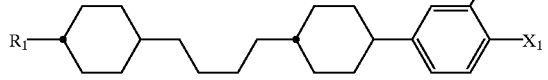
(3-21)
(3-22)
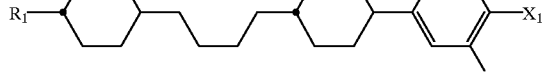
(3-23)
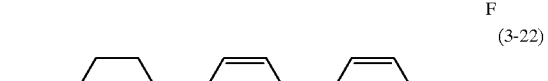
(3-24)
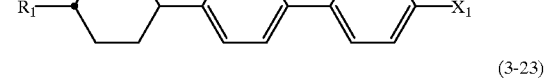
(3-25)
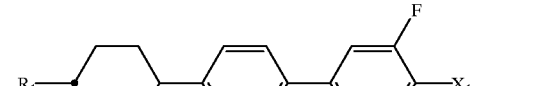
(3-26)
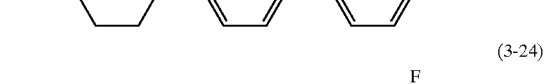
(3-27)
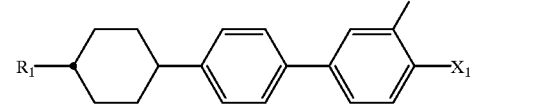
(3-28)
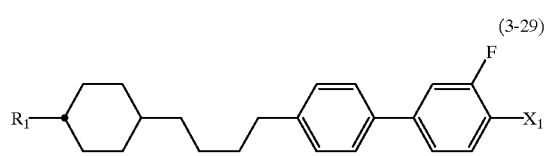
(3-29)
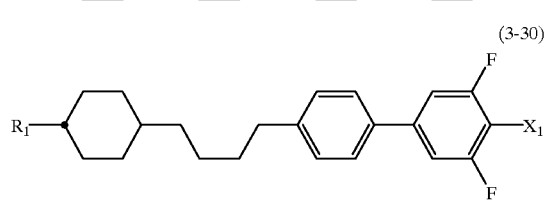
(3-30)
(3-31)
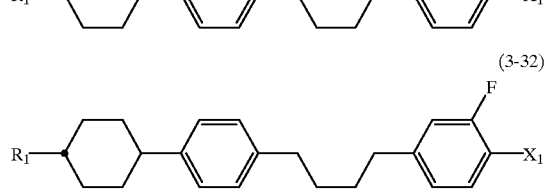
(3-32)
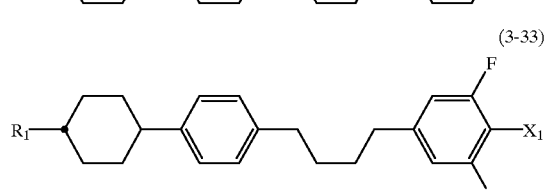
(3-33)
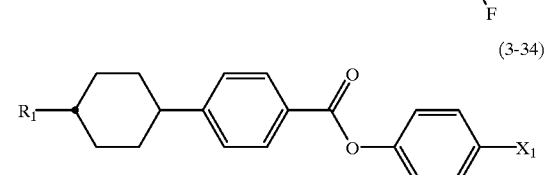
(3-34)
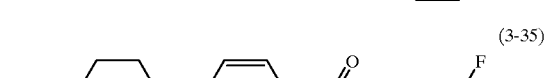
(3-35)
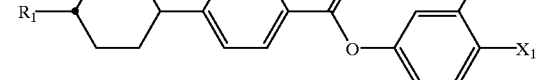
(3-36)
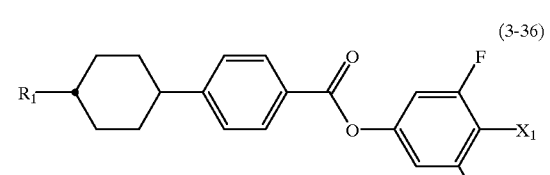
(3-37)
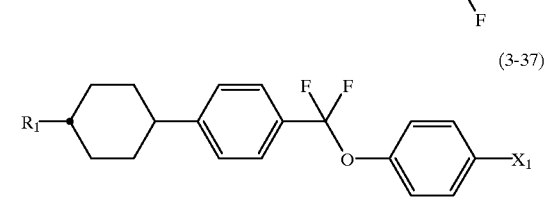
(3-38)

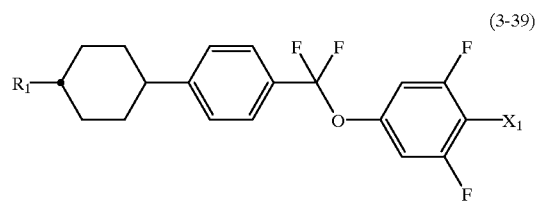
(3-39)
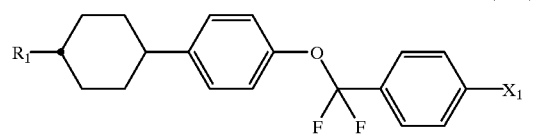
(3-40)
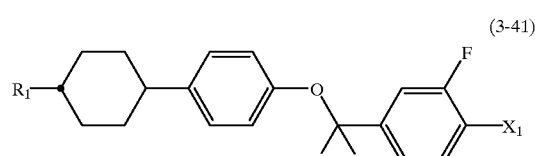
(3-41)
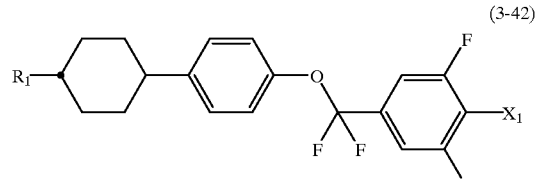
(3-42)
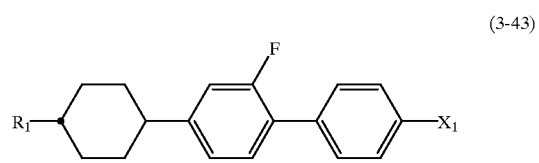
(3-43)
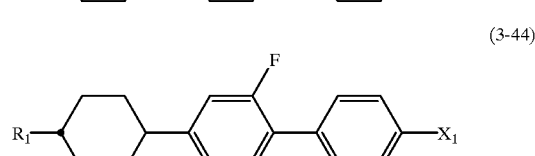
(3-44)
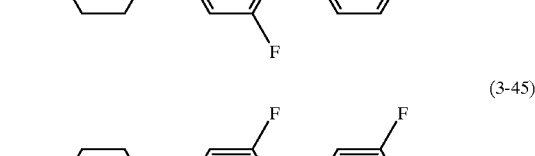
(3-45)
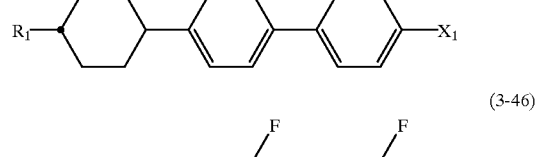
(3-46)
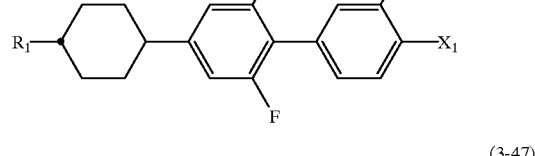
(3-47)
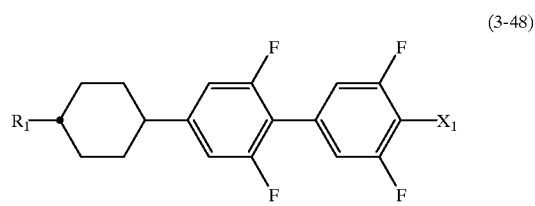
(3-48)
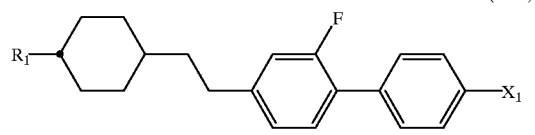
(3-49)
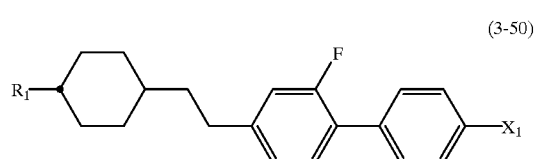
(3-50)
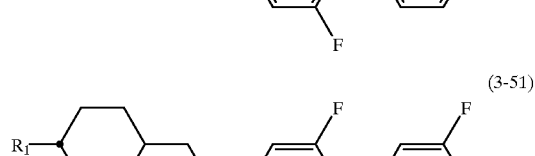
(3-51)
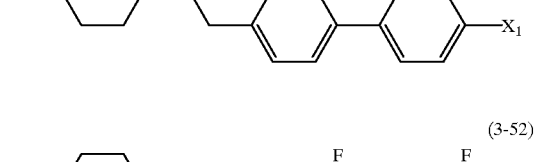
(3-52)
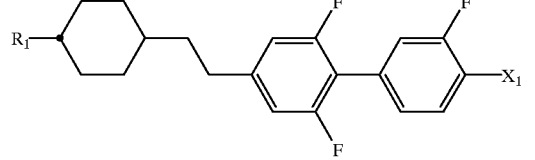
(3-53)
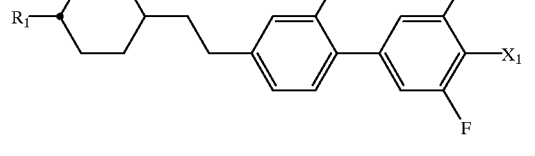
(3-54)
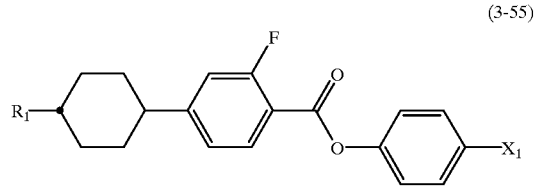
(3-55)

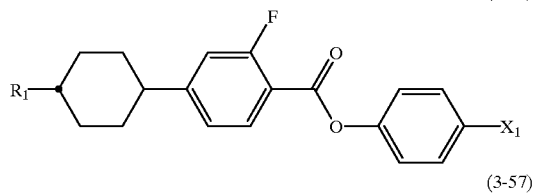
(3-56)
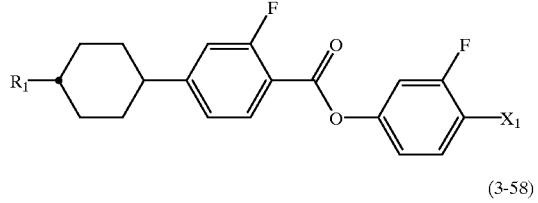
(3-57)
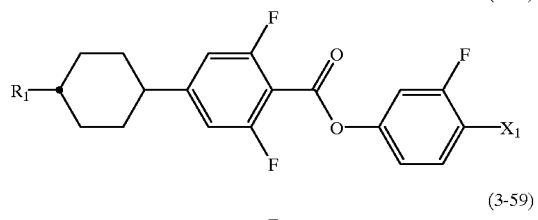
(3-58)
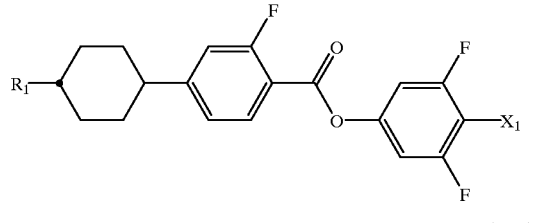
(3-59)
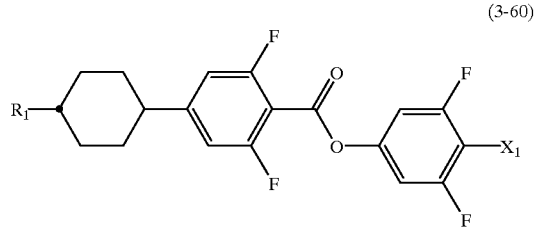
(3-60)
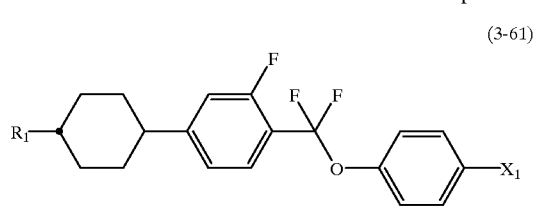
(3-61)
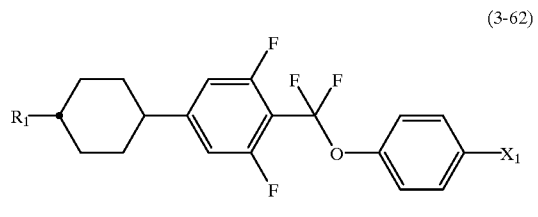
(3-62)
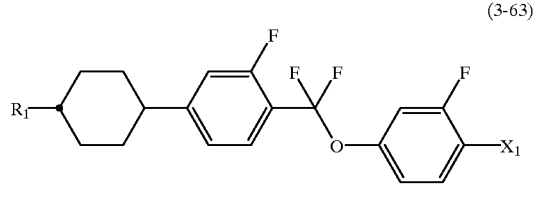
(3-63)
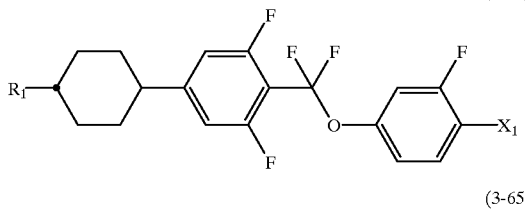
(3-64)
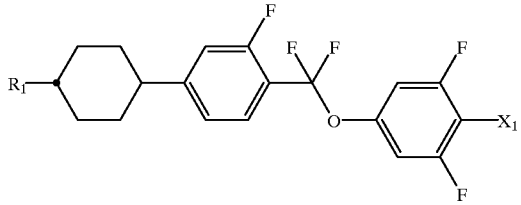
(3-65)
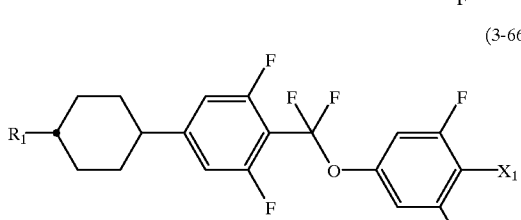
(3-66)
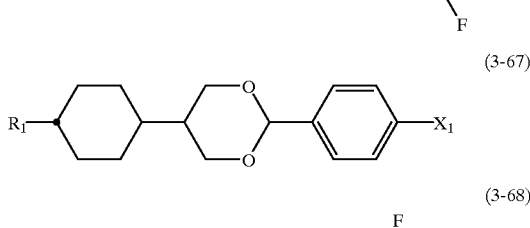
(3-67)
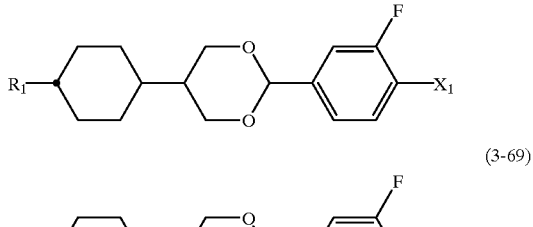
(3-68)
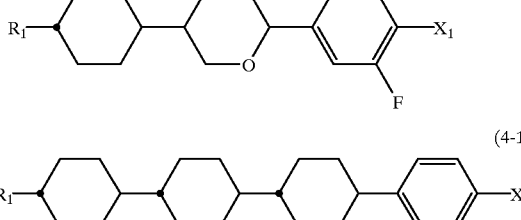
(3-69)
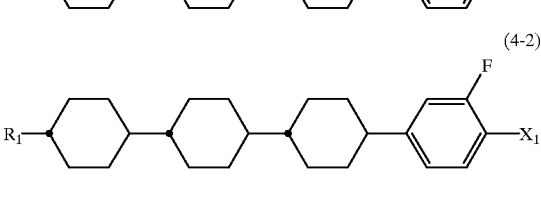
(4-1)
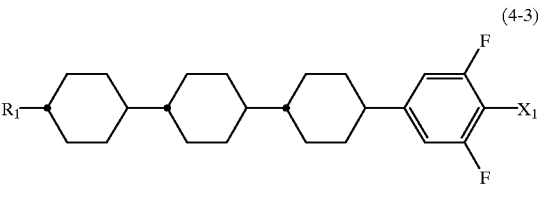
(4-2)
(4-3)

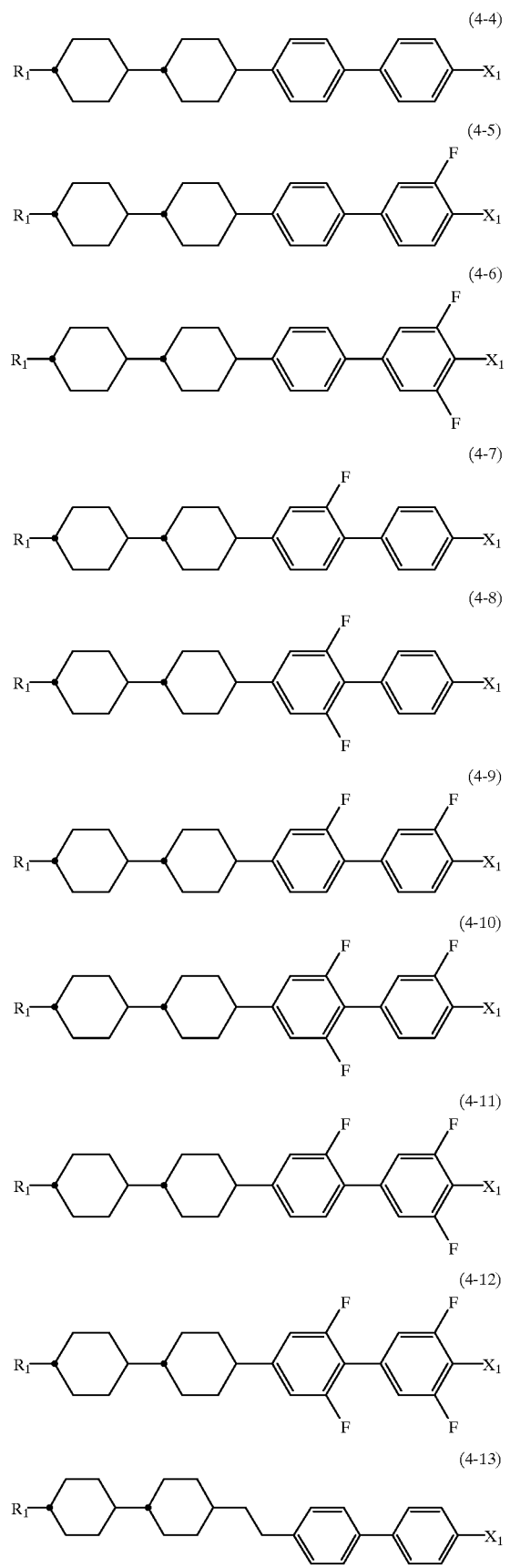
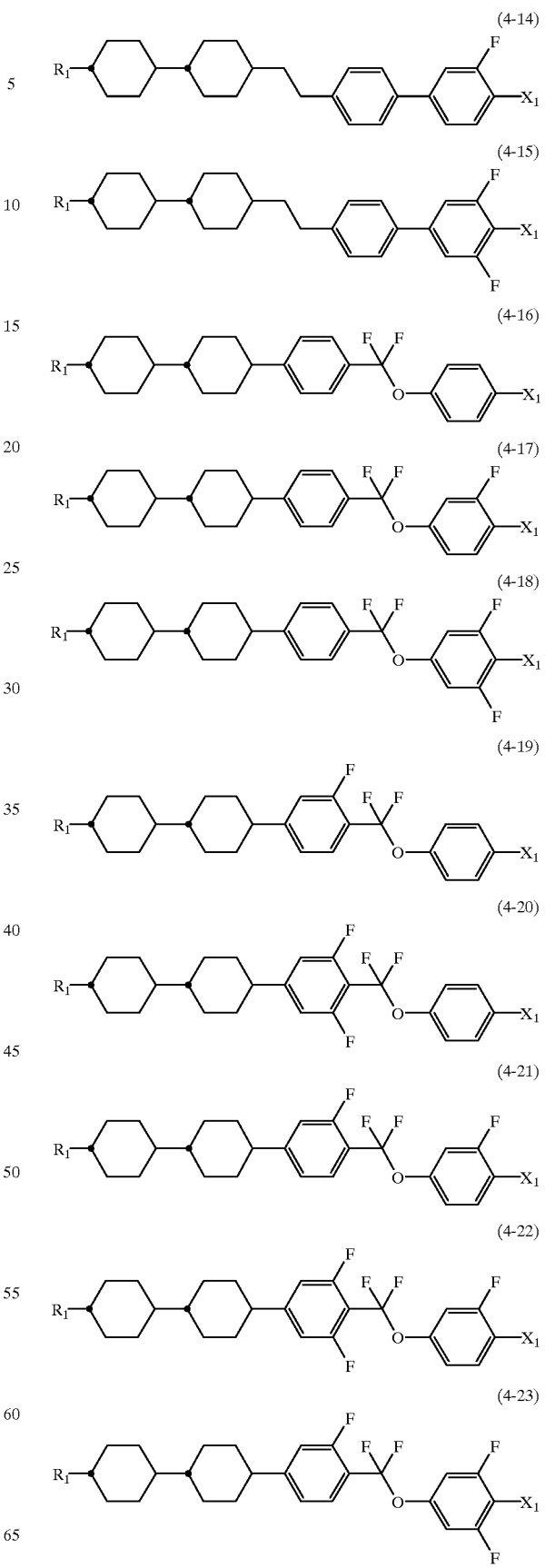

(4-24)

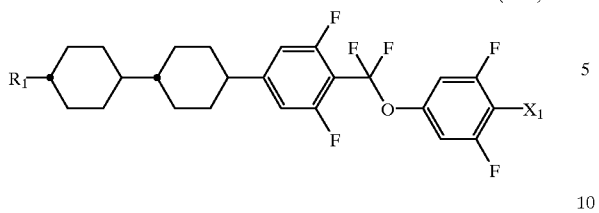

wherein $R_1$ and $X_1$ have the same meaning as described above.

Compounds expressed by one of the general formulas (2) to (4) have a positive dielectric anisotropy value, are remarkably excellent in thermal stability and chemical stability, and thus are extremely useful when liquid crystal compositions for TFT of which such a high reliability as an extremely high voltage holding ratio or high specific resistivity is required are produced.

When liquid crystal compositions for TFT are produced, the compounds expressed by one of the general formulas (2) to (4) can be used in the range of 0.1 to 99.9% by weight based on the total amount of liquid crystal composition, and the range is preferably 10 to 97% by weight and more desirably 40 to 95% by weight. The liquid crystal compositions may further comprise compounds expressed by one of the general formulas (7) to (9) for the purpose of adjusting viscosity.

Even when liquid crystal compositions for STN or TN are produced, compounds expressed by one of the general formulas (2) to (4) can be used, but their amount to be used is preferably 50% by weight or less.

As preferable examples of the compound used in the liquid crystal compositions of the present invention and expressed by the general formula (5) or (6), the following compounds can be mentioned:

(5-1)

(5-2)
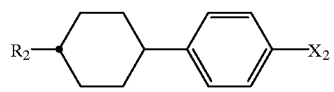

(5-3)
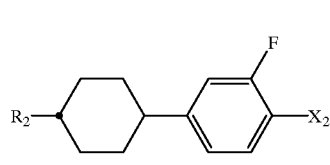

(5-4)
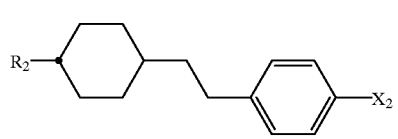

(5-5)
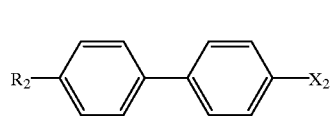

(5-6)
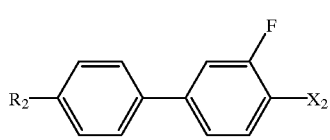

(5-7)
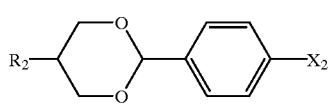

(5-8)
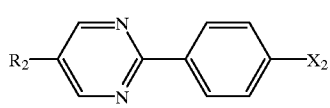

(5-9)
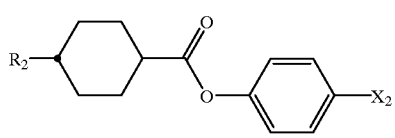

(5-10)
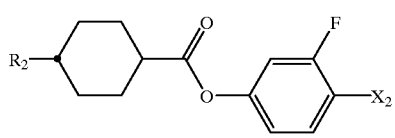

(5-11)
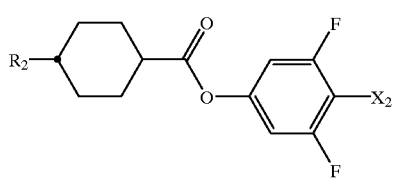

(5-12)
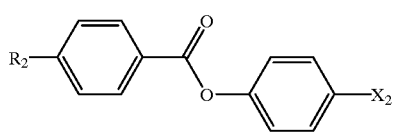

(5-13)
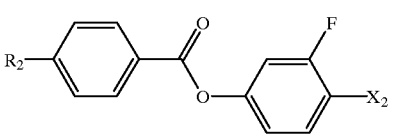

(5-14)
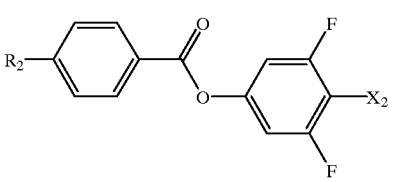

(5-15)
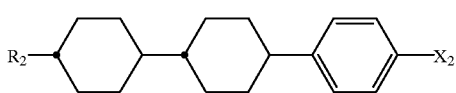

(5-16) 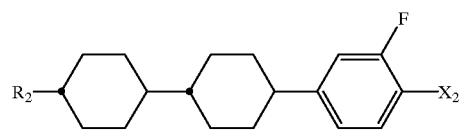
(5-17) 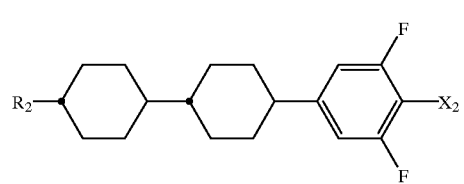
(5-18) 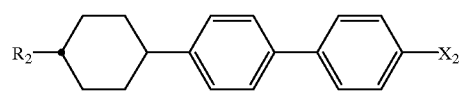
(5-19) 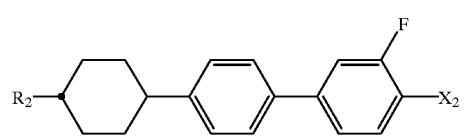
(5-20) 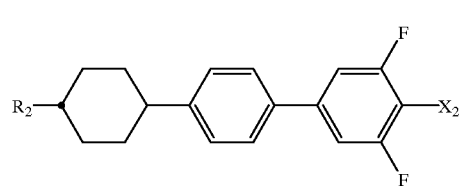
(5-21) 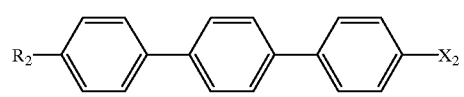
(5-22) 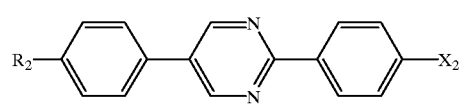
(5-23) 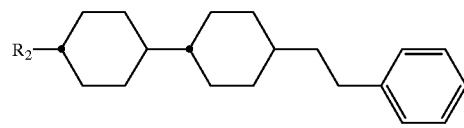
(5-24) 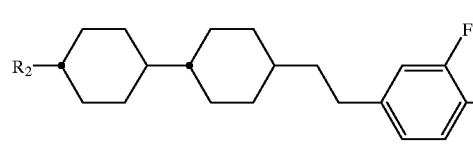
(5-25) 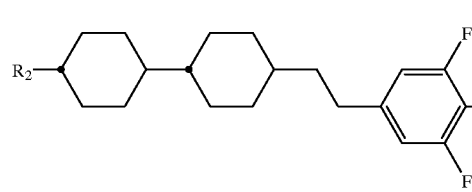
(5-26) 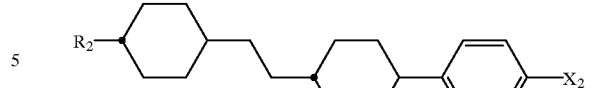
(5-27) 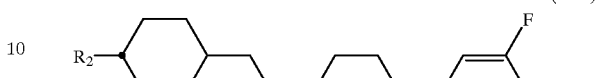
(5-28) 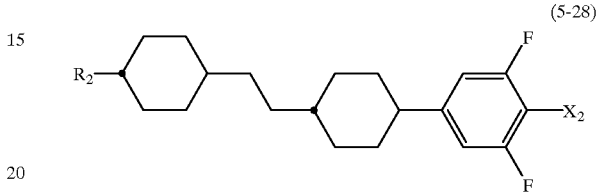
(5-29) 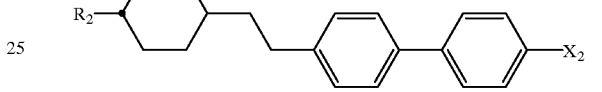
(5-30) 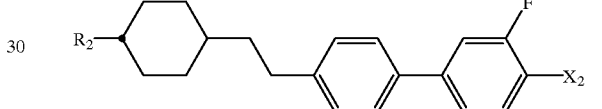
(5-31) 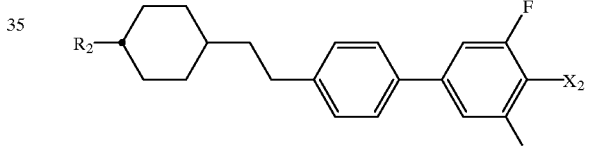
(5-32) 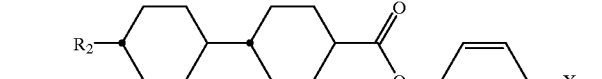
(5-33) 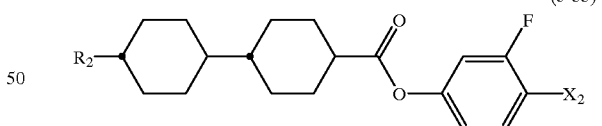
(5-34) 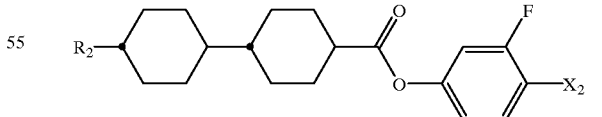
(5-35) 

-continued

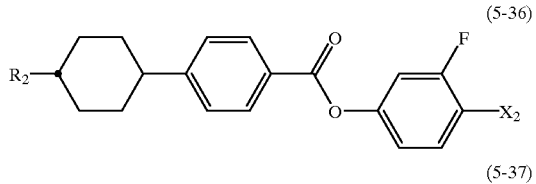
(5-36)

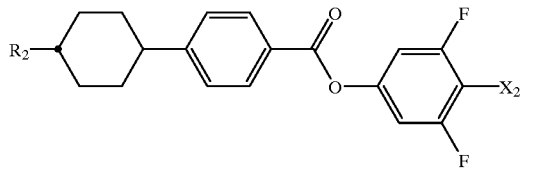
(5-37)

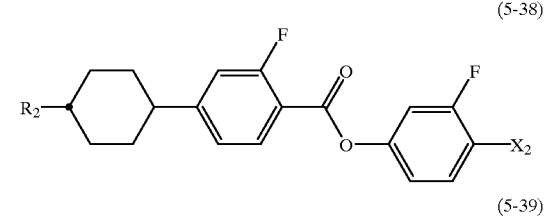
(5-38)

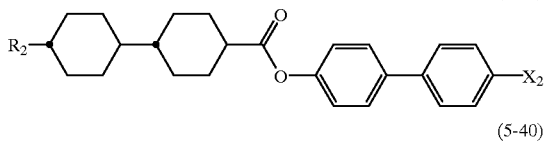
(5-39)

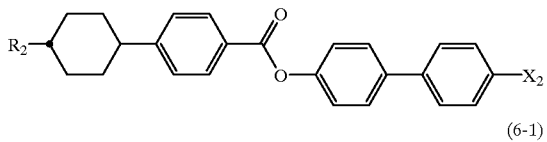
(5-40)

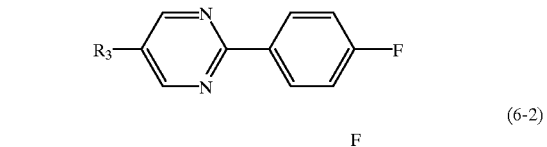
(6-1)

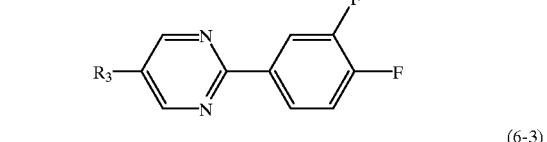
(6-2)

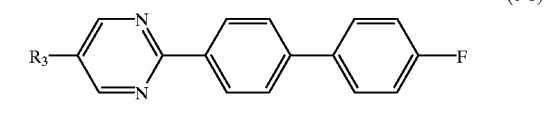
(6-3)

wherein $R_2$, $R_3$ and $X_2$ have the same meaning as described above.

Compounds expressed by the general formula (5) or (6) have a positive and large dielectric anisotropy value, and used particularly for the purpose of lowering threshold voltage of liquid crystal compositions. Also, they are used for adjusting optical anisotropy value, and for the purpose of widening nematic range such as raising clearing point. Further, they are also used for the purpose of improving the steepness of voltage-transmittance characteristic of liquid crystal compositions for STN or TN.

Compounds expressed by the general formula (5) or (6) are particularly useful when liquid crystal compositions for STN or TN are produced.

When the amount of the compounds expressed by the general formula (5) or (6) is increased in liquid crystal compositions, threshold voltage of liquid crystal compositions lowers but viscosity rises. Accordingly, it is advantageous to use the compounds in a large amount since driving at a low voltage becomes poissible, so far as viscosity of liquid crystal compositions satisfies a required value. When liquid crystal compositions for STN or TN are produced, the compounds expressed by the general formula (5) or (6) can be used in the range of 0.1 to 99.9% by weight, and the range is preferably 10 to 97% by weight and more desirably 40 to 95% by weight.

As preferable examples of the compound used in the liquid crystal compositions of the present invention and expressed by one of the general formulas (7) to (9), the following compounds can be mentioned:

(7-1)

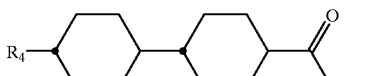
(7-2)

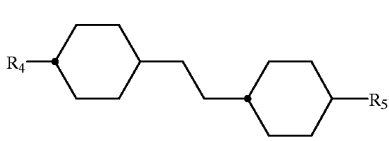
(7-3)

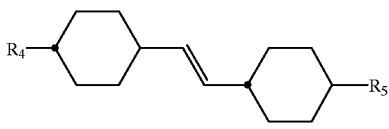
(7-4)

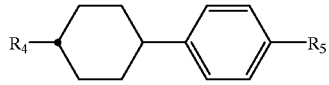
(7-5)

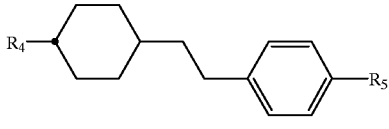
(7-6)

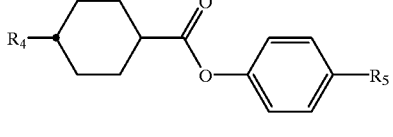
(7-7)

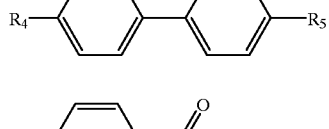
(7-8)

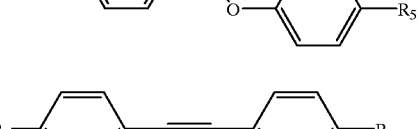
(7-9)

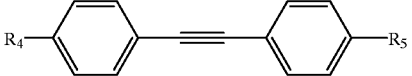
(7-10)

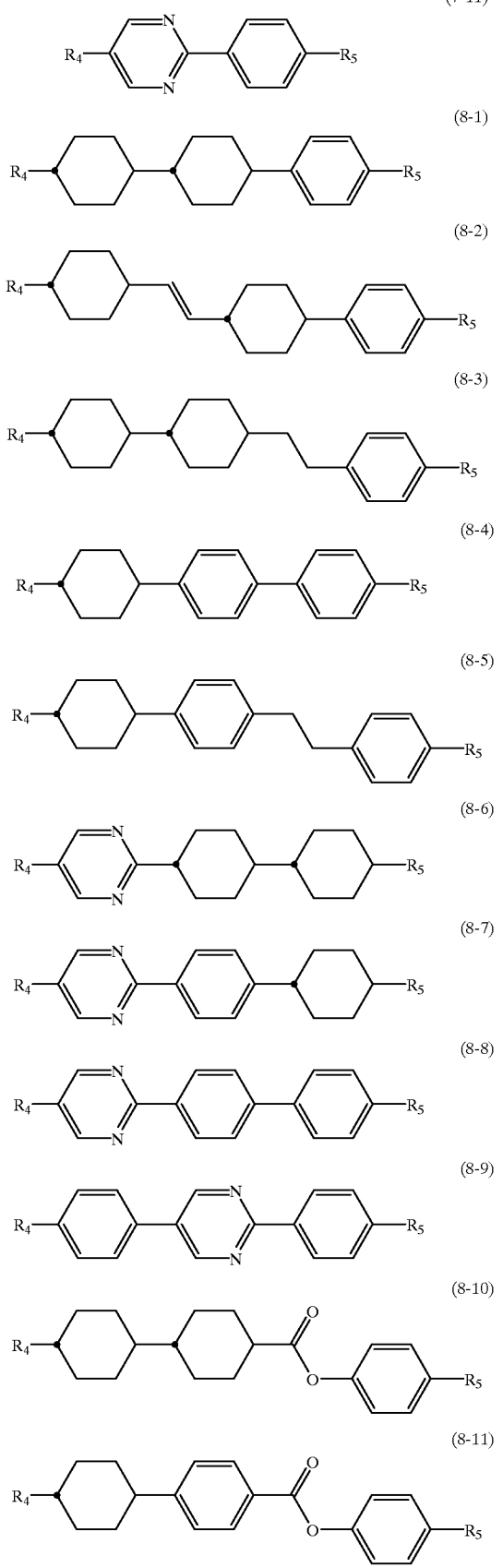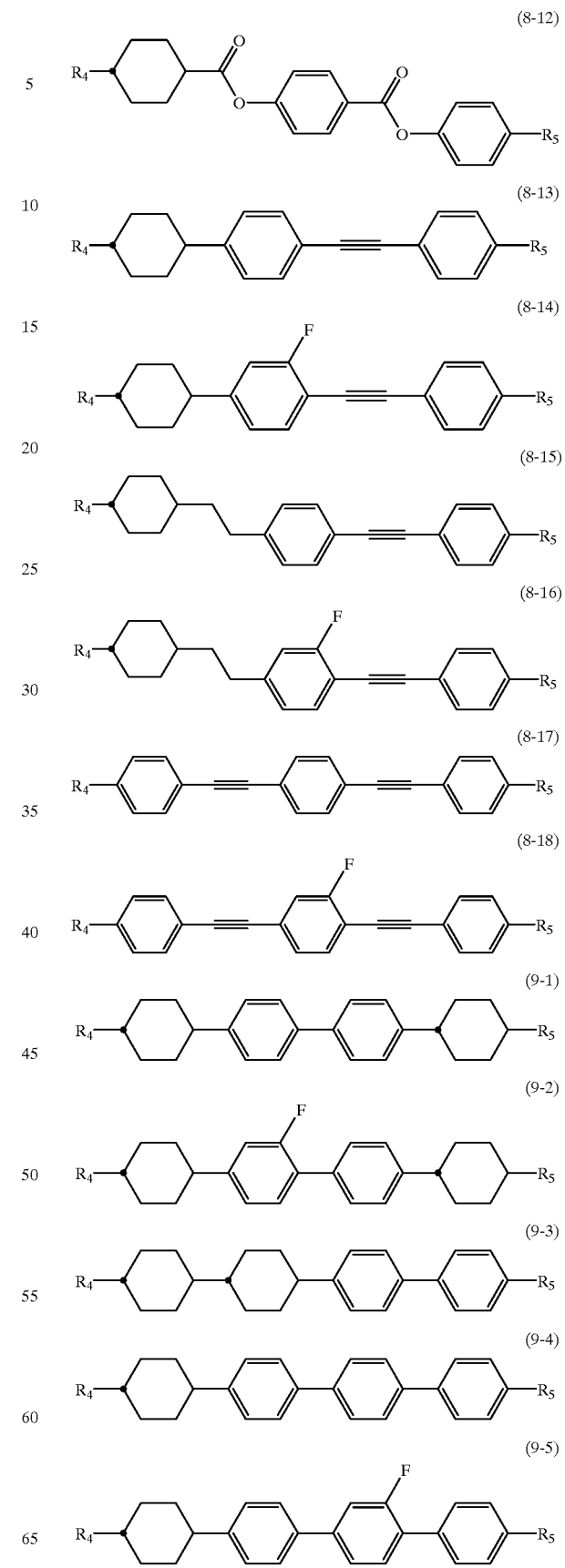

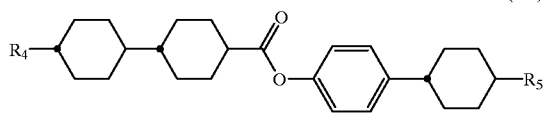
(9-6)

wherein $R_4$ and $R_5$ have the same meaning as described above.

Compounds expressed by one of the general formulas (7) to (9) have a small absolute value of dielectric anisotropy and are close to neutral. Compounds expressed by the general formula (7) are used principally for the purpose of adjusting viscosity or adjusting optical anisotropy value. Compounds expressed by the general formula (8) or (9) are used for the purpose of widening nematic range such as raising clearing point, or for the purpose of adjusting optical anisotropy value.

When the amount of the compounds expressed by one of the general formula (7) to (9) to be used is increased, threshold voltage of liquid crystal compositions rises and viscosity lowers. Accordingly, it is desirable to use the compounds in a large amount so far as threshold voltage of liquid crystal compositions satisfies a required value. When liquid crystal compositions for TFT are produced, the amount of the compounds expressed by one of the general formulas (7) to (9) to be used is preferably 40% by weight or less and more desirably 35% by weight or less. When liquid crystal compositions for STN or TN are produced, the amount of the compound expressed by one of the general formulas (7) to (9) to be used is preferably in the range of 70% by weight or less and more desirably 60% by weight or less.

As preferable examples of the compound used in the liquid crystal compositions of the present invention and expressed by one of the general formulas (10) to (12), the following compounds can be mentioned:

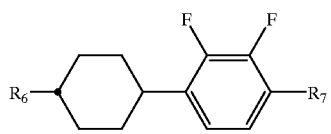
(10-1)

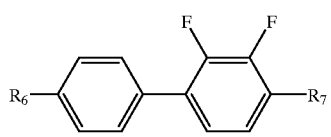
(10-2)

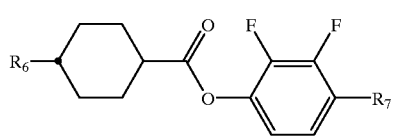
(10-3)

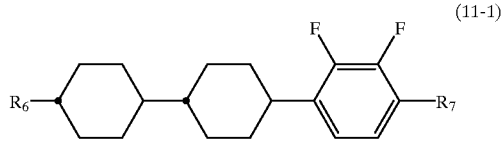
(11-1)

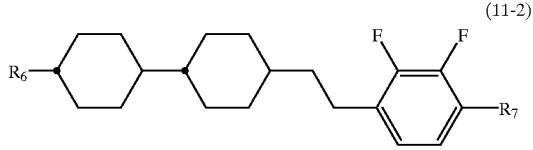
(11-2)

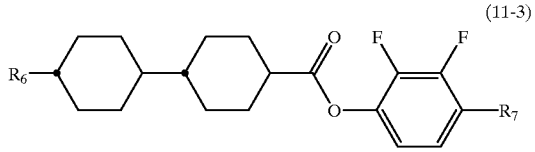
(11-3)

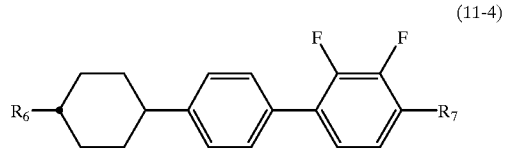
(11-4)

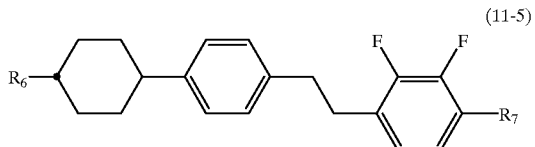
(11-5)

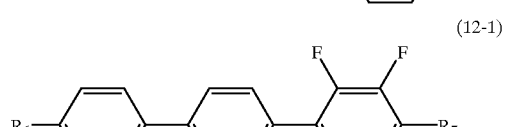
(12-1)

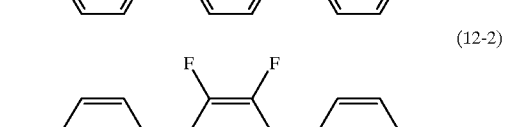
(12-2)

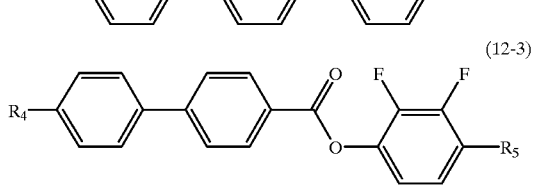
(12-3)

wherein $R_6$ and $R_7$ have the same meaning as described above.

Compounds expressed by one of the general formulas (10) to (12) have a negative dielectric anisotropy value. Since the compounds expressed by the general formula (10) are two-rings compounds, they are used principally for the purpose of adjusting threshold voltage, adjusting viscosity, or adjusting optical anisotropy value. Compounds expressed by the general formula (11) are used for the purpose of widening nematic range such as raising clearing point or for the purpose of adjusting optical anisotropy value. Compounds expressed by the general formula (12) are used for the purpose of lowering threshold voltage or increasing optical anisotropy value in addition to the purpose of widening nematic range.

Compounds expressed by one of the general formulas (10) to (12) are used principally for liquid crystal compositions of negative dielectric anisotropy value. When the amount of the compound to be used is increased, threshold voltage lowers, but viscosity rises. Accordingly, it is desirable to use the compound in a small amount so far as threshold voltage satisfies a required value. However, since the absolute value of dielectric anisotropy is 5 or less, when the amount becomes less than 40% by weight, driving at a low voltage sometimes becomes impossible. When liquid crystal compositions having a negative dielectric anisotropy value and used for TFT are produced, the amount of the compound expressed by one of the general formulas (10) to (12) to be used is preferably 40% by weight or more and more desirably 50 to 95% by weight. Besides, for the purpose of controlling elastic constant and regulating voltage-transmittance characteristic of liquid crystal compositions, the compound expressed by one of the general formulas (10) to (12) are sometimes mixed to compositions having a positive dielectric anisotropy value. In this case, the amount of the compound of the formulas (10) to (12) to be used is preferably 30% by weight or less.

With the exception of such specific cases as liquid crystal compositions for OCB (Optically Compensated Birefringence) mode and the likes, an optically active compound is usually added to the liquid crystal compositions of the present invention for the purpose of inducing helical structure of liquid crystal composition to adjust required twist angle and to prevent reverse twist. For such purposes, any known optically active compounds can be used, but the following optically active compounds can be mentioned as preferable examples:

Symbol: C15

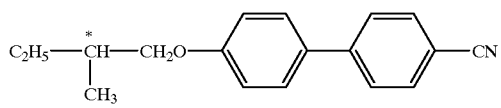

Symbol: CB15

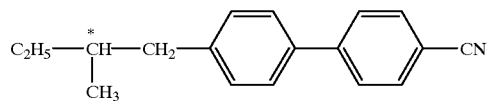

Symbol: CM21

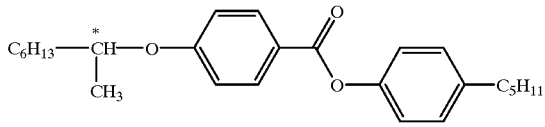

Symbol: CM33

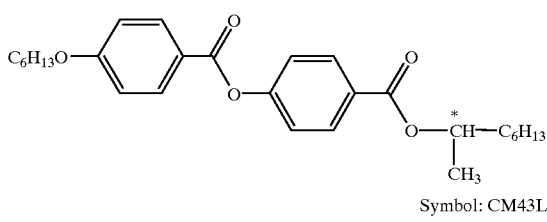

Symbol: CM43L

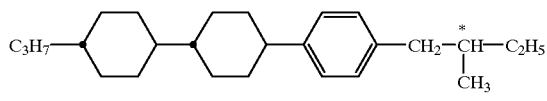

Symbol: CM45

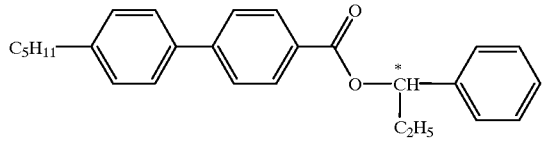

-continued

Symbol: CM47

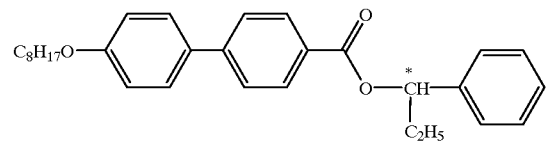

Symbol: CN

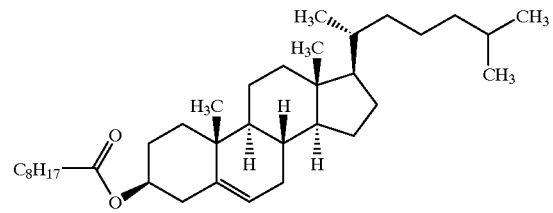

Liquid crystal compositions of the present invention are usually adjusted in their pitch of twist by adding these optically active compounds thereto. The twist pitch is preferably adjusted in the range of 40 to 200 μm in the case of liquid crystal compositions for TFT or TN, and preferably adjusted in the range of 6 to 20 μm in the case of liquid crystal compositions for STN. In the case for bistable TN mode, it is preferable to adjust the twist pitch in the range of 1.5 to 4 μm. Further, two or more kind of optically active compounds may be added for the purpose of adjusting the dependency of pitch on temperature.

Liquid crystal compositions of the present invention can be produced by conventional methods. Generally, a method in which various components are dissolved in one another at a high temperature has been adopted.

Further, the liquid crystal compositions of the present invention can be used as ones for guest-host (GH) mode by adding a dichroic dye such as merocyanine type, styryl type, azo type, azomethine type, azoxy type, quinophthalone type, anthraquinone type and tetrazine type thereto. Alternatively, the liquid crystal compositions can be used as NCAP which is prepared by the microencapsulation of a nematic liquid crystal, or as liquid crystal compositions for polymer dispersed liquid crystal display devices (PDLCD) represented by polymer net work liquid crystal display devices (PNLCD) prepared by forming a polymer of three-dimensional reticulated structure in a liquid crystal. Still further, the liquid crystal compositions of the present invention can be used as ones for electrically controlled birefringence (ECB) mode or dynamic scattering (DS) mode.

As examples of liquid crystal compositions comprising the compound of the present invention, the following can be mentioned. The compounds in Composition Examples, and Examples described below are designated by symbolizing them according to the definition shown below, and the compound No. in Composition Examples is given in the same rule as that shown in Examples.

| Left side terminal group Ra, $R_1$–$R_4$, $R_6$ | Symbol |
|---|---|
| $C_aH_{2a+1}$— | a— |
| $C_aH_{2a+1}O$— | aO— |
| $C_aH_{2a+1}OC_bH_{2b}$— | aOb— |
| $C_aH_{2a+i}OC_bH_{2b}O$— | aCbO— |
| $C_{a-1}H_{2(a-1)+1}C(C_bH_{2b+1})HC_cH_{2c}$— | a(b)c— |
| $CFH_2C_{a-1}H_{2(a-1)}$— | Fa— |

-continued

| | |
|---|---|
| CF$_2$HC$_{a-1}$H$_{2(a-1)}$— | FFa— |
| CF$_3$C$_{a-1}$H$_{2(a-1)}$— | FFFa— |
| CFH$_2$C$_{a-1}$H$_{2(a-1)}$O— | FaO— |
| CFH$_2$C$_{a-1}$H$_{2(a-1)}$OC$_b$H$_{2b}$— | FaOb— |
| C$_a$H$_{2a+1}$CFHC$_b$H$_{2b}$— | a(F)b— |
| C$_a$H$_{2a+1}$CF$_2$C$_b$H$_{2b}$— | a(FF)b— |
| C$_a$H$_{2a+1}$SiH$_2$C$_b$H$_{2b}$— | a(Si)b— |
| C$_a$H$_{2a+1}$CH=CHC$_b$H$_{2b}$— | aVb— |
| C$_a$H$_{2a+1}$CH=CHC$_b$H$_{2b}$CH=CHC$_c$H$_{2c}$— | aVbVc— |
| C$_a$H$_{2a+1}$CH=CHC$_b$H$_{2b}$OC$_c$H$_{2c}$— | aVbOc— |
| C$_a$H$_{2a+1}$OC$_b$H$_{2b}$CH=CHC$_c$H$_{2c}$— | aObVc— |
| CFH$_2$C$_{a-1}$H$_{2(a-1)}$CH=CHC$_b$H$_{2b}$— | FaVb— |
| FFC=CHC$_a$H$_{2a}$— | FFVa— |
| F(CN)C=CHC$_a$H$_{2a}$— | FCVa— |

| Bonding group Z$_1$~Z$_{10}$ | Symbol |
|---|---|
| —(CH$_2$)$_a$— | a |
| —CH$_2$O— | CH$_2$O |
| —OCH$_2$— | OCH$_2$ |
| —C$_3$H$_6$O— | C$_3$H$_6$O |
| —OC$_3$H$_6$— | OC$_3$H$_6$ |
| —COO— | E |
| —C≡C— | T |
| —CH=CH— | V |
| —CF$_2$O— | CF$_2$O |
| —OCF$_2$— | OCF$_2$ |

| Ring structure | Symbol | Ring structure | Symbol |
|---|---|---|---|
| 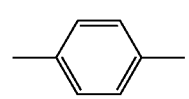 | B | 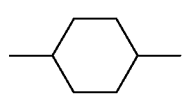 | H |
| 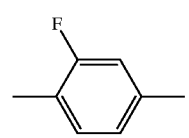 | B(2F) | 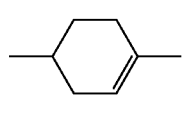 | Ch |
| 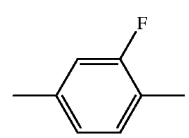 | B(3F) | 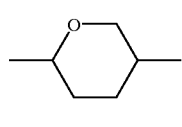 | P(2) |
| 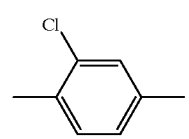 | B(2Cl) | 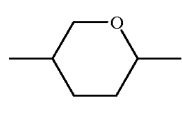 | P(3) |
| 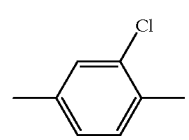 | B(3Cl) | 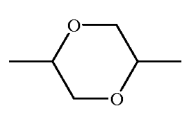 | D(2,5) |
| 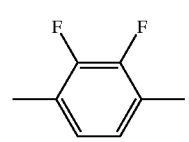 | B(2,3F) | 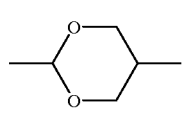 | D(1,6) |
| 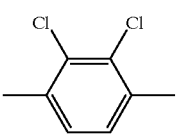 | B(2,3C) | 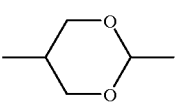 | D(3,5) |
| 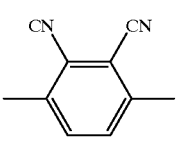 | B(2,3Cl) | 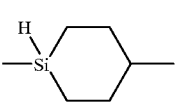 | Si(1) |
| 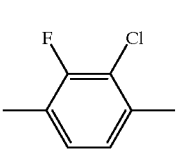 | B(2F,3Cl) | 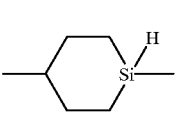 | Si(4) |
| 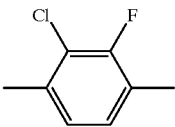 | B(2Cl,3F) | 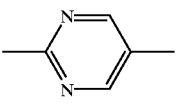 | Py(1,6) |
| 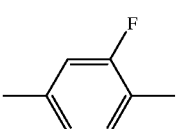 | B(3,5F) | 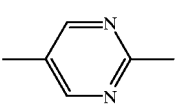 | Py(2,5) |
| 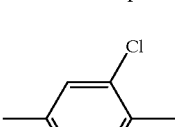 | B(3F,5Cl) | 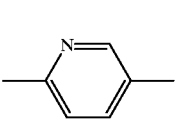 | Pr(2) |
| | | 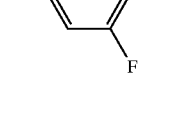 | Pr(3) |
| | |  | Pr(3F) |

| Right side terminal group Rb, R$_5$, R$_7$, X, X$_2$ | Symbol |
|---|---|
| —F | —F |
| —Cl | —CL |
| —CN | —C |
| —CF$_3$ | —CF$_3$ |
| —OCF$_3$ | —OCF$_3$ |
| —OCF$_2$H | —OCF$_2$H |
| —CF$_2$CF$_2$H | —CF$_2$CF$_2$H |
| —CF$_2$CH$_2$CF$_3$ | —CF$_2$CH$_2$CF$_3$ |
| —CF$_2$CFHCF$_3$ | —CF$_2$CFHCF$_3$ |
| —OCH$_2$CF$_2$H | —OCH$_2$CF$_2$H |
| —OCF$_2$CF$_2$H | —OCF$_2$CF$_2$H |
| —OCF$_2$CH$_2$CF$_3$ | —OCF$_2$CH$_2$CF$_3$ |
| —OCF$_2$CFHCF$_3$ | —OCF$_2$CFHCF$_3$ |
| —C$_w$H$_{2w+1}$ | —w |
| —OC$_2$H$_{2w+1}$ | —Ow |
| —C$_w$H$_{2w}$OC$_x$H$_{2x+1}$ | —wOx |

| -continued | |
|---|---|
| —OChd wH₂wOCₓH₂ₓ₊₁ | —OwOx |
| —Cw₋₁H₂(w₋₁)CFH₂ | —wF |
| —CwH₂wCH=CH₂ | —wV |
| —CwH₂wCH=CHCₓH₂ₓ₊₁ | —wVx |
| —CwH₂wCH=CHCₓH₂ₓCH=CH₂ | —wVxV |
| —COOCH₃ | —EMe |
| —CwH₂wCH=CHCₓ₋₁H₂(ₓ₋₁)CFH₂ | —wVxF |
| —CH=CF₂ | —VFF |
| —CwH₂wCH=CF₂ | —wVFF |
| —C≡C—CN | —TC |

When the hydrogen atom of trans-1,4-cyclohexylene in the following partial structure was replaced by deuterium (heavy hydrogen) at positions $Q_1$, $Q_2$ and $Q_3$, it is designated by symbol H[1D, 2D, 3D], and when replaced at positions $Q_5$, $Q_6$ and $Q_7$, it is designated by symbol H[5D, 6D, 7D]. In other words, the positions where deuterium substituted are indicated by the numeral in the bracket [ ].

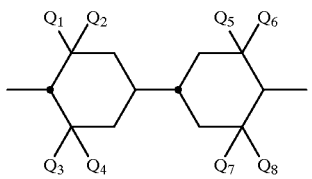

In the Composition Examples and Examples, "%" means % by weight unless otherwise specified. When cis-trans isomers exist in particular compounds, they are trans form.

COMPOSITION EXAMPLE 1

| 3-HCH₂OB(2F)B(3F)—O3 (Compound No. 276) | 15.0% |
|---|---|
| 3-HEB—O4 | 24.0% |
| 4-HEB—O2 | 17.0% |
| 5-HEB—O1 | 17.0% |
| 3-HEB—O2 | 15.0% |
| 5-HEB—O2 | 12.0% |

COMPOSITION EXAMPLE 2

| 3-HB (2F) B (3F)-03 (Compound No. 183) | 15.0% |
|---|---|
| 3-HEB-04 | 24.0% |
| 4-HEB-02 | 17.0% |
| 5-HEB-01 | 17.0% |
| 3-HEB-02 | 15.0% |
| 5-HEB-02 | 12.0% |

COMPOSITION EXAMPLE 3

| 3-HB(2F)B(3F)—O3 (Compound No. 183) | 10.0% |
|---|---|
| 3-HCH₂OB(2F)B(3F)—O3 (Compound No. 276) | 10.0% |
| 3-HH-2 | 5.0% |
| 3-HH-4 | 3.0% |
| 3-HH—O1 | 7.0% |
| 3-HH—O3 | 5.0% |
| 5-HH—O1 | 4.0% |
| 3-HB(2,3F)—O2 | 12.0% |
| 5-HB(2,3F)—O2 | 11.0% |
| 3-HHB(2,3F)—O2 | 14.0% |
| 5-HHB(2,3F)—O2 | 15.0% |
| 3-HHB(2,3F)-2 | 4.0% |

COMPOSITION EXAMPLE 4

| 3-HHCH₂OB(2F)B(3F)—O3 (Compound No. 383) | 5.0% |
|---|---|
| 3-HH-5 | 5.0% |
| 3-HH-4 | 5.0% |
| 3-HH—O1 | 6.0% |
| 3-HH—O3 | 6.0% |
| 3-HB—O1 | 5.0% |
| 3-HB—O2 | 6.0% |
| 3-HB(2,3F)—O2 | 10.0% |
| 5-HB(2,3F)—O2 | 10.0% |
| 3-HHB(2,3F)—O2 | 12.0% |
| 5-HHB(2,3F)—O2 | 13.0% |
| 3-HHB(2,3F)-2 | 4.0% |
| 2-HHB(2,3F)-1 | 4.0% |
| 3-HHEH-3 | 5.0% |
| 3-HHEH-5 | 4.0% |

COMPOSITION EXAMPLE 5

| 3O—B(2F)B(2F)B(3F)—O3 (Compound No. 1) | 4.0% |
|---|---|
| 3-HB(2F)B(3F)—O3 (Compound No. 183) | 5.0% |
| 3-BB(2,3F)—O2 | 13.0% |
| 3-BB(2,3F)—O4 | 10.0% |
| 5-BB(2,3F)—O4 | 10.0% |
| 2-BB(2,3F)B-3 | 25.0% |
| 3-BB(2,3F)B-5 | 13.0% |
| 5-BB(2,3F)B-5 | 14.0% |
| 5-BB(2,3F)B-7 | 6.0% |

COMPOSITION EXAMPLE 6

| 3O—B(2F)B(2F)B(3F)—O3 (Compound No. 1) | 3.0% |
|---|---|
| 3-HB(2F)B(3F)—O3 (Compound No. 183) | 3.0% |
| 3-HCH₂OB(2F)B(3F)—O3 (Compound No. 276) | 10.0% |
| 3-BB(2,3F)—O2 | 10.0% |
| 5-BB-5 | 7.0% |
| 5-BB—O6 | 9.0% |
| 5-BB—O8 | 8.0% |
| 1-BEB-5 | 6.0% |
| 3-BEB-5 | 6.0% |
| 5-BEB-5 | 3.0% |
| 3-HEB—O2 | 22.0% |
| 5-BBB(2,3F)-7 | 9.0% |
| 3-H2BB(2F)-5 | 4.0% |

COMPOSITION EXAMPLE 7

| 3O—B(2F)B(2F)B(3F)—O3 (Compound No. 1) | 4.0% |
|---|---|
| 3-HB(2F)B(3F)—O3 (Compound No. 183) | 13.0% |
| 3-HCH₂OB(2F)B(3F)—O3 (Compound No. 276) | 13.0% |
| 3-HHCH₂OB(2F)B(3F)—O3 (Compound No. 383) | 4.0% |
| 3-HB—O1 | 15.0% |
| 3-HB—O2 | 6.0% |
| 3-HEB(2,3F)—O2 | 9.0% |
| 4-HEB (2,3F)—O2 | 9.0% |

-continued

| | |
|---|---|
| 5-HEB(2,3F)—O2 | 4.0% |
| 2-BB2B—O2 | 6.0% |
| 1-B2BB(2F)-5 | 7.0% |
| 5-B(3F)BB—O2 | 3.0% |
| 3-BB(2,3F)B-3 | 7.0% |

COMPOSITION EXAMPLE 8

| | |
|---|---|
| 3O—B(2F)B(2F)B(3F)—O3 (Compound No. 1) | 3.0% |
| 3-HB(2F)B(3F)—O3 (Compound No. 183) | 3.0% |
| 3-HB—O1 | 9.0% |
| 3-HB—O2 | 11.0% |
| 3-HB—O4 | 9.0% |
| 2-BTB—O1 | 5.0% |
| 1-BTB—O2 | 3.0% |
| 3-BTB(2,3F)—O2 | 13.0% |
| 5-BTB(2,3F)—O2 | 13.0% |
| 3-B(2,3F)TB(2,3F)—O4 | 4.0% |
| 5-B(2,3F)TB(2,3F)—O4 | 4.0% |
| 3-HBTB—O1 | 5.0% |
| 3-HBTB—O2 | 4.0% |
| 3-HHB(2,3F)—O2 | 6.0% |
| 5-HBB(2,3F)—O2 | 5.0% |
| 5-BPr(3F)—O2 | 3.0% |

COMPOSITION EXAMPLE 9

| | |
|---|---|
| 3O—B(2F)B(2F)B(3F)—O3 (Compound No. 1) | 3.0% |
| 3-HB(2F)B(3F)—O3 (Compound No. 183) | 5.0% |
| 3-HB—O2 | 10.0% |
| 5-HB-3 | 8.0% |
| 5-BB(2,3F)—O2 | 10.0% |
| 3-HB(2,3F)—O2 | 10.0% |
| 5-HB(2,3F)—O2 | 8.0% |
| 3-HHB(2,3F)—O2 | 12.0% |
| 5-HHB(2,3F)—O2 | 4.0% |
| 5-HHB(2,3F)-1O1 | 4.0% |
| 2-HHB(2,3F)-1 | 5.0% |
| 3-HBB-2 | 6.0% |
| 3-BB(2,3F)B-3 | 8.0% |
| 5-B2BB(2,3F)B—O2 | 7.0% |

COMPOSITION EXAMPLE 10

| | |
|---|---|
| 3-HB(2F)B(3F)—O3 (Compound No. 183) | 3.0% |
| 3-HCH$_2$OB(2F)B(3F)—O3 (Compound No. 276) | 3.0% |
| 3-HHCH$_2$OB(2F)B(3F)—O3 (Compound No. 383) | 3.0% |
| 3-HB—O2 | 20.0% |
| 1O1-HH-3 | 6.0% |
| 1O1-HH-5 | 5.0% |
| 3-HH—EMe | 12.0% |
| 4-HEB—O1 | 9.0% |
| 4-HEB—O2 | 7.0% |
| 5-HEB—O1 | 8.0% |
| 3-HHB-1 | 3.0% |
| 4-HEB(2,3C)—O4 | 3.0% |
| 6-HEB(2,3C)—O4 | 3.0% |
| 3-HEB(2,3C)—O5 | 4.0% |
| 4-HEB(2,3C)—O5 | 3.0% |
| 5-HEB(2,3C)—O5 | 2.0% |
| 2-HBEB(2,3C)—O2 | 2.0% |
| 4-HBEB(2,3C)—O4 | 4.0% |

COMPOSITION EXAMPLE 11

| | |
|---|---|
| 3-HB(2F)B(3F)—O3 (Compound No. 183) | 10.0% |
| 1V2-BEB(3,5F)—C | 5.0% |
| 3-HB—C | 24.0% |
| V2-HB—C | 6.0% |
| 1-BTB-3 | 3.0% |
| 2-BTB-1 | 10.0% |
| 1O1-HH-3 | 3.0% |
| 3-HH-4 | 9.0% |
| 3-HHB-1 | 4.0% |
| 3-H2BTB-2 | 4.0% |
| 3-H2BTB-3 | 4.0% |
| 3-H2BTB-4 | 4.0% |
| 3-HB(3F)TB-2 | 6.0% |
| 3-HB(3F)TB-3 | 5.0% |
| 3-HHB—C | 3.0% |

COMPOSITION EXAMPLE 12

| | |
|---|---|
| 3-HB(2F)B(3F)—O3 (Compound No. 183) | 8.0% |
| 5-PyB—F | 4.0% |
| 3-PyB(3F)—F | 4.0% |
| 2-BB—C | 5.0% |
| 4-BB—C | 4.0% |
| 5-BB—C | 5.0% |
| 2-PyB-2 | 2.0% |
| 3-PyB-2 | 2.0% |
| 4-PyB-2 | 2.0% |
| 6-PyB—O5 | 3.0% |
| 6-PyB—O6 | 3.0% |
| 6-PyB—O7 | 3.0% |
| 6-PyB—O8 | 3.0% |
| 3-PyBB—F | 6.0% |
| 4-PyBB—F | 6.0% |
| 5-PyBB—F | 6.0% |
| 3-HHB-1 | 6.0% |
| 2-H2BTB-2 | 4.0% |
| 2-H2BTB-3 | 4.0% |
| 2-H2BTB-4 | 5.0% |
| 3-H2BTB-2 | 5.0% |
| 3-H2BTB-3 | 5.0% |
| 3-H2BTB-4 | 5.0% |

COMPOSITION EXAMPLE 13

| | |
|---|---|
| 3-HB(2F)B(3F)—O3 (Compound No. 183) | 4.0% |
| 3-HCH$_2$OB(2F)B(3F)—O3 (Compound No. 276) | 5.0% |
| 2O1-BEB(3F)—C | 5.0% |
| 3O1-BEB(3F)—C | 12.0% |
| 5O1-BEB(3F)—C | 4.0% |
| 1V2-BEB(3,5F)—C | 10.0% |
| 3-HEB—O4 | 4.0% |
| 3-HH—EMe | 6.0% |
| 3-HB—O2 | 18.0% |
| 7-HEB—F | 2.0% |
| 3-HHEB—F | 2.0% |
| 5-HHEB—F | 2.0% |
| 3-HBEB—F | 4.0% |
| 2O1-HBEB(3F)—C | 2.0% |
| 3-HB(3F)EB(3F)—C | 2.0% |
| 3-HBEB(3,5F)—C | 2.0% |
| 3-HHB—F | 4.0% |
| 3-HHB—O1 | 4.0% |
| 3-HEBEB—F | 2.0% |
| 3-HEBEB-1 | 2.0% |
| 3-HHB(3F)—C | 4.0% |

COMPOSITION EXAMPLE 14

| | |
|---|---|
| 3-HCH$_2$OB(2F)B(3F)—O3 (Compound No. 276) | 10.0% |
| 5-BEB(3F)—C | 5.0% |
| V—HB—C | 11.0% |
| 5-PyB—C | 6.0% |
| 4-BB-3 | 11.0% |
| 5-HH—V2V | 4.0% |
| 3-HH-2V | 10.0% |
| 5-HH—V | 7.0% |
| V—HHB-1 | 7.0% |
| V2-HHB-1 | 10.0% |
| 3-HHB-1 | 4.0% |
| 1V2-HBB-2 | 10.0% |
| 3-HHEBH-3 | 5.0% |

COMPOSITION EXAMPLE 15

| | |
|---|---|
| 3-HB(2F)B(3F)—O3 (Compound No. 183) | 11.0% |
| 5-BTB(3F)TB-3 | 10.0% |
| V2-HB—TC | 10.0% |
| 3-HB—TC | 10.0% |
| 3-HB—C | 12.0% |
| 5-HB—C | 7.0% |
| 5-BB—C | 3.0% |
| 2-BTB-1 | 10.0% |
| 2-BTB—O1 | 4.0% |
| 3-HH-4 | 4.0% |
| 3-HHB-1 | 10.0% |
| 3-H2BTB-2 | 3.0% |
| 3-H2BTB-3 | 3.0% |
| 3-HB(3F)TB-2 | 3.0% |

COMPOSITION EXAMPLE 16

| | |
|---|---|
| 3O—B(2F)B(2F)B(3F)—O3 (Compound No. 1) | 2.0% |
| 3-HB(2F)B(3F)—O3 (Compound No. 183) | 5.0% |
| 1V2-BEB(3,5F)—C | 6.0% |
| 3-HB—C | 18.0% |
| 2-BTB-1 | 10.0% |
| 5-HH—VFF | 30.0% |
| 1-BHH—VFF | 8.0% |
| 1-BHH-2VFF | 4.0% |
| 3-H2BTB-2 | 5.0% |
| 3-H2BTB-3 | 4.0% |
| 3-H2BTB-4 | 4.0% |
| 3-HHB-1 | 4.0% |

COMPOSITION EXAMPLE 17

| | |
|---|---|
| 3-HB(2F)B(3F)—O3 (Compound No. 183) | 5.0% |
| 7-HB(3F)—F | 5.0% |
| 5-H2B(3F)—F | 5.0% |
| 3-HB—O2 | 10.0% |
| 3-HH-4 | 2.0% |
| 3-HH[5D,6D,7D]-4 | 3.0% |
| 2-HHB(3F)—F | 10.0% |
| 3-HHB(3F)—F | 10.0% |
| 5-HH[5D,6D,7D]B(3F)—F | 10.0% |
| 3-H2HB(3F)—F | 5.0% |
| 2-HBB(3F)—F | 3.0% |
| 3-HBB(3F)—F | 3.0% |
| 5-HBB(3F)—F | 6.0% |
| 2-H2BB(3F)—F | 5.0% |
| 3-H2BB(3F)—F | 6.0% |
| 3-HHB-1 | 3.0% |
| 3-HHB—O1 | 5.0% |
| 3-HHB-3 | 4.0% |

COMPOSITION EXAMPLE 18

| | |
|---|---|
| 3-HCH$_2$OB(2F)B(3F)—O3 (Compound No. 276) | 6.0% |
| 7-HB(3,5F)—F | 5.0% |
| 3-H2HB(3,5F)—F | 2.0% |
| 3-HHB(3,5F)—F | 10.0% |
| 4-HHB(3,5F)—F | 5.0% |
| 3-HBB(3,5F)—F | 10.0% |
| 3-HHEB(3,5F)—F | 10.0% |
| 4-HHEB(3,5F)—F | 3.0% |
| 5-HHEB(3,5F)—F | 3.0% |
| 2-BEB(3,5F)—F | 3.0% |
| 3-HBEB(3,5F)—F | 5.0% |
| 5-HBEB(3,5F)—F | 3.0% |
| 3-HD(3,5)B(3,5F)—F | 15.0% |
| 3-HBCF$_2$OB—OCF$_3$ | 4.0% |
| 3-HHBB(3,5F)—F | 6.0% |

COMPOSITION EXAMPLE 19

| | |
|---|---|
| 3-HCH$_2$OB(2F)B(3F)—O3 (Compound No. 276) | 5.0% |
| 3-HB—CL | 10.0% |
| 5-HB—CL | 4.0% |
| 7-HB—CL | 4.0% |
| 1O1-HH-5 | 5.0% |
| 2-HBB(3F)—F | 8.0% |
| 3-HBB(3F)—F | 8.0% |
| 5-HBB(3F)—F | 14.0% |
| 4-HHB—CL | 8.0% |
| 5-HHB—CL | 3.0% |
| 3-H2HB(3F)—CL | 4.0% |
| 3-HBB(3,5F)—F | 10.0% |
| 5-H2BB(3,5F)—F | 9.0% |
| 3-HB(3F)VB-2 | 4.0% |
| 3-H2BTB-2 | 4.0% |

COMPOSITION EXAMPLE 20

| | |
|---|---|
| 3-HB(2F)B(3F)—O3 (Compound No. 183) | 5.0% |
| 5-HB—F | 12.0% |
| 6-HB—F | 9.0% |
| 7-HB—F | 7.0% |
| 2-HHB—OCF$_3$ | 7.0% |
| 3-HHB—OCF$_3$ | 7.0% |
| 4-HHB—OCF$_3$ | 7.0% |
| 3-HH2B—OCF$_3$ | 4.0% |
| 5-HH2B—OCF$_3$ | 4.0% |
| 3-HHB(3,5F)—OCF$_3$ | 5.0% |
| 3-HBB(3F)—F | 10.0% |
| 5-HBB(3F)—F | 10.0% |
| 3-HH2B(3F)—F | 3.0% |
| 3-HB(3F)BH-3 | 3.0% |
| 5-HBBH-3 | 3.0% |
| 3-HHB(3,5F)—OCF$_2$H | 4.0% |

COMPOSITION EXAMPLE 21

| | |
|---|---|
| 3-HB(2F)B(3F)—O3 (Compound No. 183) | 5.0% |
| 3-HCH$_2$OB(2F)B(3F)—O3 (Compound No. 276) | 5.0% |
| 5-H4HB(3,5F)—F | 7.0% |
| 5-H4HB—OCF$_3$ | 15.0% |
| 3-H4HB(3,5F)—CF$_3$ | 8.0% |
| 5-H4HB(3,5F)—CF$_3$ | 10.0% |
| 3-HB—CL | 6.0% |
| 5-HB—CL | 4.0% |
| 2-H2BB(3F)—F | 5.0% |
| 5-HVHB(3,5F)—F | 5.0% |
| 3-HHB—OCF$_3$ | 5.0% |
| 3-H2HB—OCF$_3$ | 5.0% |
| V-HHB(3F)—F | 5.0% |
| 3-HHB(3F)—F | 5.0% |
| 5-HHEB—OCF$_3$ | 2.0% |
| 3-HBEB(3,5F)—F | 5.0% |
| 5-HH-V2F | 3.0% |

COMPOSITION EXAMPLE 22

| | |
|---|---|
| 3O—B(2F)B(2F)B(3F)—O3 (Compound No. 1) | 2.0% |
| 3-HB(2F)B(3F)—O3 (Compound No. 183) | 3.0% |
| 3-HCH$_2$OB(2F)B(3F)—O3 (Compound No. 276) | 10.0% |
| 2-HHB(3F)—F | 2.0% |
| 3-HHB(3F)—F | 2.0% |
| 5-HHB(3F)—F | 2.0% |
| 2-HBB(3F)—F | 6.0% |
| 3-HBB(3F)—F | 7.0% |
| 2-H2BB(3F)—F | 9.0% |
| 3-H2BB(3F)—F | 4.0% |
| 3-HBB(3,5F)—F | 25.0% |
| 5-HBB(3,5F)—F | 19.0% |
| 1O1-HBBH-4 | 5.0% |
| 1O1-HBBH-5 | 4.0% |

BEST MODE FOR CARRYING OUT THE INVENTION

Now, the present invention will be described in more detail. with reference to Examples. In each of the Examples, C indicates crystal, $S_A$: smectic phase A, $S_B$: smectic phase B, $S_x$: smectic phase the structure of which has not been defined, N: nematic phase, and Iso: isotropic phase, and unit of all phase transition temperatures is ° C.

EXAMPLE 1

Preparation of 3,3',3''-trifluoro-4,4''-dipropoxyterphenyl (3O—B(2F)B(2F)B(3F)—O3 (Compound No. 1))

(First step) Preparation of 3,3'-difluoro-4-propoxybiphenyl

A mixture of 22.0 g (94.4 mmol) of 3-fluoro-4-propoxybromobenzene, 22.5 g (141.6 mmol) of dihydroxy (3-fluorophenyl)borane (prepared by reacting a Grignard reagent, which was prepared from 3-fluorobromobenzene and magnesium, with trimethoxyborane, and then hydrolysing with hydrochloric acid), 26.1 g (188.8 mmol) of K$_2$CO$_3$, 2.0 g of 5%Pd—C, and 150 ml of mixed solvent of toluene/ethanol/water (1/1/1) was heated to reflux for 27 hours. Subsequently, the Pd—C was removed by filtration, the mixture was extracted with 150 ml of toluene, the organic layer thus obtained was washed with water thrice, and then dried over anhydrous magnesium sulfate. The solvent was distilled off under a reduced pressure, and the residue thus obtained was subjected to silica gel column chromatography (eluent: heptane/toluene=1/1) to obtain 20.1 g of a crude 3,3'-difluoro-4-propoxybiphenyl. (Yield: 86.1%)

This product was used for next reaction without further purification.

(Second step) Preparation of 3,3'-difluoro-4'-iodo-4-propoxybiphenyl

In a solution of 5.0 g (20.1 mmol) of the 3,3'-difluoro-4-propoxybiphenyl obtained in the previous step in 35 ml of tetrahydrofuran (THF) was added by drops 23 ml (1.04M, cyclohexane solution, corresponding to 24.2 mmol) of sec-butyllithium while being maintained at a temperature −60° C. or lower. After finishing of the dropping, the solution was stirred at the same temperature for 1 hour. To the reaction mixture was added by drops a solution of 6.6 g (26.2 mmol) of iodine in 400 ml of THF while being maintained at a temperature −60° C. or lower, and stirred at the same temperature for 1 hour.

After 200 ml of a diluted hydrochloric acid was added by drops to the reaction solution, it was extracted with 150 ml of heptane. After the organic layer thus obtained was washed with a diluted aqueous sodium bicarbonate solution twice and with water thrice, it was dried over anhydrous magnesium sulfate. The solvent was distilled off under a reduced pressure, and the residue thus obtained was subjected to silica gel column chromatography (eluent: heptane/toluene=8/2) to obtain 5.6 g of a crude 3,3'-difluoro-4'-iodo-4-propoxybiphenyl. (Yield: 74.2%)

This product was used for next reaction without further purification.

(Third step) Preparation of 3,3',3''-trifluoro-4,4''-dipropoxyterphenyl

A mixture of 3.0 g (8.0 mmol) of the 3,3'-difluoro-4'-iodo-propoxybiphenyl obtained in the previous step, 2.1 g (10.4 mmol) of dihydroxy(3-fluoro-4-propoxyphenyl)borane, 2.2 g (16.0 mmol) of K$_2$CO$_3$, 0.3 g of 5%Pd—C, and 45 ml of mixed solvent of toluene/ethanol/water (1/1/1) was heated to reflux for 30 hours. Subsequently, the Pd—C was removed by filtration, the mixture was extracted with 100 ml of toluene, the organic layer thus obtained was washed with water thrice, and then dried over anhydrous magnesium sulfate. The solvent was distilled off under a reduced pressure, and the residue thus obtained was subjected to silica gel column chromatography (eluent: heptane/toluene: 6/4) to obtain 2.7 g of a crude 3,3',3''-trifluoro-4,4''-dipropoxyterphenyl. This product was recrystallized from mixed solvent of heptane/ethyl acetate (7/3) to obtain 1.9 g of the subject compound. (Yield: 58.6%)

This compound exhibited a liquid crystal phase and its phase transition temperatures were as follows:

C 129.4~129.5 $S_A$ 155.4~155.5 N 158.8~158.9 Iso

Further, data of each spectrum well supported its structure.

Mass analysis: 400 (M+)
$^1$H-NMR (CDCl$_3$, TMS internal standard)
δ (ppm)
1.06 (t, 6H)
1.88 (tq, 4H)
4.04 (t, 4H)
7.01–7.37 (m, 9H)

According to the method of Example 1, the following compounds can be synthesized. (In the following, "Compound No." is abbreviated to "Cpd. No.".)

Cpd. No. 2: 2-B(2F)B(2F)B(3F)-3
Cpd. No. 3: 5-B(2F)B(2F)B(3F)-2
Cpd. No. 4: 10-B(2F)B(2F)B(3F)-2

Cpd. No. 5: 16-B(2F)B(2F)B(3F)-1
Cpd. No. 6: 3O1-B(2F)B(2F)B(3F)-3
Cpd. No. 7: 1O4-B(2F)B(2F)B(3F)-5
Cpd. No. 8: 5O—B(2F)B(2F)B(3F)—O12
Cpd. No. 9: 3-B(3F)B(2F)B(3F)-2
Cpd. No. 10: 4-B(3F)B(2F)B(3F)-5
Cpd. No. 11: 7-B(3F)B(2F)B(3F)—O2
Cpd. No. 12: 2O1-B(3F)B(2F)B(3F)—O3
Cpd. No. 13: F3-B (3F)B(2F)B(3F)-3
Cpd. No. 14: 2-B(2,3F)B(2F)B(3F)-5
Cpd. No. 15: 6-B(2,3F)B(2F)B(3F)-4
Cpd. No. 16: 4O-B(2,3F)B(2F)B(3F)-2
Cpd. No. 17: 5O—B(2,3F)B(2F)B(3F)—O2
Cpd. No. 18: F2-B(2,3F)B(2F)B(3F)—O3
Cpd. No. 19: F2-B(2,3F)B(2F)B(3F)—O3
Cpd. No. 20: 3-BBB(2F)B(3F)-4
Cpd. No. 21: 5-BBB(2F)B(3F)-2
Cpd. No. 22: 7-BBB(2F)B(3F)-3
Cpd. No. 23: 7-BBB(2F)B(3F)—O3
Cpd. No. 24: 3O—BBB(2F)B(3F)-6
Cpd. No. 25: 7O—BBB(2F)B(3F)-13
Cpd. No. 26: 3-BB(3F)B(2F)B(3F)-2
Cpd. No. 27: 4-BB(3F)B(2F)B(3F)-3
Cpd. No. 28: 7-BB(3F)B(2F)B(3F)-1
Cpd. No. 29: F5-BB(3F)B(2F)B(3F)-3
Cpd. No. 30: 3-BB(2F)B(2F)B(3F)—O3
Cpd. No. 31: 3O1-BB(2F)B(2F)B(3F)—O2
Cpd. No. 32: 1O5-BB(2F)B(2F)B(3F)—O5
Cpd. No. 33: 3-B(3F)BB(2F)B(3F)-2
Cpd. No. 34: 5-B(3F)BB(2F)B(3F)-2
Cpd. No. 35: 2O—B(2F)BB(2F)B(3F)-5
Cpd. No. 36: 5O—B(2F)BB(2F)B(3F)—O2
Cpd. No. 37: 3-BB(2,3F)B(2F)B(3F)-2
Cpd. No. 38: 5-BB(2,3F)B(2F)B(3F)-1
Cpd. No. 39: 5-BB(2,3F)B(2F)B(3F)-03
Cpd. No. 40: 3O—B(2,3F)BB(2F)B(3F)-4
Cpd. No. 41: 5O—B(2,3F)BB(2F)B(3F)—O1
Cpd. No. 42: 2-B(2F)B(2,3F)B(2F)B(3F)-4
Cpd. No. 43: 5-B(2F)B(2,3F)B(2F)B(3F)-5
Cpd. No. 44: 2O—B(2F)B(2,3F)B(2F)B(3F)—O3
Cpd. No. 45: 3O—B(2F)B(2,3F)B(2F)B(3F)-2
Cpd. No. 46: 7O—B(2F)B(2,3F)B(2F)B(3F)-3
Cpd. No. 47: 1O3-B(2F)B(2,3F)B(2F)B(3F)-3
Cpd. No. 48: F3-B(2F)B(2,3F)B(2F)B(3F)-4
Cpd. No. 49: 3-B(2F)B(2F)B(3F)B(3F)-2
Cpd. No. 50: 5-B(2F)B(2F)B(3F)B(3F)-2
Cpd. No. 51: 4-B(2F)B(2F)B(3F)B(3F)-3
Cpd. No. 52: 5-B(2F)B(2F)B(3F)B(3F)-3
Cpd. No. 53: 2O—B(2F)B(2F)B(3F)B(3F)-3
Cpd. No. 54: 3O—B(2F)B(2F)B(3F)B(3F)—O2
Cpd. No. 55: 2-B(2,3F)B(2F)B(3F)B-1
Cpd. No. 56: 2-B(2,3F)B(2F)B(3F)B-9
Cpd. No. 57: 3O—B(2,3F)B(2F)B(3F)B-2
Cpd. No. 58: 4O—B(2,3F)B(2F)B(3F)B-3
Cpd. No. 59: 5O—B(2,3F)B(2F)B(3F)B-3
Cpd. No. 60: 3-B(2,3F)B(2F)B(3F)B(2,3F)-1
Cpd. No. 61: 3-B(2,3F)B(2F)B(3F)B(2,3F)-5
Cpd. No. 62: 5-B(2,3F)B(2F)B(3F)B(2,3F)-2
Cpd. No. 63: 3O—B(2,3F)B(2F)B(3F)B(2,3F)-4
Cpd. No. 64: 3O—B(2,3F)B(2F)B(3F)B(2,3F)-5
Cpd. No. 65: 3O—B(2,3F)B(2F)B(3F)B(2,3F)—O2
Cpd. No. 66: 3-B2B(2,3F)B(2F)B(3F)-2
Cpd. No. 67: 3-B2B(2,3F)B(2F)B(3F)-4
Cpd. No. 68: 3-B2B(2,3F)B(2F)B(3F)-5
Cpd. No. 69: 12-B2B(2,3F)B(2F)B(3F)-3
Cpd. No. 70: 5-B2B(2,3F)B(2F)B(3F)—O2
Cpd. No. 71: 5-B2B(2,3F)B(2F)B(3F)—O5
Cpd. No. 72: 5-B2B(2,3F)B(2F)B(3F)—O10
Cpd. No. 73: 1O1-B2B(2,3F)B(2F)B(3F)—O3
Cpd. No. 74: 3O1-B2B(2,3F)B(2F)B(3F)—O3
Cpd. No. 75: 1O4-B2B(2,3F)B(2F)B(3F)—O3
Cpd. No. 76: 2-B(2,3F)2BB(2F)B(3F)-1
Cpd. No. 77: 2-B(2,3F)2BB(2F)B(3F)-3
Cpd. No. 78: 2-B(2,3F)2BB(2F)B(3F)-5
Cpd. No. 79: 2-B(2,3F)2BB(2F)B(3F)-7
Cpd. No. 80: 1O—B(2,3F)2BB(2F)B(3F)-3
Cpd. No. 81: 3O—B(2,3F)2BB(2F)B(3F)-3
Cpd. No. 82: 4O—B(2,3F)2BB(2F)B(3F)—O2
Cpd. No. 83: 5O—B(2,3F)2BB(2F)B(3F)—O3
Cpd. No. 84: 2O2-B(2,3F)2BB(2F)B(3F)—O4
Cpd. No. 85: F4-B(2,3F)2BB(2F)B(3F)—O4
Cpd. No. 86: 3-B(2F)2BB(2,3F)B(2F)B(3F)-2
Cpd. No. 87: 5O—B(2,3F)2B(2,3F)B(2F)B(3F)3
Cpd. No. 88: 3-B(2F)B(2F)B(3F)2B(3F)-5
Cpd. No. 89: 5-B(2F)B(2F)B(3F)2B(3F)-3
Cpd. No. 90: 3O—B(2F)B(2F)B(3F)2B(3F)-2
Cpd. No. 91: 5O—B(2F)B(2F)B(3F)2B(3F)—O2
Cpd. No. 92: 3O—B(2,3F)B(2F)B(3F)2B-2
Cpd. No. 93: 3O—B(2,3F)B(2F)B(3F)2B-5
Cpd. No. 94: 8O—B(2,3F)B(2F)B(3F)2B-3
Cpd. No. 95: 3-BB(2F)B(3F)2B(2,3F)-5
Cpd. No. 96: 4-BB(2F)B(3F)2B(2,3F)—O2
Cpd. No. 97: F6-BB(2F)B(3F)2B(2,3F)—O3
Cpd. No. 98: 3-HBB(2F)B(3F)-1
Cpd. No. 99: 3-HBB(2F)B(3F)-5
Cpd. No. 100: 10-HBB(2F)B(3F)-10
Cpd. No. 101: 4-HBB(2F)B(3F)O—2
Cpd. No. 102: 4-HBB(2F)B(3F)—O3
Cpd. No. 103: F3-HBB(2F)B(3F)—O2
Cpd. No. 104: F4-HBB(2F)B(3F)—O3
Cpd. No. 105: 2-HB(3F)B(2F)B(3F)-3
Cpd. No. 106: 2-HB(3F)B(2F)B(3F)—O2
Cpd. No. 107: 3-HB(2F)B(2F)B(3F)-3
Cpd. No. 108: 3-HB(2F)B(2F)B(3F)—O2
Cpd. No. 109: 2-HB(2,3F)B(2F)B(3F)-3
Cpd. No. 110: 3-HB(2,3F)B(2F)B(3F)-3
Cpd. No. 111: 3-HB(2,3F)B(2F)B(3F)-4
Cpd. No. 112: 3-HB(2,3F)B(2F)B(3F)-5
Cpd. No. 113: 5-HB(2,3F)B(2F)B(3F)-2
Cpd. No. 114: 5-HB(2,3F)B(2F)B(3F)-2
Cpd. No. 115: 3-HB(2,3F)B(2F)B(3F)—O1
Cpd. No. 116: 3-HB(2,3F)B(2F)B(3F)—O3
Cpd. No. 117: 5-HB(2,3F)B(2F)B(3F)—O2
Cpd. No. 118: 14-HB(2,3F)B(2F)B(3F)—O1
Cpd. No. 119: 4O—HB(2,3F)B(2F)B(3F)—O3
Cpd. No. 120: 3O1-HB(2,3F)B(2F)B(3F)—O3
Cpd. No. 121: F2-HB(2,3F)B(2F)B(3F)-3
Cpd. No. 122: F3-HB(2,3F)B(2F)B(3F)—O2
Cpd. No. 123: 3-Si(1)B(2,3F)B(2F)B(3F)—O4
Cpd. No. 124: 3-D(2,5)B(2,3F)B(2F)B(3F)—O5
Cpd. No. 125: 3-P(3)B(2,3F)B(2F)B(3F)—O5
Cpd. No. 126: 1-H2B(3F)B(2F)B(3F)-3
Cpd. No. 127: 3-H2B(3F)B(2F)B(3F)-3
Cpd. No. 128: 5-H2B(3F)B(2F)B(3F)-3
Cpd. No. 129: 5-H2B(3F)B(2F)B(3F)—O4
Cpd. No. 130: F3-H2B(3F)B(2F)B(3F)-3
Cpd. No. 131: 2-H2B(2F)B(2F)B(3F)-4
Cpd. No. 132: 3-H2B(2F)B(2F)B(3F)-4
Cpd. No. 133: 4-H2B(2F)B(2F)B(3F)-4
Cpd. No. 134: 1O3-H2B(2F)B(2F)B(3F)-5
Cpd. No. 135: 2-H2B(2,3F)B(2F)B(3F)-3
Cpd. No. 136: 3-H2B(2,3F)B(2F)B(3F)-3
Cpd. No. 137: 5-H2B(2,3F)B(2F)B(3F)-3
Cpd. No. 138: 5-H2B(2,3F)B(2F)B(3F)-8

Cpd. No. 139: 3-H2B(2,3F)B(2F)B(3F)—O2
Cpd. No. 140: 3-H2B(2,3F)B(2F)B(3F)—O5
Cpd. No. 141: 3-H2B(2,3F)B(2F)B(3F)—O12
Cpd. No. 142: 2O—H2B(2,3F)B(2F)B(3F)-5
Cpd. No. 143: 4O—H2B(2,3F)B(2F)B(3F)-3
Cpd. No. 144: 4O1-H2B(2,3F)B(2F)B(3F)-3
Cpd. No. 145: 2O2-H2B(2,3F)B(2F)B(3F)-3
Cpd. No. 146: F2-H2B(2,3F)B(2F)B(3F)-4
Cpd. No. 147: F3-H2B(2,3F)B(2F)B(3F)-4
Cpd. No. 148: F5-H2B(2,3F)B(2F)B(3F)—O2
Cpd. No. 149: 5-Si(4)2B(2,3F)B(2F)B(3F)13 O3
Cpd. No. 150: 5-D(3,5)2B(2,3F)B(2F)B (3F)—O3
Cpd. No. 151: 3-B(2F)4BB(2F)B(3F)-4
Cpd. No. 152: 3O—B(2F)4BB(2F)B(3F)—O2
Cpd. No. 153: 2-B4B(2,3F)B(2F)B(3F)-3
Cpd. No. 154: 3-B4B(2,3F)B(2F)B(3F)-3
Cpd. No. 155: 3-B4B(2,3F)B(2F)B(3F)-5
Cpd. No. 156: 4-B4B(2,3F)B(2F)B(3F)—O2
Cpd. No. 157: 5-B4B(2,3F)B(2F)B(3F)—O3
Cpd. No. 158: F3-B4B(2,3F)B(2F)B(3F)—O2
Cpd. No. 159: F5-B4B(2,3F)B(2F)B(3F)—O2
Cpd. No. 160: 2-B(2,3F)4BB(2F)B(3F)-2
Cpd. No. 161: 2-B(2,3F)4BB(2F)B(3F)-3
Cpd. No. 162: 4-B(2,3F)4BB(2F)B(3F)-2
Cpd. No. 163: 4-B(2,3F)4BB(2F)B(3F)-3
Cpd. No. 164: 11-B(2,3F)4BB(2F)B(3F)—O1
Cpd. No. 165: 3O—B(2,3F)4BB(2F)B(3F)—O1
Cpd. No. 166: 3O—B(2,3F)4BB(2F)B(3F)—O3
Cpd. No. 167: 5O—B(2,3F)4BB(2F)B(3F)—O2
Cpd. No. 168: 5O—B(2,3F)4BB(2F)B(3F)—O4
Cpd. No. 169: 3O3-B(2,3F)4BB(2F)B(3F)—3
Cpd. No. 170: F2-B(2,3F)4BB(2F)B(3F)—O2
Cpd. No. 171: F3-B(2,3F)4BB(2F)B(3F)—O3
Cpd. No. 172: 3-H4B(2,3F)B(2F)B(3F)-2
Cpd. No. 173: 4-H4B(2,3F)B(2F)B(3F)-2
Cpd. No. 174: 5-H4B(2,3F)B(2F)B(3F)-2
Cpd. No. 175: 7-H4B(2,3F)B(2F)B(3F)-2
Cpd. No. 176: 10-H4B(2,3F)B(2F)B(3F)-2
Cpd. No. 177: 2-H4B(2,3F)B(2F)B(3F)—O3
Cpd. No. 178: 3-H4B(2,3F)B(2F)B(3F)—O3
Cpd. No. 179: 5-H4B(2,3F)B(2F)B(3F)—O3
Cpd. No. 180: F3-H4B(2,3F)B(2F)B(3F)—O3
Cpd. No. 181: F4-H4B(2,3F)B(2F)B(3F)—O3
Cpd. No. 182: F5-H4B(2,3F)B(2F)B(3F)—O3

Examples in which the compounds of the present invention were used as component of liquid crystal compositions are showm below. In each of Use Examples, NI indicates phase transition temperature (° C.) of nematic phase-isotropic phase, Δε: dielectric anisotropy value, Δn: optical anisotropy value, η: viscosity (mPa·s), Vth: threshold voltage (V), and VHR: voltage holding ratio (%).

In this connection, η was determined at 20° C., each of Δε, Δn, Vth and twist pitch was determined at 25° C., and VHR shows the values determined at 25° C., 80° C. or 100° C. from the left hand side in turn.

EXAMPLE 2 (USE EXAMPLE 1)

Liquid crystal composition (A) comprising the following cyanophenylcyclohexane type liquid crystal compounds in the amount shown below

| 3-HB—C | 24% |
| 5-HB—C | 36% |

-continued

| 7-HB—C | 25% |
| 5-HBB—C | 15% | had the following physical property values:

NI: 71.7, Δε: 11.0, Δn: 0.137, η: 26.7, Vth: 1.78

Physical property values of liquid crystal composition (B) comprising 85% of the liquid crystal composition (A) and 15% of the 3,3',3"-trifluoro-4,4"-dipropoxyterphenyl (Compound No. 1) obtained in Example 1 were as follows:

NI: 72.7, Δε: 10.7, Δn: 0.142, η: 29.3, Vth: 1.69

While this liquid crystal composition (B) was left in a freezer at −20° C., development of smectic phase and deposition of crystals were not observed even over 60 days.

EXAMPLE 3 (USE EXAMPLE 2)

Liquid crystal composition (C) comprising the following ester type liquid crystal compounds in the amount shown below

| 3-HEB—O2 | 17.2% |
| 3-HEB—O4 | 27.6% |
| 4-HEB—O2 | 20.7% |
| 5-HEB—O1 | 20.7% |
| 5-HEB—O2 | 13.8% | had the following physical property values:

NI: 74.0, Δε: −1.43

Physical property values of liquid crystal composition (D) comprising 95% of the liquid crystal composition (C) and 5% of the 3,3',3"-trifluoro-4,4"-dipropoxyterphenyl (Compound No. 1) obtained in Example 1 were as follows:

NI: 76.6, Δε: −1.53

While this liquid crystal composition (D) was left in a freezer at −20° C., development of smectic phase and deposition of crystals were not observed even over 60 days.

EXAMPLE 4

Preparation of 3,3'-difluoro-4'-(trans-4-propylcyclohexyl)-4-propoxybiphenyl (3-HB(2F)B (3F)—O3 (Compound No. 183))

(First step) Preparation of 3,3'-difluoro-4'-(1-hydroxy-4-propylcyclohexyl)-4-propoxybiphenyl To a solution of 15.0 g (60.4 mmol) of the 3,3'-difluoro-4-propoxybiphenyl obtained in the first step of Example 1 in 85 ml of THF was added by drops 70 ml (1.04M, cyclohexane solution, corresponding to 72.5 mmol) of sec-butyllithium while being maintained at a temperature lower than −60° C. After finishing of the dropping, it was stirred at the same temperature for 1 hour. Subsequently, a solution of 11.0 g (78.5 mmol) of 4-propylcyclohexanone in 55 ml of THF was added by drops thereto while being maintained at a temperature of −60° C., stirred at the same temperature for 3 hours, and then further stirred at room temperature for 2 hours. After 200 ml of a diluted hydrochloric acid was added by drops to the reaction liquid, it was extracted with 200 ml of toluene. The organic layer thus obtained was washed with a diluted aqueous sodium bicarbonate solution twice and with water thrice, and then dried over anhydrous magnesium sulfate. The solvent was distilled off under a reduced pressure, and the residue thus obtained was subjected to silica gel column chromatography (eluent: heptane/ethyl acetate=8/2) to obtain 21.2 g of a crude 3,3'-difluoro-4'-(1-hydroxy-4-propylcyclohexyl)-4-propoxybiphenyl. (Yield: 90.6%)

This product was used for next reaction without further purification.

(Second) Preparation of 3,3,'-difluoro-4'-(4-propyl-1-cyclohexenyl)-4-propoxybiphenyl A mixture of 21.2 g (54.6 mmol) of the 3,3'-difluoro-4'-(1-hydroxy-4-propylcyclohexyl)-4-propoxybiphenyl obtained in the previous step, 1.0 g of p-toluenesulfonic acid-monohydrate, and 200 ml of toluene was heated to reflux while the water, which was distilled off, being taken out for 2 hours. After finishing of the reaction, it was washed with a diluted aqueous sodium bicarbonate solution twice and with water thrice, and then dried over anhydrous magnesium sulfate. The solvent was distilled off under a reduced pressure, and the residue thus obtained was subjected to silica gel column chromatography (eluent: heptane/toluene= 3/1) to obtain 14.9 g of a crude 3,3'-difluoro-4'-(4-propyl-1-cyclohexenyl)-4-propoxybiphenyl. (Yield: 66.8%)

This product was used for next reaction without further purification.

(Third step) Preparation of 3,3'-difluoro-4'-(trans-4-propylcyclohexyl)-4-propoxybiphenyl The 3,3'-difluoro-4'-(trans-4-propylcyclohexenyl)-4-propoxybiphenyl obtained in the previous step in an amount of 14.9 g (40.2 mmol), 4.5 g of Raney nickel, and 100 ml of mixed solvent of toluene/ethanol (1/1) were mixed and subjected to hydrogenation. After absorption of hydrogen was terminated, the catalyst was filtered off. The solvent was distilled off under a reduced pressure, and the residue thus obtained was subjected to silica gel column chromatograph (eluent: heptane/toluene=7/3) to obtain 14.2 g of a crude 3,3'-difluoro-4'-(trans-4-propylcyclohexyl)-4-propoxybiphenyl. This product was recrystallized from mixed solvent of ethanol/ethyl acetate (7/3) to obtain 6.5 g of the subject compound. (Yield: 43.3%)

This compound exhibited a liquid crystal phase, and its phase transition temperatures were as follows:

C 78.4~78.9 N 144.2 Iso

Further, data of each spectrum well supported its structure.

Mass analysis: 372 (M+)

$^1$H-NMR (CDCl$_3$, TMS internal standard)

δ(ppm)

0.83–2.03 (m, 21H)

2.83 (t, 1H)

4.02 (t, 2H)

6.88–7.36 (m, 6H)

According to the method of Example 4, the following compounds can be synthesized:

Cpd. No. 184: 3-HB(2F)B(3F)—O3
Cpd. No. 185: 2-HB(2F)B(3F)-3
Cpd. No. 186: 4-HB(2F)B(3F)-3
Cpd. No. 187: 5-HB(2F)B(3F)-3
Cpd. No. 188: 11-HB(2F)B(3F)-2
Cpd. No. 189: 3-HB(2F)B(3F)—O2
Cpd. No. 190: 3-HB(2F)B(3F)—O5
Cpd. No. 191: 3-HB(2F)B(3F)—O9
Cpd. No. 192: 3O2-HB(2F)B(3F)-2
Cpd. No. 193: F2-HB(2F)B(3F)—O3
Cpd. No. 194: F3-HB(2F)B(3F)—O2
Cpd. No. 195: FF4-HB(2F)B(3F)—O2
Cpd. No. 196: 3(FF)1-HB(2F)B(3F)—O3
Cpd. No. 197: 3-D(2,5)B(2F)B(3F)-5
Cpd. No. 198: 3-D(2,5)B(2F)B(3F)—O3
Cpd. No. 199: 3-P(2)B(2F)B(3F)-2
Cpd. No. 200: 4-P(3)B(2F)B(3F)—O3
Cpd. No. 201: 5-Si(4)B(2F)B(3F)-2
Cpd. No. 202: 2-HHB(2F)B(3F)-4
Cpd. No. 203: 3-HHB(2F)B(3F)-3
Cpd. No. 204: 4-HHB(2F)B(3F)-2
Cpd. No. 205: 5-HHB(2F)B(3F)-2
Cpd. No. 206: 3O—HHB(2F)B(3F)-2
Cpd. No. 207: 5O—HHB(2F)B(3F)—O1
Cpd. No. 208: 1O4-HHB(2F)B(3F)-3
Cpd. No. 209: 3-HSi(1)B(2F)B(3F)—O2
Cpd. No. 210: 5-HD(2,5)B(2F)B(3F)—O2
Cpd. No. 211: 3-BHB(2F)B(3F)-3
Cpd. No. 212: 3-BHB(2F)B(3F)-5
Cpd. No. 213: 3-B(2,3F)HB(2F )B(3F )-2
Cpd. No. 214: 3-B(2,3F)HB(2F)B(3F)-5
Cpd. No. 215: 3-B(2,3F)HB(2F)B(3F)—O2
Cpd. No. 216: 5-B(2,3F)HB(2F)B(3F)—O3
Cpd. No. 217: 3O—B(2,3F)HB(2F)B(3F)-2
Cpd. No. 218: 5O—B(2,3F)HB(2F)B(3F)—O2
Cpd. No. 219: 18O—B(2,3F)HB(2F)B(3F)—O3
Cpd. No. 220: F8-B(2,3F)HB(2F)B(3F)-2
Cpd. No. 221: FF5-B(2,3F)HB(2F)B(3F)—O4
Cpd. No. 222: FFF3-B(2,3F)HB(2F)B(3F)—O3
Cpd. No. 223: F2O—B(2,3F)HB(2F)B(3F)—O2
Cpd. No. 224: 1-HB(2F)B(3F)H-3
Cpd. No. 225: 2-HB(2F)B(3F)H-5
Cpd. No. 226: 3-HB(2F)B(3F)H-5
Cpd. No. 227: F2-HB(2F)B(3F)H-2
Cpd. No. 228: F3-HB(2F)B(3F)H-5
Cpd. No. 229: F1O1-HB(2F)B(3F)H-4
Cpd. No. 230: 3(F)1-HB(2F)B(3F)H-3
Cpd. No. 231: 2O—HB(2F)B(3F)H-9
Cpd. No. 232: 5-P(3)B(2F)B(3F)P(2)-3
Cpd. No. 233: 3-Si(l)B(2F)B(3F)Si(4)-5
Cpd. No. 234: 3-HB(2F)B(3F)B(3F)-2
Cpd. No. 235: 5-HB(2F)B(3F)B(3F)—O2
Cpd. No. 236: 3-HB(2F)B(3F)B(2,3F)-3
Cpd. No. 237: 5-HB(2F)B(3F)B(2,3F)-3
Cpd. No. 238: 3-HB(2F)B(3F)B(2,3F)—O2
Cpd. No. 239: 5-HB(2F)B(3F)B(2,3F)—O2
Cpd. No. 240: 2(1)1-HB(2F)B(3F)B(2,3F)-3
Cpd. No. 241: 1(F)3-HB(2F)B(3F)B(2,3F)—O5
Cpd. No. 242: 2-H2HB(2F)B(3B)-3
Cpd. No. 243: 4-H2HB(2F)B(3B)-3
Cpd. No. 244: 5-H2HB(2F)B(3B)-8
Cpd. No. 245: 3O—H2HB(2F)B(3B)-5
Cpd. No. 246: 4O—H2HB(2F)B(3B)-3
Cpd. No. 247: 5O1-H2HB(2F)B(3B)—O2
Cpd. No. 248: 3-B(2F)2HB(2F)B(3F)-3
Cpd. No. 249: 5O—B(2F)2HB(2F)B(3F)—O3
Cpd. No. 250: 2-B(2,3F)2HB(2F)B(3F)-4
Cpd. No. 251: 3-B(2,3F)2HB(2F)B(3F)-5
Cpd. No. 252: 5-B(2,3F)2HB(2F)B(3F)—OCF$_2$CF$_2$H
Cpd. No. 253: 3O—B(2,3F)2HB(2F)B(3F)-3
Cpd. No. 254: 4O—B(2,3F)2HB(2F)B(3F)—O3
Cpd. No. 255: F4-B(2,3F)2HB(2F)B(3F)—O3
Cpd. No. 256: 3-HB(2F)B(3F)2B(2F)-4
Cpd. No. 257: 5-HB(2F)B(3F)2B(3F)-3
Cpd. No. 258: 4-HB(2F)B(3F)2B(3F)—O2
Cpd. No. 259: 2-HB(2F)B(3F)2B(2,3F)-5
Cpd. No. 260: 5-HB(2F)B(3F)2B(2,3F)-3
Cpd. No. 261: 3-HB(2F)B(3F)2B(2,3F)—O2
Cpd. No. 262: FF2(F)2-HB(2F)B(3F)2B(2,3F)—O3
Cpd. No. 263: 2(F)2-HB(2F)B(3F)2B(2,3F)—O3

CPd. No. 264: 1-H4HB(2F)B(3F)-3
Cpd. No. 265: 2-H4HB(2F)B(3F)-3
Cpd. No. 266: 5-H4HB(2F)B(3F)-3
Cpd. No. 267: 3-H4HB(2F)B(3F)—O2
Cpd. No. 268: 5-H4HB(2F)B(3F)—O2
Cpd. No. 269: 3-H4HB(2F)B(3F)—O3
Cpd. No. 270: 7-B4HB(2F)B(3F)-2
Cpd. No. 271: 3O—B(2,3F)4HB(2F)B(3F)—O2
Cpd. No. 272: 4-HB(2F)B(3F)4B(2,3F)-3
Cpd. No. 273: 11-HB(2F)B(3F)4B(2,3F)-2
Cpd. No. 274: 3-HB(2F)B(3F)4B(2,3F)—O5
Cpd. No. 275: F7-HB(2F)B(3F)4B(2,3F)—O3

EXAMPLE 5 (USE EXAMPLE 3)

Physical property values of liquid crystal composition (E) comprising 85% of the liquid crystal composition (C) in Example 3 and 15% of the 3,3'-difluoro-4'-(trans-4-propylcyclohexyl)-4-propoxybiphenyl (Compound No. 183) obtained in Example 4 were as follows:

NI: 81.7, Δε: −1.54

While this liquid crystal composition (E) was left in a freezer at −20° C., development of smectic phase or separation of crystals was not observed even over 60 days.

EXAMPLE 6

Preparation of 3,3'-difluoro-4'-((trans-4-propylcyclohexyl)methoxy)-4-propoxybiphenyl (3-HCH₂OB(2F)B(3F)—O3 (Compound No. 276))

(First step) Preparation of 3,3'-difluoro-4'-hydroxy-4-propoxybiphenyl

First, 10.0 g (32.4 mmol) of 3,3'-difluoro-4'-methoxymethoxy-4-propoxybiphenyl [which was obtained by cross-coupling reaction of 3-fluoro-4-methoxymethoxybromobenzene with dihydroxy(3-fluoro-4-propoxyphenyl)borane in the presence of Pd catalyst], 50 ml of methanol, and 10 ml of a concentrated hydrochloric acid were heated to reflux for 3 hours. Then, 50 ml of water was added to the reaction solution and extracted with 150 ml of diethyl ether. The organic layer thus obtained was washed with a diluted aqueous sodium bicarbonate solution twice and with water thrice, and then dried over anhydrous magnesium sulfate. The solvent was distilled off under a reduced pressure to obtain 8.5 of a crude 3,3'-difluoro-4'- hydroxy-4-propoxybiphenyl. (Yield: 99.8%)

This product was used for next reaction without further purification.

(Second step) Preparation of 3,3'-difluoro-4'-((trans-4-propylcyclohexyl)methoxy)-propoxybiphenyl In a mixture of 0.7 g (60% oiliness, corresponding to 18.2 mmol) of sodium hydride and 5 ml of dimethyl formamide (DMF) was added by drops a solution of 4.0 g (15.1 mmol) of the 3,3'-difluoro-4'-hydroxy-4-propoxybiphenyl obtained in the previous step in 20 ml of DMF at room temperature, and then stirred at the same temperature for 1 hour. Subsequently, a solution of 6.0 g (22.7 mmol) of trans-4-propyl-1-iodomethylcyclohexane in 20 ml of DMF was added by drops to the reaction solution at room temperature, stirred at the same temperature for 1 hour, and then heated to reflux for 3 hours. After finishing of the reaction, the reaction solution was poured into 50 ml of a diluted hydrochloric acid and then extracted with 150 ml of toluene. The organic layer thus obtained was washed with a diluted aqueous sodium hydroxide solution thrice and with water thrice, and then dried over anhydrous magnesium sulfate. The solvent was distilled off under a reduced pressure, and the residue thus obtained was subjected to silica gel column chromatography (eluent: heptane/toluene=7/3) to obtain 2.3 g of a crude 3,3'-difluoro-4'-((trans-4-propylcyclohexyl)methoxy)-4-propoxybiphenyl. This product was recrystallized from mixed solvent of ethanol/ethyl acetate (7/3) to obtain 1.8 g of the subject compound. (Yield: 48.2%)

This compound exhibited a liquid crystal phase, and its phase transition temperatures were as follows:

C 86.6~87.0 N 126.8 Iso

Further, data of each spectrum well supported its structure.

Mass analysis: 402 (M+)

$^1$H-NMR (CDCl₃, TMS internal standard)

δ (ppm)

0.81–1.98 (m, 22H)

3.85 (d, 2H)

4.02 (t, 2H)

6.88–7.31 (m, 6H)

According to the method of Example 6, the following compounds can be synthesized. Physical property values shown below are ones of compositions determined according to the method of Example 3.

Cpd. No. 277: 2-HCH₂OB(2F)B(3F)-3
Cpd. No. 278: 2-HCH₂OB(2F)B(3F)-5
Cpd. No. 279: 3-HCH₂OB(2F)B(3F)-5
Cpd. No. 280: 5-HCH₂OB(2F)B(3F)-3
Cpd. No. 281: 8-HCH₂OB(2F)B(3F)-13
Cpd. No. 282: 2-HCH₂OB(2F)B(3F)—O2
Cpd. No. 283: 4-HCH₂OB(2F)B(3F)—O2
Cpd. No. 284: 4-HCH₂OB(2F)B(3F)—O3
Cpd. No. 285: 5-HCH₂OB(2F)B(3F)—O3
Cpd. No. 286: 3O—HCH₂OB(2F)B(3F)-2
Cpd. No. 287: 5O1-HCH₂OB(2F)B(3F)—CF₂CFHCF₃
Cpd. No. 288: F5-HCH₂OB(2F)B(3F)-2
Cpd. No. 289: F3-HCH₂OB(2F)B(3F)-2F
Cpd. No. 290: FF2-HCH₂OB(2F)B(3F)-5
Cpd. No. 291: FFF3-HCH₂B(2F)B(3F)-4
Cpd. No. 292: 3(F)1-HCH₂OB(2F)B(3F)-3
Cpd. No. 293: 5-D(2,5)CH₂OB(2F)B(3F)—O2
Cpd. No. 294: 5-Si(4)CH₂OB(2F)B(3F)—O3
Cpd. No. 295: 5-HOCH₂B(2F)B(3F)-3
Cpd. No. 296: 3-HOCH₂B(2F)B(3F)-2
Cpd. No. 297: 3-HOCH₂B(2F)B(3F)—O3
Cpd. No. 298: 5-HOCH₂B(2F)B(3F)—O3
Cpd. No. 299: 3-BCH₂OB(2F)B(3F)-2
Cpd. No. 300: 3-BCH₂OB(2F)B(3F)-5
Cpd. No. 301: 13-BCH₂OB(2F)B(3F)-15
Cpd. No. 302: 4-BCH₂OB(2F)B(3F)—O2
Cpd. No. 303: 5-BCH₂OB(2F)B(3F)—O3
Cpd. No. 304: F2-BCH₂OB(2F)B(3F)-3
Cpd. No. 305: F3-BCH₂OB(2F)B(3F)—O5
Cpd. No. 306: FF4-BCH₂OB(2F)B(3F)—O2
Cpd. No. 307: 2-BOCH₂B(2F)B(3F)-3
Cpd. No. 308: 4-BOCH₂B(2F)B(3F)-4
Cpd. No. 309: 7-BOCH₂B(2F)B(3F)—O2
Cpd. No. 310: 10-BOCH₂B(2F)B(3F)-2F
Cpd. No. 311: 2O4-BOCH₂B(2F)B(3F)—O3
Cpd. No. 312: F4-BOCH₂B(2F)B(3F)-2F
Cpd. No. 313: 2-B(3F)CH₂OB(2F)B(3F)-2
Cpd. No. 314: 4-B(3F)CH₂OB(2F)B(3F)—O3
Cpd. No. 315: 3-B(3F)OCH₂B(2F)B(3F)-2
Cpd. No. 316: 5-B(3F)OCH₂B(2F)B(3F)—O2
Cpd. No. 317: 5-B(2F)CH₂OB(2F)B(3F)-2
Cpd. No. 318: 3O—B(2F)CH₂OB(2F)B(3F)—O2
Cpd. No. 319: 7-B(2F)OCH₂B(2F)B(3F)-2

Cpd. No. 320: 2O—B(2F)OCH$_2$B(2F)B(3F)—O4
Cpd. No. 321: 1O3-B(2F)OCH$_2$B(2F)B(3F)—O5
Cpd. No. 322: 3-B(2,3F)CH$_2$OB(2F)B(3F)-2
Cpd. No. 323: 5-B(2,3F)CH$_2$OB(2F)B(3F)-4
Cpd. No. 324: 7-B(2,3F)CH$_2$OB(2F)B(3F)-13
Cpd. No. 325: 2O—B(2,3F)CH$_2$OB(2F)B(3F)-3
Cpd. No. 326: 4O—B(2,3F)CH$_2$OB(2F)B(3F)-3
Cpd. No. 327: 3O—B(2,3F)CH$_2$OB(2F)B(3F)—O2
Cpd. No. 328: 1O3-B(2,3F)CH$_2$OB(2F)B(3F)-2
Cpd. No. 329: 3O1-B(2,3F)CH$_2$OB(2F)B(3F)-3
Cpd. No. 330: F3O—B(2,3F)CH$_2$OB(2F)B(3F)-2
Cpd. No. 331: F4O—B(2,3F)CH$_2$OB(2F)B(3F)-3
Cpd. No. 332: 2-B(2,3F)OCH$_2$B(2F)B(3F)-1
cpd. No. 333: 3-B(2,3F)OCH$_2$B(2F)B(3F)-2
Cpd. No. 334: 3-B(2,3F)OCH$_2$B(2F)B(3F)-4
Cpd. No. 335: 3-B(2,3F)OCH$_2$B(2F)B(3F)-5
Cpd. No. 336: 3O—B(2,3F)OCH$_2$B(2F)B(3F)-2
Cpd. No. 337: 5O—B(2,3F)OCH$_2$B(2F)B(3F)-2
Cpd. No. 338: 2O—B(2,3F)OCH$_2$B(2F)B(3F)—O3
Cpd. No. 339: 3O—B(2,3F)OCH$_2$B(2F)B(3F)—O4
Cpd. No. 340: 2O4-B(2,3F)OCH$_2$B(2F)B(3F)-1
Cpd. No. 341: 8O8-B(2,3F)OCH$_2$B(2F)B(3F)-2
Cpd. No. 342: F2-B(2,3F)OCH$_2$B(2F)B(3F)-7
Cpd. No. 343: F5-B(2,3F)OCH$_2$B(2F)B(3F)-3
Cpd. No. 344: FF3-B(2,3F)OCH$_2$B(2F)B(3F)-2
Cpd. No. 345: FFF4-B(2,3F)OCH$_2$B(2F)B(3F)-3
Cpd. No. 346: 3-BBCH$_2$OB(2F)B(3F)-2
Cpd. No. 347: 5-BBCH$_2$OB(2F)B(3F)-3
Cpd. No. 348: 7-BBCH$_2$OB(2F)B(3F)-11
Cpd. No. 349: 2-BBCH$_2$OB(2F)B(3F)—O3
Cpd. No. 350: 3-BBCH$_2$OB(2F)B(3F)—O12
Cpd. No. 351: 4-BBOCH$_2$B(2F)B(3F)-3
Cpd. No. 352: 9-BBOCH$_2$B(2F)B(3F)-2
Cpd. No. 353: 5-BBOCH$_2$B(2F)B(3F)—O4
Cpd. No. 354: F3-BBOCH$_2$B (2F) B(3 F)—O2
Cpd. No. 355: 3(F)2-BBOCH$_2$B(2F)B(3F)-4
Cpd. No. 356: 3(FF)1-BBOCH$_2$B(2F)B(3F)—O3
Cpd. No. 357: 2-B(2,3F)BCH$_2$OB(2F)B(3F)-3
cpd. No. 358: 5-B(2,3F)BCH$_2$OB(2F)B(3F)-3
Cpd. No. 359: 16-B(2,3F)BCH$_2$OB(2F)B(3F)-2
Cpd. No. 360: 3O—B(2,3F)BCH$_2$OB(2F)B(3F)-2
Cpd. No. 361: 5O—B(2,3F)BCH$_2$OB(2F)B(3F)-3
Cpd. No. 362: 17O—B(2,3F)BCH$_2$OB(2F)B(3F)-2
Cpd. No. 363: 4O—B(2,3F)BCH$_2$OB(2F)B(3F)—O3
Cpd. No. 364: 2O—B(2,3F)BOCH$_2$B(2F)B(3F)-3
Cpd. No. 365: 3O—B(2,3F)BOCH$_2$B(2F)B(3F)—OCF$_2$CF$_2$H
Cpd. No. 366: 3-BB(2,3F)CH$_2$OB(2F)B(3F)-2
Cpd. No. 367: 5-BB(2,3F)CH$_2$OB(2F)B(3F)—O2
Cpd. No. 368: 2-BB(2,3F)OCH$_2$B(2F)B(3F)-5
Cpd. No. 369: 3-BB(2,3F)OCH$_2$B(2F)B(3F)—O3
Cpd. No. 370: 5-B(2,3F)CH$_2$OB(2F)B(3F)B-3
Cpd. No. 371: 7-B(2,3F)CH$_2$OB(2F)B(3F)B-2
Cpd. No. 372: 7-B(2,3F)CH$_2$OB(2F)B(3F)B-2F
Cpd. No. 373: 3O—B(2,3F)CH$_2$OB(2F)B(3F)B-2
Cpd. No. 374: 4O—B(2,3F)CH$_2$OB(2F)B(3F)B-3F
Cpd. No. 375: F4-B(2,3F)CH$_2$OB(2F)B(3F)B-2F
Cpd. No. 376: 3-BCH$_2$OB(2F)B(3F)B(2,3F)-2
Cpd. No. 377: 4-BCH$_2$OB(2F)B(3F)B(2,3F)-3
Cpd. No. 378: 5-BCH$_2$OB(2F)B(3F)B(2,3F)—O2
Cpd. No. 379: FF2-BCH$_2$OB(2F)B(3F)B(2,3F)—O3
Cpd. No. 380: 3(F)1-BCH$_2$OB(2F)B(3F)B(2,3F)—O5
Cpd. No. 381: 2-BCH$_2$OB(2F)B(3F)B(2,3F)—O3
Cpd. No. 382: 3O—B(2,3F)CH$_2$OB(2F)B(3F)B(2,3F)—O1
Cpd. No. 383: 3-HHCH$_2$OB(2F)B(3F)—O3
NI: 88.9, Δε: -1.57
Cpd. No. 384: 5-HHCH$_2$OB(2F)B(3F)-2

Cpd. No. 385: 5-HHCH$_2$OB(2F)B(3F)-3
Cpd. No. 386: 7-HHCH$_2$OB(2F)B(3F)—O1
Cpd. No. 387: 4O2-HHCH$_2$OB(2F)B(3F)—O2
Cpd. No. 388: 4(FF)1-HHCH$_2$OB(2F)B(3F)-1
Cpd. No. 389: 5-D(3,5)HCH$_2$OB(2F)B(3F)—O2
Cpd. No. 390: 5-HSi(1)CH$_2$OB(2F)B(3F)—O3
Cpd. No. 391: 5-HBCH$_2$OB(2F)B(3F)-2
Cpd. No. 392: 3-HB(2,3F)CH$_2$OB(2F)B(3F)-2
Cpd. No. 393: 5-HB(2,3F)CH$_2$OB(2F)B(3F)-3
Cpd. No. 394: 8-HB(2,3F)CH$_2$OB(2F)B(3F)-3
Cpd. No. 395: 14-HB(2,3F)CH$_2$OB(2F)B(3F)-5
Cpd. No. 396: 2-HB(2,3F)CH$_2$OB(2F)B(3F)—O2
Cpd. No. 397: 3-HB(2,3F)CH$_2$OB(2F)B(3F)—O2
Cpd. No. 398: 5-HB(2,3F)CH$_2$OB(2F)B(3F)—O3
Cpd. No. 399: F9-HB(2,3F)CH$_2$OB(2F)B(3F)-2
Cpd. No. 400: 3-HB(2,3F)OCH$_2$B(2F)B(3F)-2
Cpd. No. 401: 5-HB(2,3F)OCH$_2$B(2F)B(3F)—O2
Cpd. No. 402: 2O—B(2,3F)HCH$_2$OB(2F)B(3F)-3
Cpd. No. 403: 5O—B(2,3F)OCH$_2$B(2F)B(3F)—O3
Cpd. No. 404: 3-B(2,3F)CH$_2$OB(2F)B(3F)H-3
Cpd. No. 405: 3O—B(2,3F)CH$_2$OB(2F)B(3F)H-2
Cpd. No. 406: 5O—B(2,3F)CH$_2$OB(2F)B(3F)H-3F
Cpd. No. 407: 8O—B(2,3F)CH$_2$OB(2F)B(3F)H-1O2
Cpd. No. 408: 4-HCH$_2$OB(2F)B(3F)B(3F)—O3
Cpd. No. 409: 5-HCH$_2$OB(2F)B(3F)B(2,3F)-3
Cpd. No. 410: 3-HCH$_2$OB(2F)B(3F)B(2,3F)—O5
Cpd. No. 411: F4-HCH$_2$OB(2F)B(3F)B(2,3F)—O2
Cpd. No. 412: 3(F)1-HCH$_2$OB(2F)B(3F)B(2,3F)—O3
Cpd. No. 413: 2-HCH$_2$OB(2F)B(3F)B(2,3F)—O4
Cpd. No. 414: 2-HCH$_2$OB(2F)B(3F)H-3
Cpd. No. 415: 5-HCH$_2$OB(2F)B(3F)H-3
Cpd. No. 416: 12-HCH$_2$OB(2F)B(3F)H-2
Cpd. No. 417: FF3-HCH$_2$OB(2F)B(3F)H-4F
Cpd. No. 418: FFF4-HCH$_2$OB(2F)B(3F)H-3F

EXAMPLE 7 (USE EXAMPLE 4)

Physical property values of liquid crystal composition (F) comprising 85% of the liquid crystal composition (C) in Example 3 and 15% of the 3,3'-difluoro-4-((trans-4-propylcyclohexyl)-methoxy)-4-propoxybiphenyl ( Compound No. 276) were as follows:

NI: 80.8, Δε: -1. 77

While this liquid crystal composition (F) was left in a freezer at -20° C., development of smectic phase and deposition of crystals were not observed even over 60 days.

EXAMPLE 8

Preparation of 3,3'-difluoro-4'-(2-(3-fluoro-4-methoxyphenyl)ethyl-4-propoxybiphenyl (1O—B(2F)2B(2F)B(3F)—O3 (Compound No. 419))

(First step) Preparation of 3,3'-difluoro-4'-(2-(3-fluoro-4-methoxyphenyl)vinyl)-4-propoxybiphenyl In a mixture of 11.7 g (23.5 mmol) of 3-fluoro-4-methoxy-benzyltriphenylphosphonium bromide [which was obtained by reacting with triphenylphosphine after having been passed through the reaction of a Grignard reagent, which was prepared from 3-fluoro-4-methoxybromobenzene and Mg in advance, with formaldehyde, and halogenation reaction] and 30 ml of THF was added 1.3 g (23.5 mmol) of sodium methoxide while being cooled with ice, and then stirred at the same temperature for 1 hour. To the reaction mixture was added by drops a solution of 5.0 g (18.1 mmol) of the 3,3'-difluoro-4'-formyl-4-propoxybiphenyl, [which was obtained by lithiating the 3,3'-difluoro-4-propoxybiphenyl obtained in the first step of Example 1 with sec-butyllithium, and then reacting with piperidine-1-carbaldehyde] in 25 ml of THF while being maintained at a temperature −60° C. or lower, and stirred at the same temperature for 2 hours. After finishing of the reaction, 30 ml of a diluted hydrochloric acid was added to the reaction mixture, and then extracted with 200 ml of toluene. The organic layer thus obtained was washed with a diluted aqueous sodium bicarbonate solution twice and with water thrice, and then dried over anhydrous magnesium sulfate. The solvent was distilled off under a reduced pressure, and the residue thus obtained was subjected to silica gel column chromatography (eluent: toluene) to obtain 4.6 g of a crude 3,3'-difluoro-4'-(2-(3-fluoro-4-methoxyphenyl)vinyl)-4-propoxybiphenyl. (Yield: 63.8%)

This product was used for next reaction without further purification.

(Second step) Preparation of 3,3'-difluoro-4'-(2-(3-fluoro-4-methoxyphenyl)ethyl)-4-propoxybiphenyl The 3,3'-difluoro-4'-(2-(3-fluoro-4-methoxyphenyl) vinyl)-4-propoxybiphenyl obtained in the previous step in an amount of 4.6 g (11.5 mmol), 0.2 g of 5%Pd—C, and 50 ml of mixed solvent of toluene/ethanol (1/1) were mixed and subjected to hydrogenation. After absorption of hydrogen was terminated, the catalyst was filtered off. The solvent was distilled off under a reduced pressure, and the residue thus obtained was subjected to silica gel column chromatography (eluent: heptane/toluene=6/4) to obtain 3.8 g of a crude 3,3'-difluoro-4'-(2-(3-fluoro-4-methoxyphenyl)ethyl)-4-propoxybiphenyl. This product was recrystallized from mixed solvent of ethanol/ethyl acetate (8/2) to obtain 1.9 g of the subject compound. (Yield: 41.3%)

According to the method of Example 8, the following compounds can be synthesized:

Cpd. No. 420: 5-B(2F)2B(2F)B(3F)-1
Cpd. No. 421: 14-B(2F)2B(2F)B(3F)-3
Cpd. No. 422: 4O—B(2F)2B(2F)B(3F)-10
Cpd. No. 423: 5O—B(2F)2B(2F)B(3F)-2
Cpd. No. 424: 5O1-B(2F)2B(2F)B(3F)—O2
Cpd. No. 425: F4O—B(2F)2B(2F)B(3F)-3
Cpd. No. 426: 3-B(2F)2B(2F)B(3F)—O3
Cpd. No. 427: 3-B(2,3F)2B(2F)B(3F)-2
Cpd. No. 428: 5-B(2,3F)2B(2F)B(3F)-3
Cpd. No. 429: 3O—B(2,3F)2B(2F)B(3F)-4
Cpd. No. 430: 5O—B(2,3F)2B(2F)B(3F)—O2
Cpd. No. 431: 1O5-B(2,3F)2B(2F)B(3F)-3
Cpd. No. 432: 2-H2B(2F)B(3F)-3
Cpd. No. 433: 3-H2B(2F)B(3F)-3
Cpd. No. 434: 4-H2B(2F)B(3F)-3
Cpd. No. 435: 5-H2B(2F)B(3F)-3
Cpd. No. 436: 7-H2B(2F)B(3F)-2
Cpd. No. 437: 14-H2B(2F)B(3F)-2
Cpd. No. 438: 5-H2B(2F)B(3F)—O3
Cpd. No. 439: 5-H2B(2F)B(3F)—O4
Cpd. No. 440: 7-H2B(2F)B(3F)—O1
Cpd. No. 441: 1O7-H2B(2F)B(3F)-2
Cpd. No. 442: F2-H2B(2F)B(3F)—OCF$_2$CFHCF$_3$
Cpd. No. 443: 1(F)3-H2B(2F)B(3F)—O3
Cpd. No. 444: 4-Si(1)2B(2F)B(3F)-3
Cpd. No. 445: 1-BB(2,3F )2B(2F)B(3F)-2
Cpd. No. 446: 2-BB(2,3F)2B(2F)B(3F)-3
Cpd. No. 447: 3-BB(2,3F)2B(2F)B(3F)-5
Cpd. No. 448: 5-BB(2,3F)2B(2F)B(3F)—O2
Cpd. No. 449: 3-B(2,3F)B2B(2F)B(3F)-2
Cpd. No. 450: 4-B(2,3F)B2B(2F)B(3F)-3
Cpd. No. 451: 5-B(2,3F)B2B(2F)B(3F)-2
Cpd. No. 452: 2O—B(2,3F)B2B(2F)B(3F)-3
Cpd. No. 453: 4O—B(2,3F)B2B(2F)B(3F)-3
Cpd. No. 454: 5O—B(2,3F)B2B(2F)B(3F)—O2
Cpd. No. 455: 5O1-B(2,3F)B2B(2F)B(3F)O5
Cpd. No. 456: 3-B(2,3F)B(2,3F)2B(2F)B(3F)-2
Cpd. No. 457: 5O—B(2,3F)B(2,3F)2B(2F)B(3F)—O1
Cpd. No. 458: 3-HB(2,3F)2B(2F)B(3F)-2
Cpd. No. 459: 4-HB(2,3F)2B(2F)B(3F)-3
Cpd. No. 460: 5-HB(2,3F)2B(2F)B(3F)—O2
Cpd. No. 461: 2-HH2B(2F)B(3F)-1
Cpd. No. 462: 3-HH2B(2F)B(3F)-2
Cpd. No. 463: 5-HH2B(2F)B(3F)-2
Cpd. No. 464: 7-HH2B(2F)B(3F)-8
Cpd. No. 465: 13-HH2B(2F)B(3F)-3
Cpd. No. 466: 4-HH2B(2F)B(3F)—O3
Cpd. No. 467: 5-HH2B(2F)B(3F)—O3
Cpd. No. 468: 8-HH2B(2F)B(3F)—O3
Cpd. No. 469: F2-HH2B(2F)B(3F)—O4
Cpd. No. 470: FF4-HH2B(2F)B(3F)13 O2
Cpd. No. 471: 7(F)1-HH2B(2F)B(3F)-3
Cpd. No. 472: 3-Si(4)Si(4)2B(2F)B(3F)-5
Cpd. No. 473: 3-H2B(2F)B(3F)H-8
Cpd. No. 474: 4-H2B(2F)B(3F)H-3
Cpd. No. 475: 7-H2B(2F)B(3F)H-2
Cpd. No. 476: 1O4-H2B(2F)B(3F)H-5
Cpd. No. 477: 3O3-H2B(2F)B(3F)H—O2
Cpd. No. 478: 3-H2B(2F)B(3F)B(3F)-4
Cpd. No. 479: 4-H2B(2F)B(3F)B(3F)-2
Cpd. No. 480: 5-H2B(2F)B(3F)B(3F)—O3
Cpd. No. 481: 2-H2B(2F)B(3F)B(2,3F)-4
Cpd. No. 482: 3-H2B(2F)B(3F)B(2,3F)-2
Cpd. No. 483: 5-H2B(2F)B(3F)B(2,3F)-3
Cpd. No. 484: 5-H2B(2F)B(3F)B(2,3F)—O2
Cpd. No. 485: 5-H2B(2F)B(3F)B(2,3F)—O3
Cpd. No. 486: F4-H2B(2F)B(3F)B(2,3F)—O2
Cpd. No. 487: F11-H2B(2F)B(3F)B(2,3F)—O2
Cpd. No. 488: 2-H4B(2F)B(3F)-3
Cpd. No. 489: 4-H4B(2F)B(3F)-3
Cpd. No. 490: 7-H4B(2F)B(3F)-2
Cpd. No. 491: 5O1-H4B(2F)B(3F)-2
Cpd. No. 492: F4 -H4B(2F)B(3F)—OCF$_2$CF$_2$H
Cpd. No. 493: 2-H4B(2F)B(3F)—O2
Cpd. No. 494: 3O—B(2,3F)4B(2F)B(3F)—O2
Cpd. No. 495: 5O—B(2,3F)4B(2F)B(3F)—O3
Cpd. No. 496: F2O—B(2,3F)4B(2F)B(3F)-3
Cpd. No. 497: 3-BB(2,3F)4B(2F)B(3F)-7
Cpd. No. 498: 5-BB(2,3F)4B(2F)B(3F)—O2
Cpd. No. 499: 2-B(2,3F)B4B(2F)B(3F)-4
Cpd. No. 500: 3O—B(2,3F)B4B(2F)B(3F)—O4
Cpd. No. 501: 3-HH4B(2F)B(3F)-2
Cpd. No. 502: 4-HH4B(2F)B(3F)-3
Cpd. No. 503: 5-HH4B(2F)B(3F)—O2
Cpd. No. 504: 8-HH4B(2F)B(3F)—O3

EXAMPLE 9 (USE EXAMPLE 5)

Physical property values of the liquid crystal composition of Composition Example 1 were as follows:

NI: 80.8, Δε: −1.8, Δn: 0.096, η: 27.8

While this liquid crystal composition was left in a freezer at −20° C., development of smectic phase and deposition of crystals were not observed even over 60 days.

EXAMPLE 10 (USE EXAMPLE 6)

Physical property values of the liquid crystal composition of Composition Example 2 were as follows:

NI: 81.7, Δε: −1.5, Δn: 0.099, η: 23.9

While this liquid crystal composition was left in a freezer at −20° C., development of smectic phase and deposition of crystals were not observed even over 60 days.

EXAMPLE 11 (USE EXAMPLE 7)

Physical property values of the liquid crystal composition of Composition Example 3 were as follows:

NI: 81.1, Δε: −3.9, Δn: 0.092

While this liquid crystal composition was left in a freezer at −20° C., development of smectic phase and deposition of crystals were not observed even over 60 days.

EXAMPLE 12 (USE EXAMPLE 8)

Physical property values of the liquid crystal composition of Composition Example 4 were as follows:

NI: 87.3, Δε: −3.5, Δn: 0.080

While this liquid crystal composition was left in a freezer at −20° C., development of smectic phase and deposition of crystals were not observed even over 60 days.

EXAMPLE 13 (USE EXAMPLE 9)

Physical property values of the liquid crystal composition of Composition Example 5 were as follows:

NI: 73.0, Δε: −3.4, Δn: 0.196, VHR: 98.3, 97.4, 96.9

While this liquid crystal composition was left in a freezer at −20° C., development of smectic phase and deposition of crystals were not observed even over 60 days.

EXAMPLE 14 (USE EXAMPLE 10)

Physical property values of the liquid crystal composition of Composition Example 6 were as follows:

NI: 71.9, Δε: −2.8, Δn: 0.149

While this liquid crystal composition was left in a freezer at −20° C., development of smectic phase and deposition of crystals were not observed even over 60 days.

EXAMPLE 15 (USE EXAMPLE 11)

Physical property values of the liquid crystal composition of Composition Example 7 were as follows:

NI: 83.1, Δε: 0.139, η: 28.6

While this liquid crystal composition was left in a freezer at −20° C., development of smectic phase and deposition of crystals were not observed even over 60 days.

EXAMPLE 16 (USE EXAMPLE 12)

Physical property values of the liquid crystal composition of Composition Example 8 were as follows:

NI: 81.0, Δε: 0.211

While this liquid crystal composition was left in a freezer at −20° C., development of smectic phase and deposition of crystals were not observed even over 60 days.

EXAMPLE 17 (USE EXAMPLE 13)

Physical property values of the liquid crystal composition of Composition Example 9 were as follows:

NI: 73.3, Δε: −3.9, Δn: 0.131

While this liquid crystal composition was left in a freezer at −20° C., development of smectic phase and deposition of crystals were not observed even over 60 days.

EXAMPLE 18 (USE EXAMPLE 14)

Physical property values of the liquid crystal composition of Composition Example 10 were as follows:

NI: 64.2, Δε: −5.6, Δn: 0.078, η: 43.8, Vth: 2.03

While this liquid crystal composition was left in a freezer at −20° C., development of smectic phase and deposition of crystals were not observed even over 60 days.

EXAMPLE 19 (USE EXAMPLE 15)

Physical property values of the liquid crystal composition of Composition Example 11 were as follows:

NI: 87.2, Δε: 7.3, Δn: 0.166, η: 19.8, Vth: 2.04

When 0.8 part by weight of optically active compound CM-33 was dissolved in 100 parts by weight of the liquid crystal composition of Composition Example 11, the pitch of the composition thus obtained was 10.6 μm.

While this liquid crystal composition was left in a freezer at −20° C., development of smectic phase and deposition of crystals were not observed even over 60 days.

EXAMPLE 20 (USE EXAMPLE 16)

Physical property values of the liquid crystal composition of Composition Example 12 were as follows:

NI: 90.8, Δε: 6.3, Δn: 0.206, η: 37.8, Vth: 2.28

While this liquid crystal composition was left in a freezer at −20° C., development of smectic phase and deposition of crystals were not observed even over 60 days.

EXAMPLE 21 (USE EXAMPLE 17)

Physical property values of the liquid crystal composition of Composition Example 13 were as follows:

NI: 72.9, Δε: 23.8, Δn: 0.120, η: 39.9, Vth: 0.99

While this liquid crystal composition was left in a freezer at −20° C., development of smectic phase and deposition of crystals were not observed even over 60 days.

EXAMPLE 22 (USE EXAMPLE 18)

Physical property values of the liquid crystal composition of Composition Example 14 were as follows:

NI: 86.2, Δε: 4.5, Δn: 0.119, η: 19.8, Vth: 2.43

While this liquid crystal composition was left in a freezer at −20° C., development of smectic phase and deposition of crystals were not observed even over 60 days.

EXAMPLE 23 (USE EXAMPLE 18)

Physical property values of the liquid crystal composition of Composition Example 15 were as follows:

NI: 95.8, Δε: 6.8, Δn: 0.210, η: 17.5, Vth: 2.10

While this liquid crystal composition was left in a freezer at −20° C., development of smectic phase and deposition of crystals were not observed even over 60 days.

EXAMPLE 24 (USE EXAMPLE 19)

Physical property values of the liquid crystal composition of Composition Example 16 were as follows:

NI: 80.1, Δε: 6.1, Δn: 0.133, η: 14.6. Vth: 2.14

While this liquid crystal composition was left in a freezer at −20° C., development of smectic phase and deposition of crystals were not observed even over 60 days.

EXAMPLE 25 (USE EXAMPLE 20)

Physical property values of the liquid crystal composition of Composition Example 17 were as follows:

NI: 86.7, Δε: 3.2, Δn: 0.096, η: 20.1, Vth: 2.67

Pitch of the liquid crystal composition prepared by dissolving 0.3 part by weight of optically active compound CN to 100 parts by weight of the liquid crystal composition of Composition Example 17 was 77 μm.

While this liquid crystal composition was left in a freezer at −20° C., development of smectic phase and deposition of crystals were not observed even over 60 days.

EXAMPLE 26 (USE EXAMPLE 21)

Physical property values of the liquid crystal composition of Composition Example 18 were as follows:

NI: 76.8, Δε: 12.8, Δn: 0.089, η: 35.4, Vth: 1.46

While this liquid crystal composition was left in a freezer at −20° C., development of smectic phase and deposition of crystals were not observed even over 60 days.

EXAMPLE 27 (USE EXAMPLE 22)

Physical property values of the liquid crystal composition of Composition Example 19 were as follows:

NI: 89.0, Δε: 4.7, Δn: 0.131, η: 22.3, Vth: 2.36

While this liquid crystal composition was left in a freezer at −20° C., development of smectic phase and deposition of crystals were not observed even over 60 days.

EXAMPLE 28 (USE EXAMPLE 23)

Physical property values of the liquid crystal composition of Composition Example 20 were as follows:

NI: 83.5, Δε: 4.3, Δn: 0.095, η: 17.4, Vth: 2.43

While this liquid crystal composition was left in a freezer at −20° C., development of smectic phase and deposition of crystals were not observed even over 60 days.

EXAMPLE 29 (USE EXAMPLE 24)

Physical property values of the liquid crystal composition of Composition Example 21 were as follows:

NI: 75.3, Δε: 7.8, Δn: 0.097, η: 26.2, Vth: 1.81

While this liquid crystal composition was left in a freezer at −20° C., development of smectic phase and deposition of crystals were not observed even over 60 days.

EXAMPLE 30 (USE EXAMPLE 25)

Physical property values of the liquid crystal composition of Composition Example 22 were as follows:

NI: 97.4, Δε: 6.5, Δn: 0.139, η: 38.1, Vth: 2.01, VHR: 97.6, 96.4, 96.0

Pitch of the liquid crystal composition prepared by dissolving 0.2 part by weight of optically active compound CM-43L to 100 parts by weight of the liquid crystal composition of Composition Example 22 was 76 μm.

EXAMPLE 31 (COMPARATIVE EXAMPLE 1)

VHR of liquid crystal composition (G) which was obtained by the same manner as in Example 13 with the exception that 9% of the compound, 3,3'-difluoro-4'-decyloxybiphenyl 4-yl trans-4 heptylcyclohexane carboxylate (7-HEB(2F)B(3F)-1O) described in Japanese Patent Application laid-open No. Sho 64-29342 was used in place of 3,3',3"-trifluoro-4,4"-dipropoxyterphenyl (Compound No. 1) and 3,3'-difluoro-4'-(trans-4-propylcyclohexyl)-4-propoxybiphenyl (Compound No. 183) were as follows:

VHR: 97.8, 84.2, 79.8

From this fact, it was found out that the compound of the present invention have a high voltage holding ratio compared with a known compound 3,3'-difluoro-4'-decyloxybiphenyl 4-yl trans-4 heptylcyclohexane carboxylate having ester bond.

EXAMPLE 32 (COMPARATIVE EXAMPLE 2)

Physical property values of liquid crystal composition (H) which was obtained in the same manner as in Example 11 with the exception that 10.0% of 3,3'-difluoro-4-propxymrthyl-4-propylterphenyl (3O1-BB(2F)B(3F)-3) which is a compound included in the general formula described in GB 2,258,232A and 10% of 3,3'-difluoro-4'-((4-ethylphenyl)methoxy)-4-propoxybiphenyl (2-BCH$_2$OB (2F)B(3F)—O3) which is included in the general formula described in Japanese Patent Application laid-open No. Hei 3-141237 were used in place of 3,3'-difluoro-4'-(trans-4-propylcyclohexyl)-4-propoxybiphenyl (Compound No. 183) and 3,3'-difluoro-4'-((trans-4-propylcyclohexyl) methoxy)-4-propoxybiphenyl (Compound No. 276) were as follows:

NI: 77.5, Δε: −3.8, Δn: 0.109

When this liquid crystal composition (H) was left in a freezer at −20° C., smectic phase developed in one day.

From this fact, it is understood that the compounds of the present invention hardly exhibit smectic phase even at low temperatures and have a negative and large Δε compared with known compounds.

EXAMPLE 33 (COMPARATIVE EXAMPLE 3)

Physical property values of liquid crystal composition (I) which was obtained in the same manner as in Example 11 with the exception that 10.0% of 2,3-difluoro-4-(trans-4-(trans-4-propylcyclohexyl)cyclohexyl)propoxybenzene (3-HHB(2,3F)—O3) which is included in the general formula described in Japanese translated PCT patent application laid-open (Tokuhyo) No. Hei 2-503441 and 10% of 2,3-difluoro-4-((trans-4-propylcyclohexyl)-methoxy)-propoxybiphenyl (3-HCH$_2$OBB(2,3F)—O3) were used in place of 3,3'-difluoro-4'-(trans-4-propylcyclohexyl)-4-propoxybiphenyl (Compound No. 183) and 3,3'-difluoro-4'-((trans-4-propylcyclohexyl)methoxy)-4-propoxybiphenyl (Compound No. 276) were as follows:

NI: 79.8, Δε: −3.7, Δn: 0.091

When this liquid crystal composition (I) was left in a freezer at −20° C., smectic phase developed in four days.

From this fact, it is understood that the compounds of the present invention hardly exhibit smectic phase even at low temperatures and have a negative and large Δε compared with known compounds.

Liquid crystalline compounds of the present invention have an extremely high voltage holding ratio and a low threshold voltage, are remarkably small in their dependency on temperature, hardly exhibit smectic phase, and further are improved in miscibility with other liquid crystal materials. Besides, novel liquid crystalline compounds having desired physical properties can be provided by selecting proper substituents in the liquid crystalline compounds of the present invention.

INDUSTRIAL APPLICABILITY

Accordingly, novel liquid crystal compositions having an extremely high voltage holding ratio, being remarkably small in its dependency on temperature, having a low threshold voltage and a suitable height of Δn and Δε, and being excellent in stability and miscibility with other liquid crystal materials can be provided by using the liquid crystalline compound of the present invention as component of liquid crystal compositions, and excellent liquid crystal display devices of IPS mode or VA mode can be provided by using the liquid crystal composition.

We claim:
1. A 3,3'-difluorobiphenyl derivative expressed by the general formula (1)

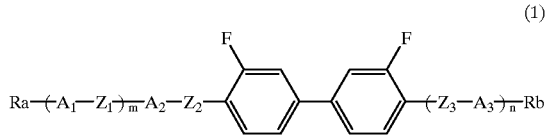

(1)

wherein Ra and Rb each independently represent a straight chain or branched alkyl group having 1 to 20 carbon atoms in which alkyl group not-adjacent any methylene group (—$CH_2$—) may be replaced by oxygen atom, and any hydrogen atom in the alkyl group may be replaced by a halogen atom; $A_1$, $A_2$ and $A_3$ each independently represent trans-1,4-cyclohexylene, dioxane-2,5-diyl, or tetrahydropyran-2,5-diyl, or 1,4-phenylene in which one or more hydrogen atoms may be replaced by fluorine atom; $Z_1$, $Z_2$ and $Z_3$ each independently represent —$(CH_2)_2$—, —$(CH_2)_4$—, —$CH_2O$—, —$(CH_2)_3O$— or single bond; m and n are independently 0 or 1 provided that when both m and n are 0, and $A_2$ represents 1,4-phenylene, then at least one hydrogen atom on $A_2$ is replaced by fluorine atom.

2. The 3,3'-difluorobiphenyl derivative according to claim 1 wherein both m and n are 0.

3. The 3,3'-difluorobiphenyl derivative according to claim 1 wherein either m or n is 1.

4. The 3,3'-difluorobiphenyl derivative according to claim 2 wherein $A_2$ is trans-1,4-cyclohexylene.

5. The 3,3'-difluorobiphenyl derivative according to claim 2 wherein $A_2$ is dioxane-2,5-diyl, or tetrahydropyran-2,5-diyl.

6. The 3,3'-difluorobiphenyl-derivative according to claim 2 wherein $A_2$ is 1,4-phenylene in which at least one hydrogen atom is replaced by fluorine atom.

7. A liquid crystal composition comprising at least one derivative defined in claim 1.

8. A liquid crystal composition comprising, as a first component, at least one derivative defined in claim 1, and comprising, as a second component, at least one compound selected from the group consisting of the compounds expressed by any one of the general formulas (2), (3) and (4)

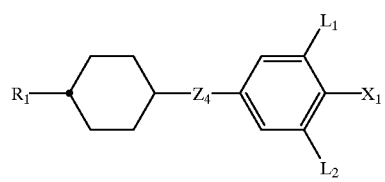

(2)

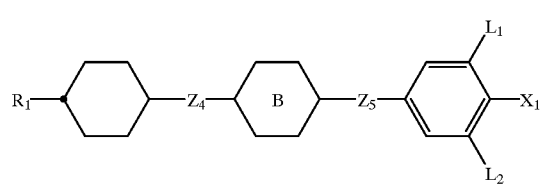

(3)

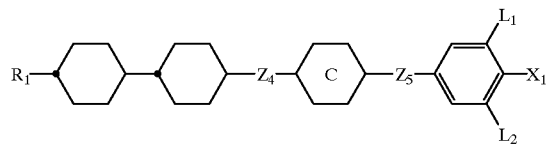

(4)

wherein $R_1$ represents an alkyl group having 1 to 10 carbon atoms in which alkyl group not-adjacent any methylene group may be replaced by oxygen atom or —CH=CH—, and any hydrogen atom in the alkyl group may be replaced by fluorine atom; $X_1$ represents fluorine atom, chlorine atom, —$OCF_3$, —$OCF_2H$, —$CF_3$, —$CF_2H$, —$CFH_2$, —$OCF_2CF_2H$ or —$OCF_2CFHCF_3$; $L_1$ and $L_2$ each independently represent hydrogen atom or fluorine atom; $Z_4$ and $Z_5$ each independently represent —$(CH_2)_2$—, —$(CH_2)_4$—, —COO—, —$CF_2O$—, —$OCF_2$—, —CH=CH—, or single bond; ring B represents trans-1,4-cyclohexylene or 1,3-dioxane-2,5-diyl, or 1,4-phenylene in which hydrogen atom may be replaced by fluorine atom; and ring C represents trans-1,4-cyclohexylene, or 1,4-phenylene in which hydrogen atom may be replaced by fluorine atom.

9. A liquid crystal composition comprising, as a first component, at least one derivative defined in claim 1, and comprising, as a second component, at least one compound selected from the group consisting of the compounds expressed by the general formula (5) or (6)

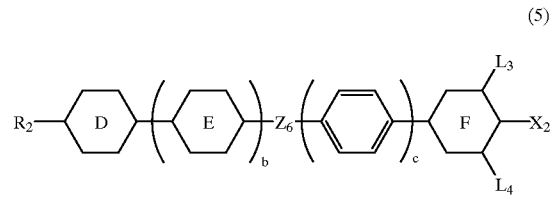

(5)

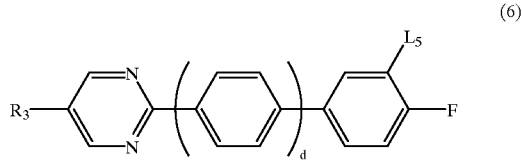

(6)

wherein $R_2$ and $R_3$ each independently represent an alkyl group having 1 to 10 carbon atoms in which alkyl group not-adjacent any methylene group may be replaced by oxygen atom or —CH=CH—, and any hydrogen atom in the alkyl group may be replaced by fluorine atom; $X_2$ represents —CN or —C≡C—CN; ring D represents trans-1,4-cyclohexylene, 1,4-phenylene, 1,3-dioxane-2,5-diyl, or pyrimidine-2,5-diyl; ring E represents trans-1,4-cyclohexylene or pyrimidine-2,5-diyl, or 1,4-phenylene in which hydrogen atom may be replaced by fluorine atom; ring F represents trans-1,4-cyclohexylene or 1,4-phenylene; $Z_6$ represents —$(CH_2)_2$—, —COO—, or single bond; $L_3$, $L_4$ and $L_5$ each independently represent hydrogen atom and or fluorine atom; b, c, and d are independently 0 or.

10. A liquid crystal composition comprising, as a first component, at least one derivative defined in claim 1, comprising, as a second component, at least one compound selected from the group consisting of the compounds expressed by any one of the general formulas (2), (3), and (4)

(2)
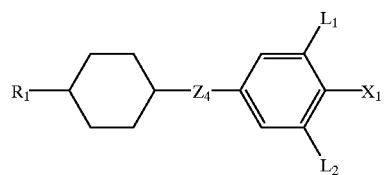

(3)
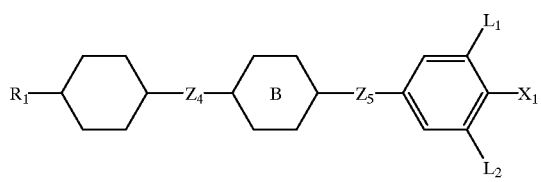

(4)
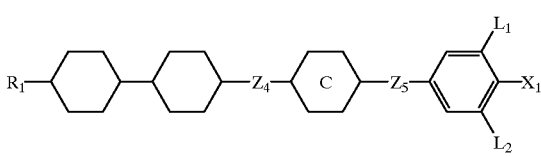

wherein $R_1$ represents an alkyl group having 1 to 10 carbon atoms in which alkyl group not-adjacent any methylene group may be replaced by oxygen atom or —CH=CH—, and any hydrogen atom in the alkyl group may be replaced by fluorine atom; $X_1$ represents fluorine atom, chlorine atom, —OCF$_3$, —OCF$_2$H, —CF$_3$, —CF$_2$H, —CFH$_2$, —OCF$_2$CF$_2$H, or —OCF$_2$CFHCF$_3$; $L_1$ and $L_2$ each independently represent hydrogen atom or fluorine atom: $Z_4$ and $Z_5$ each independently represent —(CH$_2$)$_2$—, —(CH$_2$)$_4$—, —COO—, —CF$_2$O—, —OCF$_2$—, —CH=CH—, or single bond; ring B represents trans-1,4-cyclohexylene or 1,3-dioxane-2,5-diyl, or 1,4-phenylene in which hydrogen atom may be replaced by fluorine atom; and ring C represents trans-1,4-cyclohexylene, or 1,4-phenylene in which hydrogen atom may be replaced by fluorine atom, and comprising, as a third component, at least one compound selected from the group consisting of the compounds expressed by any one of the general formulas (7), (8), and (9)

(7)
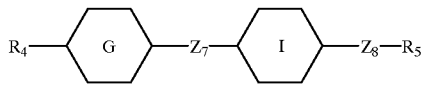

(8)
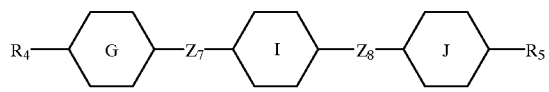

(9)
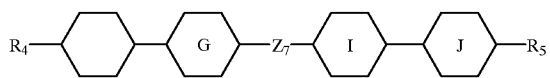

wherein $R_4$ and $R_5$ each independently represent an alkyl group having 1 to 10 carbon atoms in which alkyl group not-adjacent any methylene group may be replaced by oxygen atom or —CH=CH—, and any hydrogen atom in the alkyl group may be replaced by fluorine atom; ring G, ring I, and ring J each independently represent trans-1,4-cyclohexylene or pyrimidine-2,5-diyl, or 1,4-phenylene in which hydrogen atom may be replaced by fluorine atom; and $Z_7$ and $Z_8$ each independently represent —C≡C—, —COO—, —(CH$_2$)$_2$—, —CH=CH—, or single bond.

11. A liquid crystal composition comprising, as a first component, at least one derivative defined in claim 1, comprising, as a second component, at least one compound selected from the group consisting of the compounds expressed by the general formula (5) or (6)

(5)
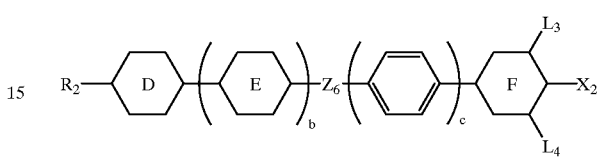

(6)
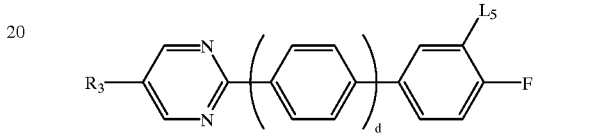

wherein $R_2$ and $R_3$ each independently represent an alkyl group having 1 to 10 carbon atoms in which alkyl group not-adjacent any methylene group may be replaced by oxygen atom or —CH=CH—, and any hydrogen atom in the alkyl group may be replaced by fluorine atom; $X_2$ represents —CN or —C≡C—CN; ring D represents trans-1,4-cyclohexylene, 1,4-phenylene, 1,3-dioxane-2,5-diyl, or pyrimidine-2,5-diyl; ring E represents trans-1,4-cyclohexylene or pyrimidine-2,5-diyl, or 1,4-phenylene in which hydrogen atom may be replaced by fluorine atom; ring F represents trans-1,4-cyclohexylene or 1,4-phenylene; $Z_6$ represents —(CH$_2$)$_2$—, —COO—, or single bond; $L_3$, $L_4$, and $L_5$ each independently represent hydrogen atom or fluorine atom; and b, c, and d are independently 0 or 1, and comprising, as a third component, at least one compound selected from the group consisting of the compounds expressed by any one of the general formulas (7), (8), and (9)

(7)
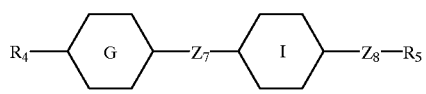

(8)
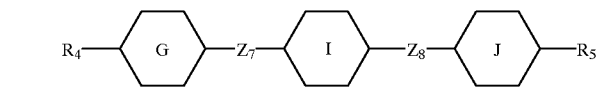

(9)
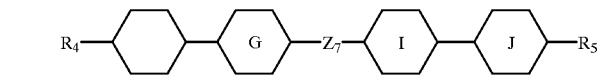

wherein $R_4$ and $R_5$ each independently represent an alkyl group having 1 to 10 carbon atoms in which alkyl group not-adjacent any methylene group may be replaced by oxygen atom or —CH=CH—, and any hydrogen atom in the alkyl group may be replaced by fluorine atom; ring G, ring I, and ring J each independently represent trans-1,4-cyclohexylene or pyrimidine-2,5-diyl, or 1,4-phenylene in which hydrogen atom may be replaced by fluorine atom; and $Z_7$ and $Z_8$ each independently represent —C≡C—, —COO—, —(CH$_2$)$_2$—, —CH=CH—, or single bond.

12. A liquid crystal composition comprising, as a first component, at least one derivative defined in claim 1, and comprising, as a second component, at least one compound selected from the group consisting of the compounds expressed by any one of the general formulas (10), (11), and (12)

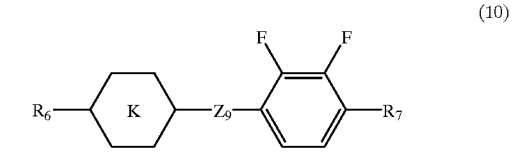
(10)

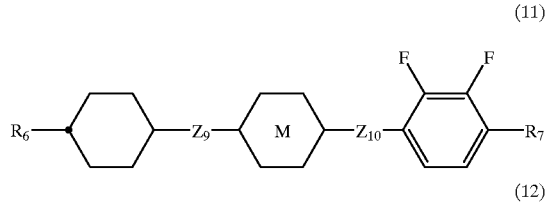
(11)

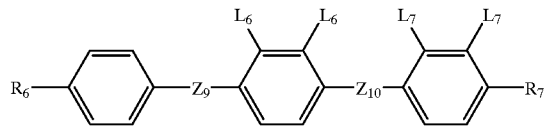
(12)

wherein $R_6$ and $R_7$ each independently represent an alkyl group having 1 to 10 carbon atoms in which alkyl group not-adjacent any methylene group may be replaced by oxygen atom or —CH=CH—, and any hydrogen atom in the alkyl group may be replaced by fluorine atom; ring K and ring M each independently represent trans-1,4-cyclohexylene or 1,4-phenylene; $L_6$ and $L_7$ each each independently represent hydrogen atom or fluorine atom but in no case do $L_6$ and $L_7$ simultaneously represent hydrogen atom; and $Z_9$ and $Z_{10}$ each independently represent —(CH$_2$)$_2$—, —COO—, or single bond.

13. A liquid crystal composition comprising, as a first component, at least one derivative defined in claim 1, comprising, as a second component, at least one compound selected from the group consisting of the compounds expressed by any one of the general formulas (7), (8), and (9)

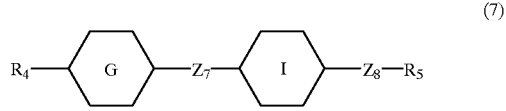
(7)

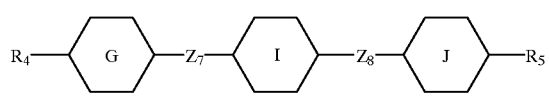
(8)

(9)

wherein $R_4$ and $R_5$ each independently represent an alkyl group having 1 to 10 carbon atoms in which alkyl group not-adjacent any methylene group may be replaced by oxygen atom or —CH=CH—, and any hydrogen atom in the alkyl group may be replaced by fluorine atom; ring G, ring I, and ring J each independently represent trans-1,4-cyclohexylene or pyrimidine-2,5-diyl, or 1,4-phenylene in which hydrogen atom may be replaced by fluorine atom; and $Z_7$ and $Z_8$ each independently represent —C≡C—, —COO—, —(CH$_2$)$_2$—, —CH=CH—, or single bond, and comprising, as a third component, at least one compound selected from the group consisting of the compounds expressed by any one of the general formulas (10), (11), and (12)

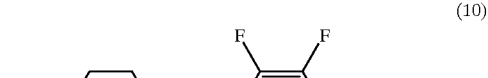
(10)

(11)

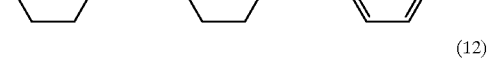
(12)

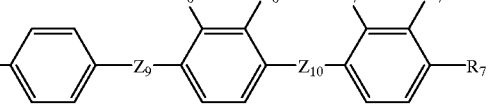

wherein $R_6$ and $R_7$ each independently represent an alkyl group having 1 to 10 carbon atoms in which alkyl group not-adjacent any methylene group may be replaced by oxygen atom or —CH=CH—, and any hydrogen atom in the alkyl group may be replaced by fluorine atom; ring K and ring M each independently represent trans-1,4-cyclohexylene or 1,4-phenylene; $L_6$ and $L_7$ each independently represent hydrogen atom or fluorine atom but in no case do $L_6$ and $L_7$ simultaneously represent hydrogen atom; and $Z_9$ and $Z_{10}$ each independently represent —(CH$_2$)$_2$—, —COO—, or single bond.

14. A liquid crystal composition comprising, as a first component, at least one derivative defined in claim 1, comprising, as a second component, at least one compound selected from the group consisting of the compounds expressed by any one of the general formulas (2), (3), and (4)

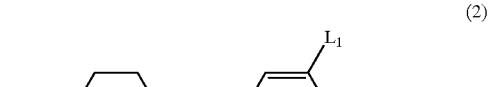
(2)

(3)

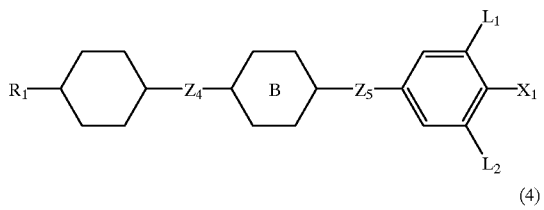

(4)

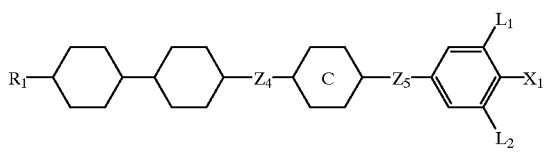

wherein $R_1$ represents an alkyl group having 1 to 10 carbon atoms in which alkyl group not-adjacent any methylene group may be replaced by oxygen atom or —CH=CH—, and any hydrogen atom in the alkyl group may be replaced by fluorine atom; $X_1$ represents fluorine atom, chlorine atom, —OCF$_3$, —OCF$_2$H, —CF$_3$, —CF$_2$H, —CFH$_2$, —OCF$_2$CF$_2$H, or —OCF$_2$CFHCF$_3$; $L_1$ and $L_2$ each independently represent hydrogen atom or fluorine atom; $Z_4$ and $Z_5$ each independently represent —(CH$_2$)$_2$—, —(CH$_2$)$_4$—, —COO—, —CF$_2$O—, —OCF$_2$—, —CH=CH—, or single bond; ring B represents trans-1,4-cyclohexylene or 1,3-dioxane-2,5-diyl, or 1,4-phenylene in which hydrogen atom may be replaced by fluorine atom; and ring C represents trans-1,4-cyclohexylene, or 1,4-phenylene in which hydrogen atom may be replaced by fluorine atom, comprising, as a third component, at least one compound selected from the group consisting of the compounds expressed by the general formula (5) or (6)

(5)

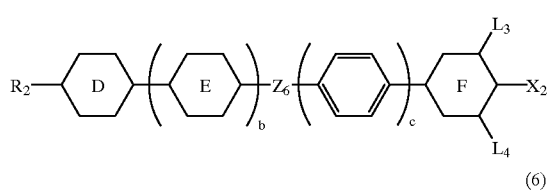

(6)

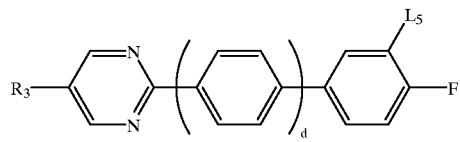

wherein $R_2$ and $R_3$ each independently represent an alkyl group having 1 to 10 carbon atoms in which alkyl group not-adjacent any methylene group may be replaced by oxygen atom or —CH=CH—, and any hydrogen atom in the alkyl group may be replaced by fluorine atom; $X_2$ represents —CN or —C≡C—CN; ring D represents trans-1,4-cyclohexylene, 1,4-phenylene, 1,3-dioxane-2,5-diyl, or pyrimidine-2,5-diyl; ring E represents trans-1,4-cyclohexylene or pyrimidine-2,5-diyl, or 1,4-phenylene in which hydrogen atom may be replaced by fluorine atom; ring F represents trans-1,4-cyclohexylene or 1,4-phenylene; $Z_6$ represents —(CH$_2$)$_2$—, —COO—, or single bond; $L_3$, $L_4$, and $L_5$ each independently represent hydrogen atom or fluorine atom; and b, c, and d are independently 0 or 1, and comprising, as a fourth component, at least one compound selected from the group consisting of the compounds expressed by any one of the general formulas (7), (8), and (9)

(7)

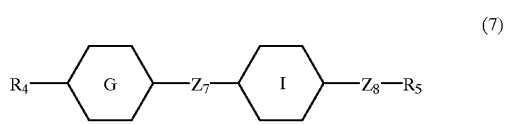

(8)

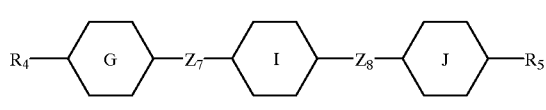

(9)

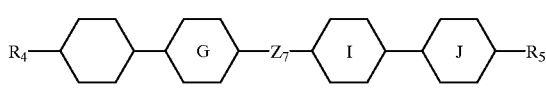

wherein $R_4$ and $R_5$ each independently represent an alkyl group having 1 to 10 carbon atoms in which alkyl group not-adjacent any methylene group may be replaced by oxygen atom or —CH=CH—, and any hydrogen atom in the alkyl group may be replaced by fluorine atom; ring G, ring I, and ring J each independently represent trans-1,4-cyclohexylene or pyrimidine-2,5-diyl, or 1,4-phenylene in which hydrogen atom may be replaced by fluorine atom; and $Z_7$ and $Z_8$ each independently represent —C≡C—, —COO—, —(CH$_2$)$_2$—, —CH=CH—, or single bond.

15. A liquid crystal composition further comprising at least one optically active compound in addition to the liquid crystal composition defined in claim 7.

16. A liquid crystal display device comprising a liquid crystal composition defined in claim 7.

* * * * *